United States Patent
Bakker et al.

(10) Patent No.: US 11,873,338 B2
(45) Date of Patent: Jan. 16, 2024

(54) CLEC12AXCD3 BISPECIFIC ANTIBODIES AND METHODS FOR THE TREATMENT OF DISEASE

(71) Applicant: Merus N.V., Utrecht (NL)

(72) Inventors: Alexander Berthold Hendrik Bakker, Utrecht (NL); Cornelis Jacob Johannes George Bol, Utrecht (NL); Pieter Fokko Van Loo, Utrecht (NL); Leonardo Andres Sirulnik, Utrecht (NL); Ernesto Isaac Wasserman, Utrecht (NL)

(73) Assignee: Merus N.V., Utrecht (NL)

( * ) Notice: Subject to any disclaimer, the term of this patent is extended or adjusted under 35 U.S.C. 154(b) by 235 days.

(21) Appl. No.: 17/294,338

(22) PCT Filed: Dec. 20, 2019

(86) PCT No.: PCT/NL2019/050864
§ 371 (c)(1),
(2) Date: May 14, 2021

(87) PCT Pub. No.: WO2020/130829
PCT Pub. Date: Jun. 25, 2020

(65) Prior Publication Data
US 2022/0010013 A1     Jan. 13, 2022

(30) Foreign Application Priority Data

Dec. 20, 2018  (EP) .................................... 18214478

(51) Int. Cl.
| C07K 16/28 | (2006.01) |
| A61P 35/00 | (2006.01) |
| A61K 35/28 | (2015.01) |
| A61K 39/00 | (2006.01) |

(52) U.S. Cl.
CPC .......... *C07K 16/2809* (2013.01); *A61K 35/28* (2013.01); *A61P 35/00* (2018.01); *C07K 16/2851* (2013.01); *A61K 2039/545* (2013.01); *C07K 2317/31* (2013.01); *C07K 2317/73* (2013.01); *C07K 2317/74* (2013.01); *C07K 2317/92* (2013.01)

(58) Field of Classification Search
CPC ............ C07K 16/2809; C07K 16/2851; C07K 2317/31; C07K 2317/73; A61K 35/28; A61K 2039/545; A61P 35/00
See application file for complete search history.

(56) References Cited

U.S. PATENT DOCUMENTS

| 9,248,181 B2 | 2/2016 | De Kruif et al. |
| 9,255,141 B2 | 2/2016 | Wong et al. |
| 9,328,159 B2 | 5/2016 | Wong et al. |
| 9,358,286 B2 | 6/2016 | De Kruif et al. |
| 2014/0120096 A1 | 5/2014 | Bakker et al. |
| 2016/0368988 A1 | 12/2016 | Bakker et al. |

FOREIGN PATENT DOCUMENTS

| WO | WO-2005000894 A2 | 1/2005 | |
| WO | WO-2005118635 A2 | 12/2005 | |
| WO | WO-2008027236 A2 | 3/2008 | |
| WO | WO-2009157771 A2 | 12/2009 | |
| WO | WO-2010108127 A1 | 9/2010 | |
| WO | WO-2013157954 A1 | 10/2013 | |
| WO | WO-2014051433 A1 | 4/2014 | |
| WO | WO-2016205200 A1 * | 12/2016 | ......... A61K 39/3955 |
| WO | WO-2017010874 A1 | 1/2017 | |
| WO | WO-2017167919 A1 | 10/2017 | |
| WO | WO-2017182427 A1 | 10/2017 | |
| WO | WO-2018093821 A1 | 5/2018 | |
| WO | WO-2020130829 A1 | 6/2020 | |

OTHER PUBLICATIONS

NCT03038230, A Phase 1, Multinational Study of MCLA-117 in Acute Myelogenous Leukemia, 2017, Clinical Trials, retrieved from: https://clinicaltrials.gov/ct2/show/NCT03038230 (Year: 2017).*
Ball et al., Autologous Bone Marrow Transplantation for Acute Myeloid Leukemia Using Monoclonal Antibody-Purged Bone Marrow, 1990, Blood, vol. 75, No. 5, pp. 1199-1206 (Year: 1990).*
Van Loo et al., Preclinical Evaluation of MCLA117, a CLEC12AxCD3 Bispecific Antibody Effectively Targeting a Novel Leukemic Stem Cell Associated Antigen in AML, 2015, Blood, vol. 126, Issue 23, Abstract 325 (Year: 2015).*
Noordhuis et al., Targeting of CLEC12A in Acute Myeloid Leukemia by Antibody-Drug-Conjugates and Bispecific CLL-1xCD3 BiTE Antibody, 2010, Blood, vol. 116, Issue 21, Abstract 2890 (Year: 2010).*
Tourneau et al., Dose Escalation Methods in Phase I Cancer Clinical Trials, 2009, Journal of the National Cancer Institute, vol. 101, Issue 10, pp. 708-720 (Year: 2009).*

(Continued)

*Primary Examiner* — Adam Weidner
*Assistant Examiner* — Brittney E Donoghue
(74) *Attorney, Agent, or Firm* — Sterne, Kessler, Goldstein & Fox P.L.L.C.; Paul A. Calvo

(57) ABSTRACT

The disclosure relates to means and methods of treating a subject for a CLEC12A positive cancer. In some embodiments the method comprises treating the subject in need thereof with two or more administrations of a bispecific antibody that binds CD3 and CLEC12A, wherein in a first administration an first amount of the bispecific antibody is administered and wherein in each of the subsequent administrations the amount of bispecific antibody is higher than the amount of bispecific antibody in the first administration. In some embodiments CLEC12A positive cancer treatment methods are provided at intervals and dosing regimens that spare hemopoietic stem cell compartment allowing for recovery of normal CLEC12A positive hemopoietic cells.

13 Claims, 34 Drawing Sheets
(6 of 34 Drawing Sheet(s) Filed in Color)
Specification includes a Sequence Listing.

(56) References Cited

OTHER PUBLICATIONS

Aigner, M., et al., "T Lymphocytes Can Be Effectively Recruited for Ex Vivo and in Vivo Lysis of AML blasts by a novel CD33/CD3-bispecific BiTE antibody construct," Leukemia 27(5):1107-1115, Nature Publishing Group, England (Apr. 2013).

Al-Hussaini, M., et al., "Targeting CD123 in Acute Myeloid Leukemia Using a T-cell-directed Dual-affinity Retargeting Platform," Blood 127(1):122-131, Elsevier, United States (Jan. 2016).

Anonymous: "MCLA-117 in Acute Myelogenous Leukemia," clinical trials.gov.Jan. 27, 2017 (Jan. 27, 2017). pp. 1-10. XP055587691. Retrieved from the Internet:URL: https://clinicaltrials.gov/ct2/history/NCT03038230?V_3=View#StudyPageTop.

Arrighi, J.R., et al., "Tnf-alpha Induces the Generation of Langerin/(Cd207)+ Immature Langerhans-type Dendritic Cells From Both Cd14-cd1a and Cd14+cd1a-Precursors Derived From Cd34+ Cord Blood Cells," European Journal of Immunology 33(7):2053-2063, Wiley-VCH, Germany (Jul. 2003).

Baeuerle, P., et al., "Bispecific T-Cell Engaging Antibodies for Cancer Therapy," Cancer Research, vol. 69(12), pp. 4941-4944 (2009).

Bakker, A.B., et al., "C-type Lectin-like Molecule-1: a Novel Myeloid Cell Surface Marker Associated With Acute Myeloid Leukemia," Cancer Research 64(22):8443-8450, American Association for Cancer Research, United States (Nov. 2004).

Bill, M., et al., "Mapping the CLEC12A Expression on Myeloid Progenitors in Normal Bone Marrow; Implications for Understanding CLEC12A-related Cancer Stem Cell Biology," Journal of Cellular and Molecular Medicine 22(4):2311-2318, Wiley-Blackwell, England (Apr. 2018).

Brinkmann, U and Kontermann, R.E., "The Making of Bispecific Antibodies," MABS 9(2):182-212, Taylor & Francis Group, England (Feb.-Mar. 2017).

Burnett, A., et al., "Therapeutic Advances in Acute Myeloid Leukemia," Journal of Clinical Oncology 29(5):487-494, American Society of Clinical Oncology, United States (Feb. 2011).

Chen, C.H., et al., "Dendritic-cell-associated C-type Lectin 2 (DCAL-2) Alters Dendritic-cell Maturation and Cytokine Production," Blood 107(4):1459-1467, American Society of Hematology, United States (Feb. 2006).

De Kruif et al., "Human Immunoglobulin Repertoires Against Tetanus Toxoid Contain a Large and Diverse Fraction of High-affinity Promiscuous V(H) Genes," Journal of Molecular Biology 387(3):548-558, Elsevier, England (Apr. 2009).

De Kruif, J., et al., "Generation of Stable Cell Clones Expressing Mixtures of Human Antibodies," Biotechnology and Bioengineering 106(5):741-750, Wiley, United States (Aug. 2010).

De Nardis, C., et al., "A New Approach for Generating Bispecific Antibodies Based on a Common Light Chain Format and the Stable Architecture of Human Immunoglobulin G1," Journal of Biological Chemistry, 292(35):14706-14717, American Society for Biochemistry and Molecular Biology, United States (Sep. 2017).

GenBank, "*Homo sapiens* C-type Lectin Protein CLL-1 mRNA, Complete Cds," Accession No. AF247788.1, accessed at https://www.ncbi.nlm.nih.gov/nuccore/19716160/, Mar. 26, 2002, 1 page.

GenBank, "*Homo sapiens* C-type Lectin-like Molecule-1 (CLL1) mRNA, Complete cds," GenBank accessionNo. AY547296.1, accessed at URL: https://www.ncbi.nlm.nih.gov/nuccore/AY547296.

GenBank, "*Homo sapiens* Dendritic Cell Associated Lectin 2 mRNA, Complete Cds," Accession No. AY426759.1, accessed at https://www.ncbi.nlm.nih.gov/nuccore/40362523/, Feb. 9, 2006, 2 pages.

GenBank: "*Homo sapiens* Myeloid Inhibitory C-type Lectin-like Receptor Isoform Alpha (Micl) Mrna, Complete Cds, Alternatively Spliced," accession No. AY498550.1, accessed at URL: https://www.ncbi.nlm.nih.gov/nuccore/AY498550.

Gunasekaran, K., et al., "Enhancing Antibody Fc Heterodimer Formation Through Electrostatic Steering Effects: Applications to Bispecific Molecules and Monovalent IgG," Journal of Biological Chemistry 285(25):19637-19646, American Society for Biochemistry and Molecular Biology, United States (Jun. 2010).

Han, Y., et al., "KLRL1, a Novel Killer Cell Lectinlike Receptor, Inhibits Natural Killer Cell Cytotoxicity," Blood 104(9):2858-2866, American Society of Hematology, United States (Nov. 2004).

International Search Report and Written Opinion for Application No. PCT/NL2019/050864, dated Mar. 23, 2020, European Patent Office, Rijswijk, 12 pages.

Zhao, X., et al., "Targeting C-type Lectin-like Molecule-1 for Antibody-mediated Immunotherapy in Acute Myeloid Leukemia," Haematologica 95(1):71-78, Ferrata Storti Foundation, Italy (Jan. 2010).

Juliusson, G., et al., "Acute Myeloid Leukemia in the Real World: Why Population-based Registries Are Needed," Blood 119(17):3890-3899, Elsevier, United States (Apr. 2012).

Kenderian, S.S., et al., "CD33-specific Chimeric Antigen Receptor T Cells Exhibit Potent Preclinical Activity Against Human Acute Myeloid Leukemia," Leukemia 29(8):1637-1647, Nature Publishing Group, England (Aug. 2015).

Kikushige, Y., et al., "TIM-3 as a Novel Therapeutic Target for Eradicating Acute Myelogenous Leukemia Stem Cells," International Journal of Hematology, 98(6): 627-633, Springer Japan, Japan (Dec. 2013).

Kontermann, R.E and Brinkmann, U., "Corrigendum to "Bispecific antibodies" [Drug Discov. Today Jul. 20, 2015 838-847]," Drug Discovery Today 24(7):1422, Elsevier Science Ltd., England (Jul. 2019).

Lahoud, M.H., et al., "The C-type Lectin Clec12a Present on Mouse and Human Dendritic Cells Can Serve as a Target for Antigen Delivery and Enhancement of Antibody Responses," Journal of Immunology 182(12):7587-7594, American Association of Immunologists, United States (Jun. 2009).

Larsen, H.O., et al., "Expression of the hMICL in Acute Myeloid Leukemia—a Highly Reliable Disease Marker at Diagnosis and During Follow-up," Cytometry. Part B, Clinical cytometry 82(1):3-8, Wiley-Liss, United States (Jan. 2012).

Le Dieu, R., et al., "Peripheral Blood T Cells in Acute Myeloid Leukemia (AML) Patients at Diagnosis Have Abnormal Phenotype and Genotype and Form Defective Immune Synapses With AML Blasts," Blood 114(18):3909-3916, Elsevier, United States (Oct. 2009).

Le Tourneau, C., et al., "Reporting of Time-to-event End Points and Tracking of Failures in Randomized Trials of Radiotherapy With or Without Any Concomitant Anticancer Agent for Locally Advanced Head and Neck Cancer," Journal of Clinical Oncology 27(35):5965-5971, American Society of Clinical Oncology, United States (Dec. 2009).

Leong, S.R., et al., "An Anti-CD3/anti-CLL-1 Bispecific Antibody for the Treatment of Acute Myeloid Leukemia," Retrieved from the Internet: URL: http://www.bloodjournal.org/content/129/5/609.full-text.pdf.

Lowenberg, B., et al., "High-Dose Daunorubicin in Older Patients With Acute Myeloid Leukemia," The New England Journal of Medicine 361(13):1235-1248, Massachusetts Medical Society, United States (Sep. 2009).

Lu, H., et al., "Targeting Human C-type Lectin-like Molecule-I (CLLI) with a Bispecific Antibody for Immunotherapy of Acute Myeloid Leukemia," Angew. Chem.Int. Ed. 53:9841-9845, Wiley-VCH Verlag Gmbh & Co. KGaA, Germany (2014).

Marshall, A.S., et al., "Identification and Characterization of a Novel Human Myeloid Inhibitory C-type Lectin-like Receptor (MICL) That Is Predominantly Expressed on Granulocytes and Monocytes," The Journal of Biological Chemistry 279(15):14792-14802, American Society for Biochemistry and Molecular Biology, United States (Apr. 2004).

Morris, G.E., "Overview. Choosing a Method for Epitope Mapping," Methods in Molecular Biology 66:1-9, Humana Press, United States (1996).

Moshaver, B., et al., "Identification of a Small Subpopulation of Candidate Leukemia-initiating Cells in the Side Population of Patients With Acute Myeloid Leukemia," Stem Cells 26(12):3059-3067, AlphaMed Press, United States (Dec. 2008).

(56) References Cited

OTHER PUBLICATIONS

Needleman, S.B. and Wunsch, C.D., "A General Method Applicable to the Search for Similarities in the Amino Acid Sequence of Two Proteins," Journal of Molecular Biology 48(3):443-453, Elsevier, England (Mar. 1970).
Notta, F., et al., "Distinct Routes of Lineage Development Reshape the Human Blood Hierarchy Across Ontogeny," Science 351(6269):aab2116, American Association for the Advancement of Science, United States (Jan. 2016).
Oganesyan, V., et al., "Structural Characterization of a Human Fc Fragment Engineered for Lack of Effector Functions," Acta Crystallographica. Section D, Biological Crystallography 64(Pt 6):700-704, Wiley-Blackwell, United States (Jun. 2008).
Oran, B and Weisdorf D.J., "Survival for Older Patients With Acute Myeloid Leukemia: a Population-based Study," Haematologica 97(12):1916-1924, Ferrata Storti Foundation, Italy (Dec. 2012).
Pizzitola, I., et al., "Chimeric Antigen Receptors Against Cd33/cd123 Antigens Efficiently Target Primary Acute Myeloid Leukemia Cells in Vivo," Leukemia 28(8):1596-1605, Nature Publishing Group, England (Aug. 2014).
Rice, P., et al., "EMBOSS: The European Molecular Biology Open Software Suite," Trends in Genetics 16(6):276-277, Elsevier Trends Journals, England (Jun. 2000) Retrieved from the Internet: (URL: http://emboss.bioinformatics.nl/).
Schaefer, G., et al., "A Two-in-one Antibody Against Her3 and Egfr Has Superior Inhibitory Activity Compared With Monospecific Antibodies," Cancer cell 20(4):472-486, Cell Press, United States (Oct. 2011).
Sheridan, C., "Despite Slow Progress, Bispecifics Generate Buzz," Nature Biotechnology 34(12):1215-1217, Nature America Publishing, United States (Dec. 2016).
Spiess, C., et al., "Alternative Molecular Formats and Therapeutic Applications for Bispecific Antibodies," Molecular Immunology 67(2 Pt A):95-106, Pergamon Press, England (Oct. 2015).

Taussig, D.C., et al., "Hematopoietic Stem Cells Express Multiple Myeloid Markers: Implications for the Origin and Targeted Therapy of Acute Myeloid Leukemia," Blood 106(13):4086-4092, Elsevier, United States (Dec. 2005).
Toft-Peiersen, M., et al., "Unravelling the Relevance of Clec12a as a Cancer Stem Cell Marker in Myelodysplastic Syndrome," British Journal of Haematology 175(3):393-401, Wiley-Blackwell, England (Nov. 2016).
UniProtKB Database, "T-cell Surface Glycoprotein CD3 Delta Chain," Accession No. P04234, accessed at https://www.uniprot.org/uniprot/P04234.
UniProtKB Database, "T-cell Surface Glycoprotein CD3 Epsilon Chain," Accession No. P07766, accessed at https://www.uniprot.org/uniprot/P07766.
UniProtKB Database, "T-cell Surface Glycoprotein CD3 Gamma Chain," Accession No. P09693, accessed at https://www.uniprot.org/uniprot/P09693.
UniProtKB Database, "T-cell Surface Glycoprotein CD3 Zeta Chain," Accession No. P20963, accessed at https://www.uniprot.org/uniprot/P20963.
Van Rhenen, A., et al., "The Novel AML Stem Cell Associated Antigen CII-1 Aids in Discrimination Between Normal and Leukemic Stem Cells," Blood 110(7):2659-2666, American Society of Hematology, United States (Oct. 2007).
Wendeibo, O., et al., "Functional Characterization of T Lymphocytes Derived From Patients With Acute Myelogenous Leukemia and Chemotherapy-induced Leukopenia," Cancer Immunology, Immunotherapy 53(8):740-747, Springer Verlag, Germany (Aug. 2004).
Zhang, X., et al., "The Development of Bispecific Antibodies and Their Applications in Tumor Immune Escape," Experimental Hematology & Oncology 6:12, BioMed Central, England (May 2017).
Johnson, A., "Affimed Sinks After Placing Clinical Hold on Bispecific T Cell Engager," Biocentury Clinical News, 1 page, (Oct. 2018).
Leong, S. R., et al., "An Anti-CD3/anti-CLL-1 Bispecific Antibody for the Treatment of Acute Myeloid Leukemia," retrieved from http://www.bloodjournal.org/content/129/5/609.full-text.pdf, on Dec. 6, 2016, 20 pages (Dec. 1, 2016).

* cited by examiner

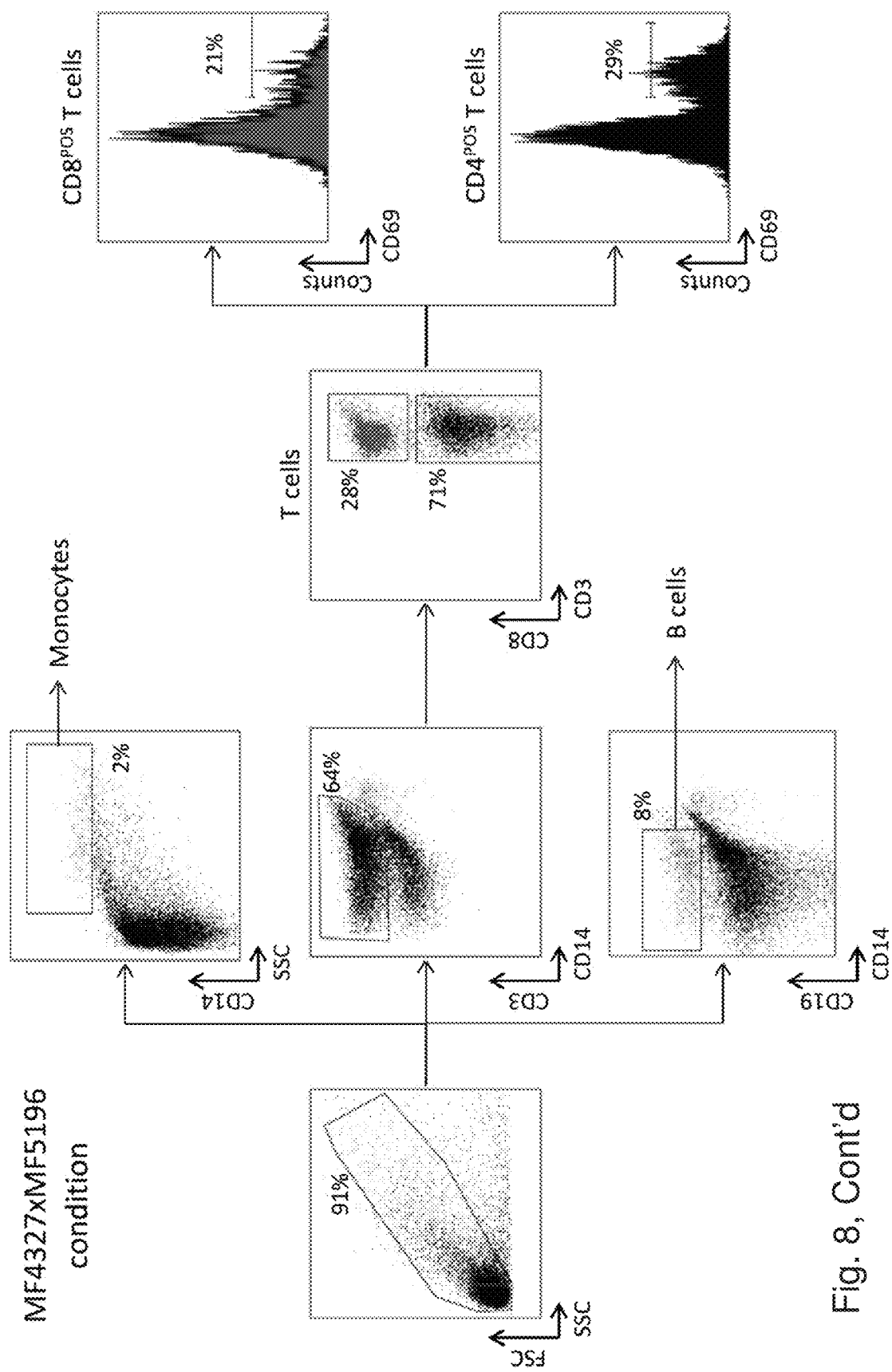
Fig. 8, Cont'd

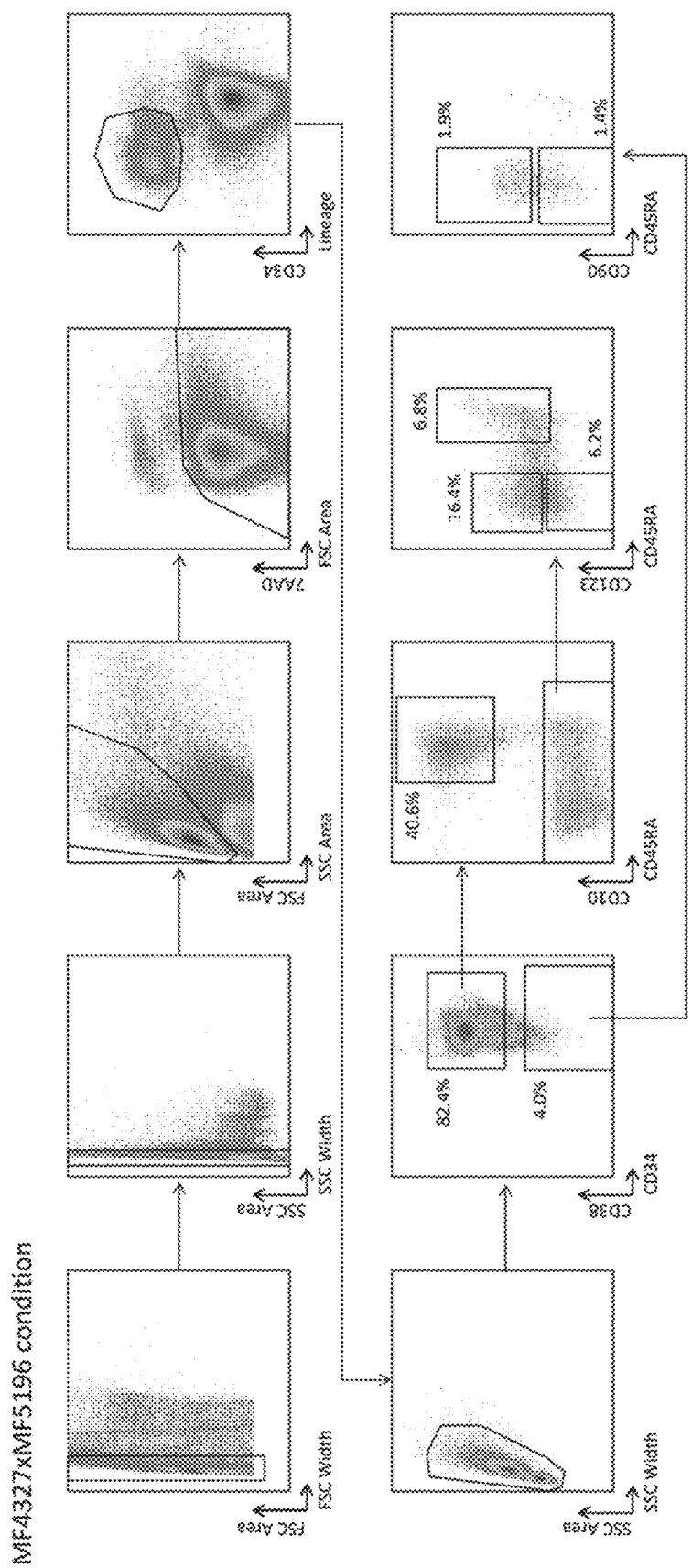
Fig. 11, Cont'd

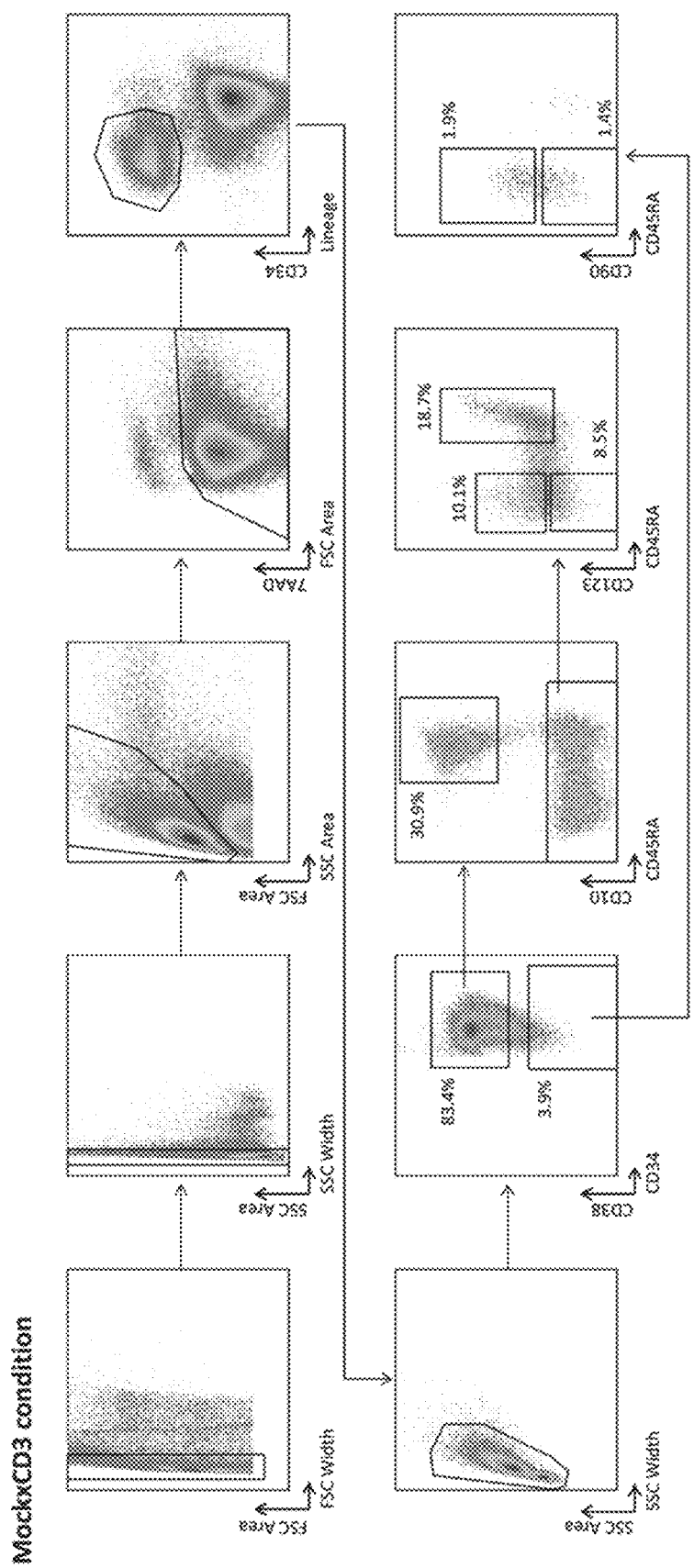
Fig. 11, Cont'd

CLEC12AXCD3 BISPECIFIC ANTIBODIES AND METHODS FOR THE TREATMENT OF DISEASE

The Sequence Listing submitted May 13, 2021, as a text file named "4096_0340001_Seqlisting_ST25.txt", created on May 10, 2021, and having a size of 50,035 bytes, is hereby incorporated by reference in its entirety.

The invention relates to the field of antibodies, in particular to the field of therapeutic antibodies. The antibodies can be used in the treatment of humans. More in particular the invention relates to antibodies and preferably bispecific antibodies for the treatment of a cancer.

BACKGROUND

Acute myeloid leukaemia (AML) is the third most common leukaemia worldwide, but over the past four decades has seen little progress in disease outcomes (Arrighi, Soulas et al. 2003, Lowenberg, Ossenkoppele et al. 2009, Burnett, Wetzler et al. 2011). The yearly incidence of AML in European adults is 5 to 8 per 100,000. In the United States 4 to 5 per 100,000 people are newly diagnosed for AML each year, with 10,000 people dying each year from AML. The five-year survival in young adults is approximately 40%, but this drops significantly with age to less than 25% in older patients. The majority of patients achieving morphologic complete remission after induction chemotherapy subsequently relapse within three years (Juliusson, Lazarevic et al. 2012, Oran and Weisdorf 2012). These patients therefore urgently require the development of new agents that have a more effective mode of action.

SUMMARY OF THE INVENTION

The present invention focuses on an antigen specifically expressed on AML blasts and leukaemic stem cells (LSCs), which is the C-type lectin domain family 12 member A or CLEC12A (also referred to as human myeloid inhibitory C-type lectin, hMICL, C-type lectin-like molecule-1, CLL-1, or CD371) (Bakker, van den Oudenrijn et al. 2004, van Rhenen, van Dongen et al. 2007). CLEC12A is a myeloid differentiation antigen that is expressed on leukemic cells in 90-95% of cases of either de novo or relapsed AML, irrespective of subtype (Bakker, van den Oudenrijn et al. 2004, Zhao, Singh et al. 2010, Larsen, Roug et al. 2012). CLEC12A is selectively expressed on CD34POSCD38NEG LSCs but, based on in vitro and vivo evidence, it is not expressed on normal hematopoietic stem cells (HSCs), erythroid precursors or megakaryocytes (van Rhenen, van Dongen et al. 2007, Kikushige and Miyamoto 2013).

In the present invention it is shown that CLEC12AxCD3 bispecific antibodies induce efficient T cell-mediated CLEC12A targeting and selectively eradicates leukaemic cells (including leukaemic stem cells) without affecting normal HSCs, thereby permitting normal haematopoiesis to be re-established swiftly after treatment and thereby limiting haematological toxicity.

Many of the T cell engager formats face issues, including a short serum half-life, immunogenicity and difficulties in terms of manufacture (Brinkmann and Kontermann 2017). The CLEC12AxCD3 bispecific antibodies of the present invention have a good serum half-life. The means and methods of the invention do not significantly induce an immune response against the therapeutic agent.

The invention provides a method of treating a subject for a CLEC12A positive cancer the method comprising treating the subject in need thereof with two or more administrations of a bispecific antibody that binds CD3 and CLEC12A, wherein in a first administration a first amount of the bispecific antibody is administered and wherein in each of the subsequent administrations the amount of bispecific antibody is higher than the amount of bispecific antibody in the first administration.

The invention also provides a bispecific antibody that binds CD3 and CLEC12A for use in a method of treatment of CLEC12A positive cancer in a subject, wherein said treatment comprises two or more administrations of a bispecific antibody that binds CD3 and CLEC12A, wherein in a first administration a first amount of the bispecific antibody is administered and wherein in each of the subsequent administrations the amount of bispecific antibody is higher than the amount of bispecific antibody in the first administration.

In an aspect the invention provides a method of purging CLEC12A positive hemopoietic cells, preferably CLEC12A positive malignant cells, from a subject and repopulating the hemopoietic system of said subject with normal cells, the method comprising administering to the subject in need thereof a bispecific antibody that binds CD3 and CLEC12A at intervals thereby killing CLEC12A positive malignant cells, and stimulating hemopoietic stem cells and/or hemopoietic progenitor cells of said subject to repopulate said hemopoietic system with newly formed hemopoietic stem cell derived cells, including CLEC12A positive cells. The hematopoietic stem cells reside in the bone marrow. The presence of deleterious CLEC12A positive cells can deprive healthy cells of nutrients and occupy the compartment thereby limiting normal growth and development of granulocytes, macrophage stem cells, which themselves give rise to basophil, neutrophil, eosinophil and monocyte blood cells. By removing deleterious CLEC12A positive cells from the bone marrow compartment through the manner of administration of the bispecific antibodies described herein, replenishment of healthy hemopoietic stem cells is stimulated by increasing availability of nutrients and space in the bone marrow compartment for their growth, survival and differentiation into downstream CLEC12A positive and CLEC12A negative, healthy cells, such as basophil, neutrophil, eosinophil and monocyte blood cells.

The subject is preferably a subject that is diagnosed to have acute myeloid leukaemia (AML), myelodysplastic syndrome (MDS), myelofibrosis or myeloproliferative neoplasm blast phase (MPN-BP).

Also provided is a method of preparing an autologous bone marrow cell graft for a subject that is being treated for a CLEC12A positive cancer, the method comprising incubating a bone marrow cell preparation of said subject with a bispecific antibody that binds CD3 and CLEC12A under conditions suitable for killing of CLEC12A positive cells and subsequently collecting bone marrow cells from said incubation.

The invention further provides a method of treating a CLEC12A positive cancer in a subject, the method comprising incubating a bone marrow cell preparation of said subject with a bispecific antibody that binds CD3 and CLEC12A under conditions suitable for killing of CLEC12A positive cells, treating the subject with an hemopoietic system ablative therapy and providing said subject with a bone marrow cell graft comprising said incubated bone marrow cells.

Further provided is a method of providing a subject with a hemopoietic stem cell sparing cancer treatment the method comprising administering a bispecific antibody that binds CD3 and CLEC12A to the subject in need thereof. The subject preferably has a CLEC12A positive cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1A:
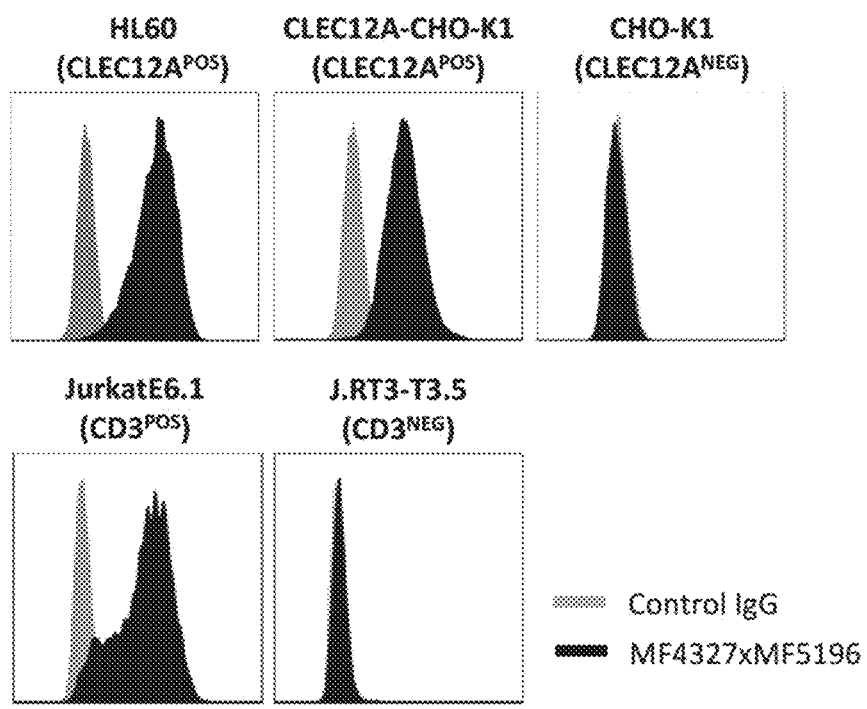
FIG. 1. CLEC12AxCD3 bispecific antibodies specifically bind to CLEC12A$^{POS}$ and CD3$^{POS}$ target cells. (A) Binding of a CLEC12AxCD3 bispecific antibody to CLEC12A and CD3 was determined on a panel of tumour cell lines by flow cytometry. HL60: CLEC12A$^{POS}$ promyelogenous cell line; CLEC12A-CHO-K1: CHO-K1 cell line stably expressing human CLEC12A (validated with reference anti-CLEC12A antibody, data not shown); CHO-K1: CLEC12A$^{NEG}$ parental CHO-K1 cell line; Jurkat E6.1: CD3$^{POS}$ T cell line; J.RT-T3.5: CD3$^{NEG}$ T cell line. (B) A CLEC12AxCD3 bispecific antibody binding profile in normal peripheral blood by flow cytometry. Gating strategy for analysed subsets were CD4 T cells: CD4$^{POS}$; CD8 T cells: CD8$^{POS}$; NK cells: CD3$^{NEG}$CD56$^{POS}$; NKT cells: CD3$^{POS}$CD56$^{POS}$; B cells: CD19$^{POS}$; myeloid dendritic cells (DC): BDCA1$^{POS}$CD19$^{NEG}$; granulocytes: based on SSC-FSC; monocytes: CD14$^{POS}$CD33$^{POS}$. (C) A CLEC12AxCD3 bispecific antibody binding within CD34$^{POS}$ progenitor compartment in normal bone marrow by flow cytometry. HSC: hemopoietic stem cell; MPP: multipotent progenitor; CMP: common myeloid progenitor; GMP: granulocyte-macrophage progenitor; MEP: megakaryocyte-erythroid progenitor; CLP: common lymphoid progenitor. Data shown for antibody MF4327 and MF5196 and isotype control IgG formatted with the final Fc format (silenced Fc effector function).

(A-C) Healthy donor-derived PBMC samples were co-cultured with antibody MF4327xMF5196 or MockxCD3 antibody at the indicated concentration range and compared to the PBS condition. T cell activation (A), monocyte lysis by autologous T cells (B) and B cell lysis (C) were assessed after 48 hours using flow cytometry. (D) Monocytes derived from healthy donors were purified by negative selection and co-cultured with CFSE-labelled resting autologous T cells at an E:T ratio of 5:1 with antibody MF4327xMF5196 and MockxCD3 antibody at 1,000 ng/mL (anti-CD3 IgG was formatted with WT Fc effector function) for 5 days. T cell proliferation was demonstrated by the reduction of CFSE-positive T cells. (E) Healthy donor-derived PBMCs were cultured with 1,000 ng/mL antibody MF4327xMF5196, MockxCD3 or anti-CD3 (CD3) antibody for 48 hours. Subsequently, supernatant was harvested to measure the human cytokine levels in these supernatants using a human 10-plex Luminex setup. Cytokine levels were detectable for the six cytokines shown. Data shown in A-D are from a single donor and are representative of 4 independent donors from multiple independent experiments. Data shown in E are from two representative healthy PBMC donors, with duplicates for each donor, whereby PBMCs from 8 healthy donors were tested.

FIG. 4. antibody MF4327xMF5196 spares the potential of normal bone marrow progenitor cells to develop the complete myeloid and erythroid lineage. CD34$^{POS}$ hemopoietic progenitor cells from healthy donor bone marrow were co-cultured with autologous pre-activated T cells in the presence of 200 ng/mL antibody MF4327xMF5196 or MockxCD3 at an E:T ratio of 10:1 for 16 hours. A) Using a quantified flow cytometry setup, antibody MF4327xMF5196-induced lysis was determined relative to non-IgG condition for the indicated cell fractions. Each data point represents the mean value for an independent bone marrow donor tested in triplicate (n=4). Gating strategy is described in FIG. 10. B) Analyses of the impact of antibody MF4327xMF5196 on different CD34$^{POS}$ bone marrow populations after 16 hour cytotoxicity assay, showing absolute number for three donors. Gating of CD34$^{POS}$ progenitor cells is depicted in FIG. 11. Quantification of absolute number in the different test conditions was calculated by integration of the frequency and absolute count of total CD34$^{POS}$ cells determined with flow count fluorospheres. Data show mean of duplicate measurement. C) Scatter plots showing impact of antibody MF4327xMF5196 on CLEC12A- and/or CD123-expressing subsets after 16 hours cytotoxicity assay for indicated conditions, gated on CD34$^{POS}$LIN$^{NEG}$ cells. One representative donor out of two shown. D) Capacity of CD34$^{POS}$ cells upon 16 hours cytotoxicity assay with antibody MF4327xMF5196 to give rise to granulocyte-macrophage colonies (CFU-GM), burst-forming units-erythrocyte (BFU-E) and megakaryocyte colonies (CFU-Mk) was quantified after two weeks culture in semi-solid medium, from four different donors. Control cultures are either non-IgG treated co-cultures or CD34$^{POS}$ cells seeded alone. Each data point represents the mean value of triplicate cultures (CFU-GM and BFU-E) or quadruplicates (CFU-Mk) per donor. E) Flow cytometric analysis of CD15$^{POS}$CD33$^{POS}$ and CD14$^{POS}$CD36$^{POS}$CD33$^{POS}$ cell content of the two week MethoCult cultures described in D. Data show the frequency of monocytic and myelocytic cells out of total CD33$^{POS}$ cells for three different donors. HSC: hemopoietic stem cell; MPP: multipotent progenitor; CMP: common myeloid progenitor; GMP: granulocyte-macrophage progenitor; MEP: megakaryocyte-erythroid progenitor; CLP: common lymphoid progenitor. Statistical analysis was performed using paired student's t test. *p<0.05, p<0.01, *p<0.001.

FIG. 5. antibody MF4327xMF5196 efficiently induces redirected lysis of CLEC12A$^{POS}$ primary AML blasts by autologous T cells Resting CD3$^{POS}$ T cells isolated from the peripheral blood of AML patients in clinical remission were co-cultured for 48 hours with CFSE-labelled CLEC12A$^{POS}$ autologous primary AML blasts collected at AML diagnosis. The E:T ratio was 5:1 and IgGs were added at a concentration of 1,000 ng/mL: antibody MF4327xMF5196, MockxCD3 or control IgG (all with WT Fc effector function). The extent of AML blast lysis induced by each IgG relative to the PBS condition was quantified using flow cytometry. (A) Diagram showing stage of AML at which the AML blast samples and autologous T cells were obtained. (B) Expression of CLEC12A antigen on primary AML blast samples (AML blast defined as CD45$^{+/-}$SSC$^{+/-}$). The histograms show anti-CLEC12A IgG binding for each patient sample, with lymphocytes indicated in grey and AML blasts in black. The gate for CLEC12A positivity was set based on the CLEC12A-negative lymphocyte fraction; percentage CLEC12A positive blasts is given. (C-D) Activation status of AML patient CD4$^{POS}$ (C) and CD8$^{POS}$ T cells (D). (E) Cytotoxicity of CLEC12A$^{POS}$ primary AML blasts mediated by autologous primary T cells when incubated with indicated IgG (relative to PBS). The data shown are mean±SE of three AML patient samples (patients 7-9, see Table III) tested in triplicate. Data were analysed by ANOVA relative to PBS:  P<0.01, * P<0.001.

Figure 6:
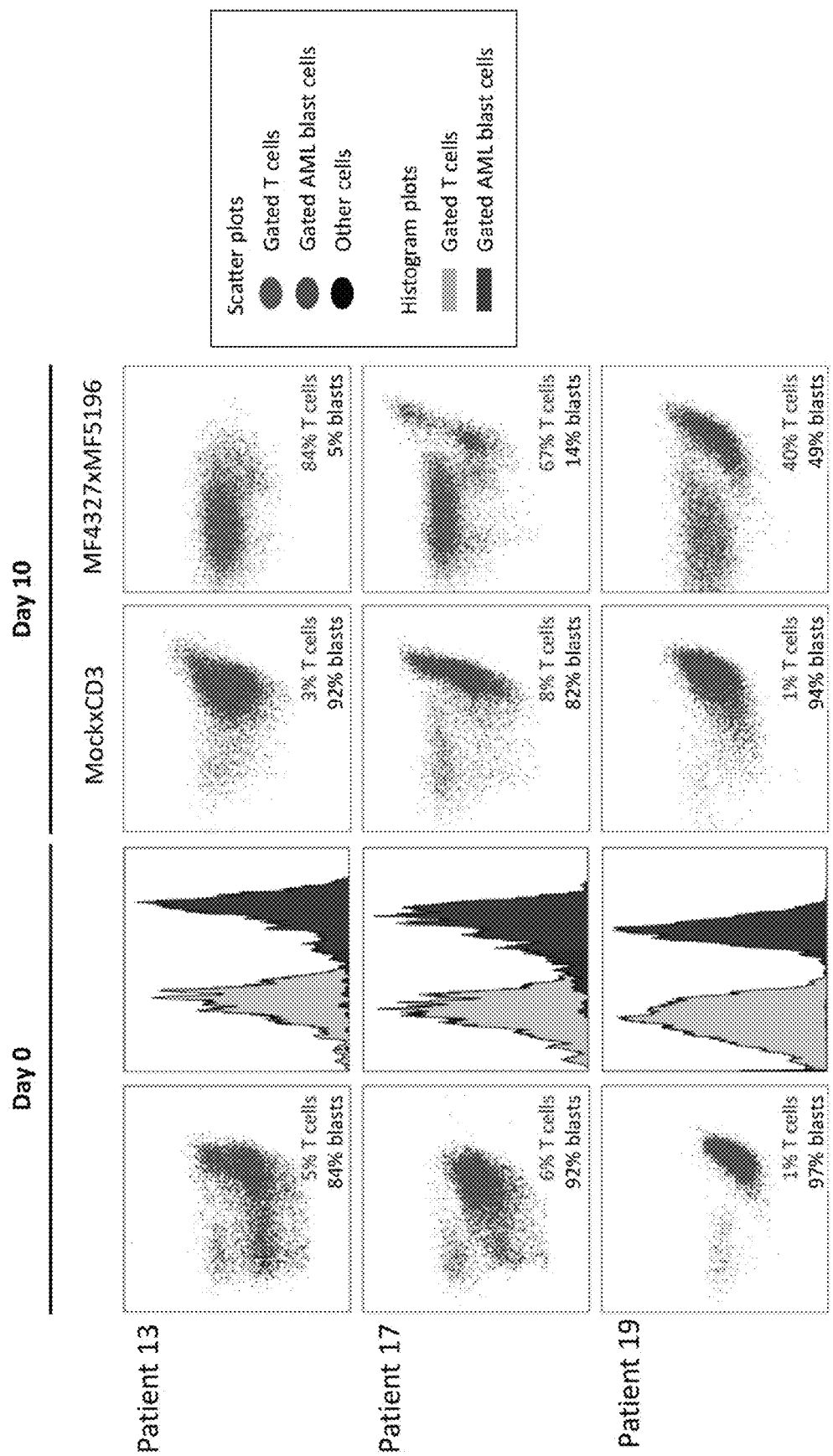

FIG. 6. antibody MF4327xMF5196 induces AML blast killing in primary AML samples

Primary AML patient samples taken at AML diagnosis were cultured for 10 days in medium supplemented with a cytokine cocktail to support AML blast survival. antibody MF4327xMF5196 or MockxCD3 antibodies were added at 200 ng/mL. For each patient, the CD45xCD33 plots show; the live gate for day 0 and for each IgG at day 10. The T cells are shown in red, the AML blasts in blue (defined as CD45$^{+/-}$SSC$^{+/-}$), with the percentages of T cells and AML blasts indicated. Histograms at day 0 show for each patient the CLEC12A expression levels of AML blast cells. Staining using an anti-CLEC12A antibody is shown in black and staining using an isotype control antibody is shown in grey.

Figure 7:
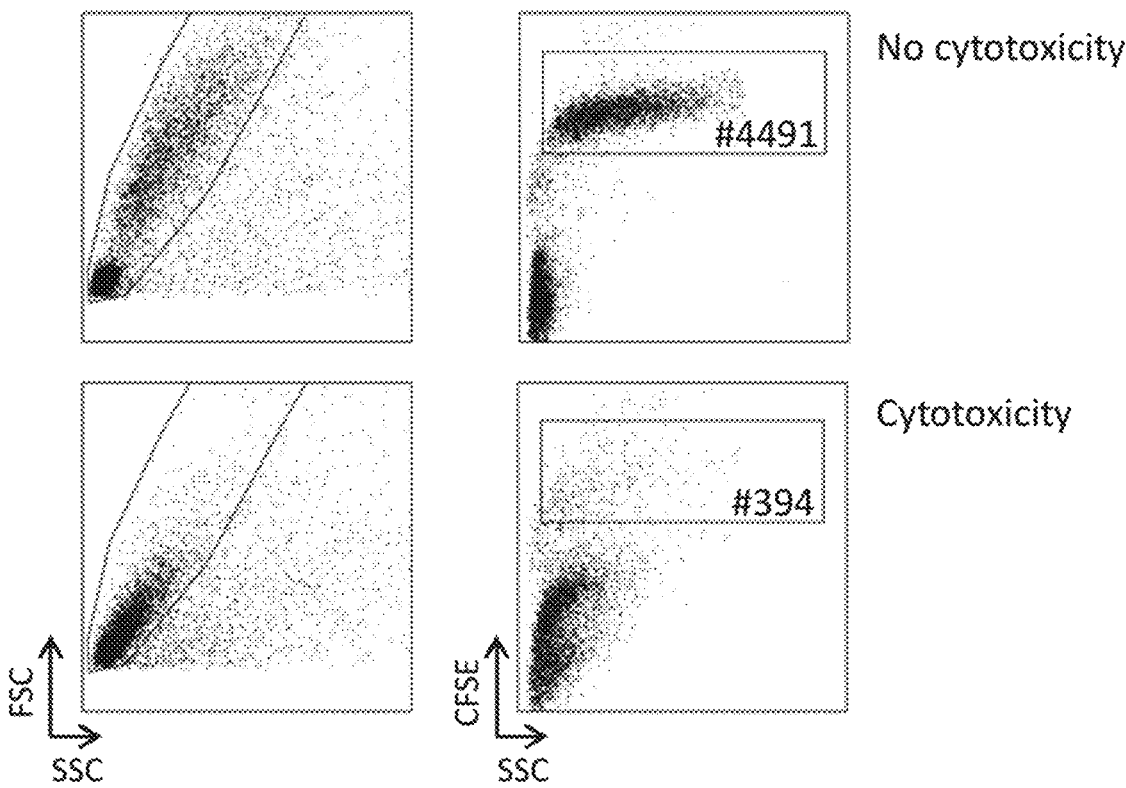

FIG. 7. Gating strategy used to quantify HL60 target cell lysis by flow cytometry. A fixed volume of cells was measured by flow cytometry. Live cells were gated based on the FSC-SSC profile (left-hand plots). Within the live gate, the CFSE$^{POS}$ HL60 cells were then gated (right-hand plots). Absolute numbers of CFSE$^{POS}$ live HL60 target cells within that gate were used to calculate the percentage of HL60 target cell lysis as described in the materials and methods section. Upper plots show a PBS condition with no cytotoxicity, while lower plots show an antibody MF4327xMF5196 condition in which HL60 cytotoxicity was observed.

Figure 8:
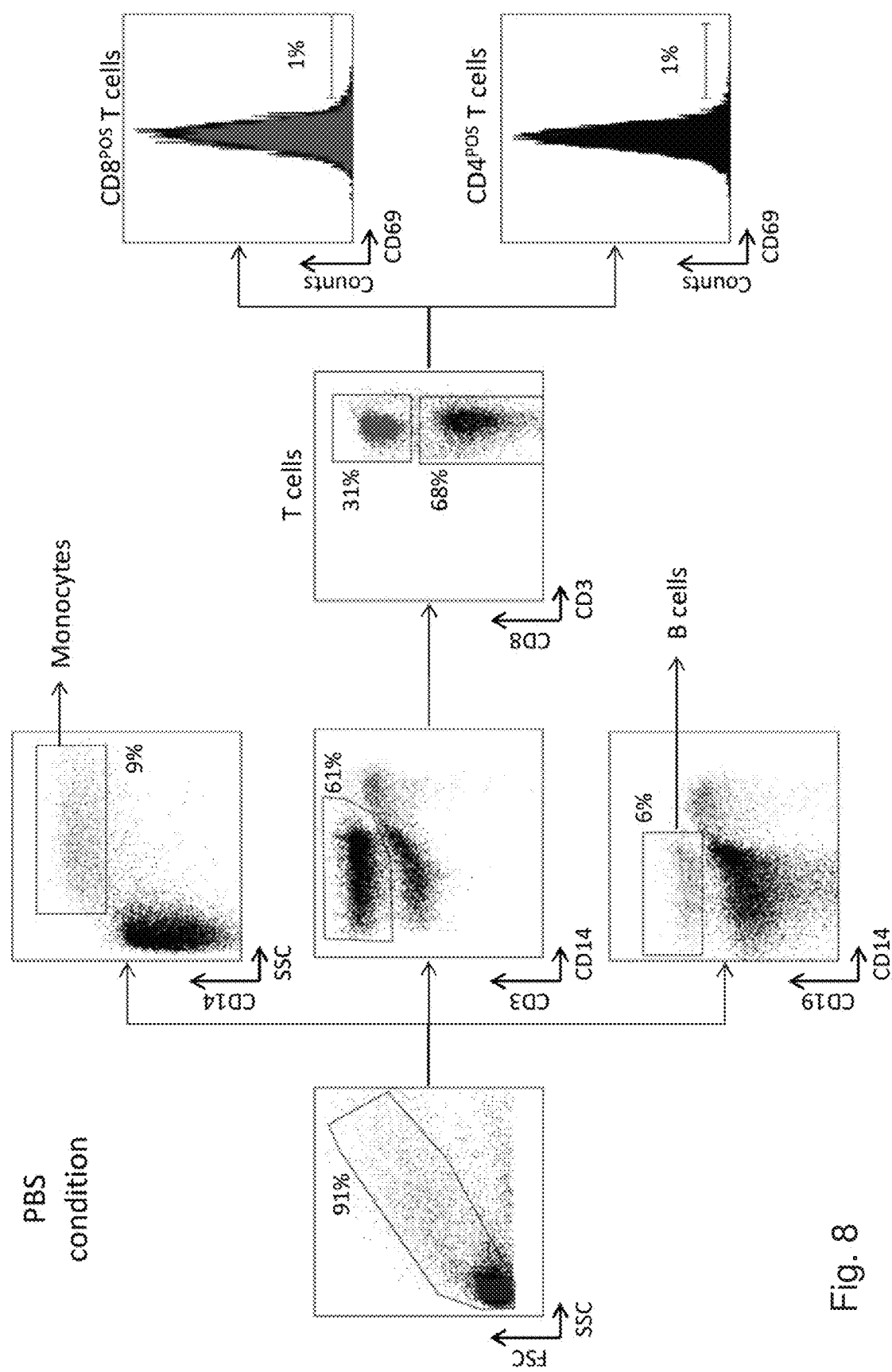

FIG. 8. Gating strategy used to quantify cytotoxicity in PBMC-based monocyte cytotoxicity assay. Monocytes (CD14$^{POS}$), CD4 (CD4$^{POS}$CD3$^{POS}$) and CD8 (CD8$^{POS}$CD3$^{POS}$) T cells, and B cells (CD19$^{POS}$) were gated out as shown. The absolute number of monocytes and B cells measured in a fixed volume of assay medium was quantified and used for calculating the percentage of cytotoxicity induced by the test IgG condition (lower panel) relative to the PBS control condition (upper panel) as described in the materials and methods section. CD4$^{POS}$ and CD8$^{POS}$ T cell subsets were identified within the T cell population, and their activation status was determined using the activation marker CD69, relative to the PBS control condition.

Figure 9:
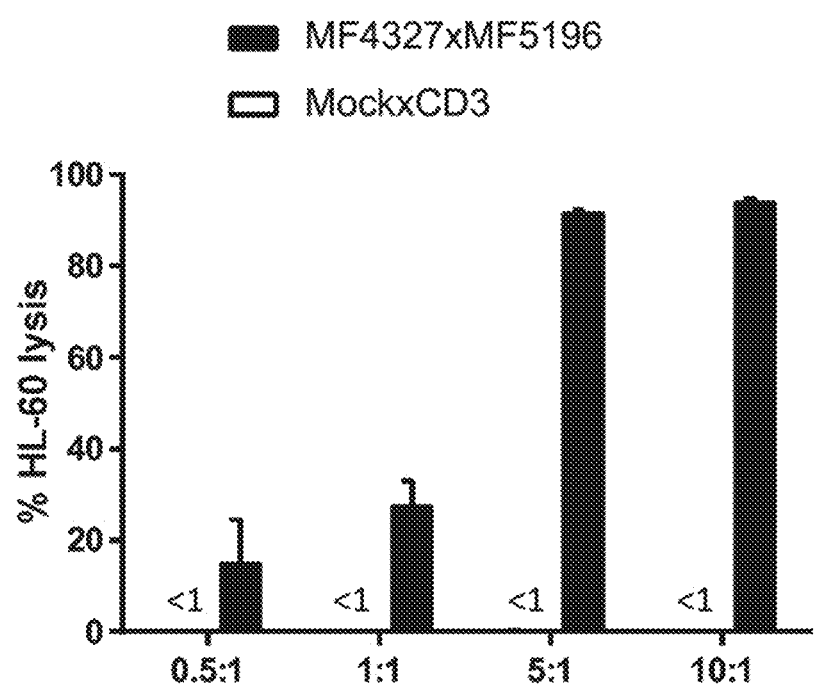

FIG. 9. Activity of antibody MF4327xMF5196 bispecific IgG is E:T ratio-dependent Healthy donor-derived resting T cells were co-cultured with CFSE-labelled HL60 cells in the presence of antibody MF4327xMF5196, MockxCD3 or control IgG. The effect of increasing E:T ratios on HL60 target cell lysis at 1,000 ng/mL IgG was determined after 48 hours of co-culture.

Figure 10A:
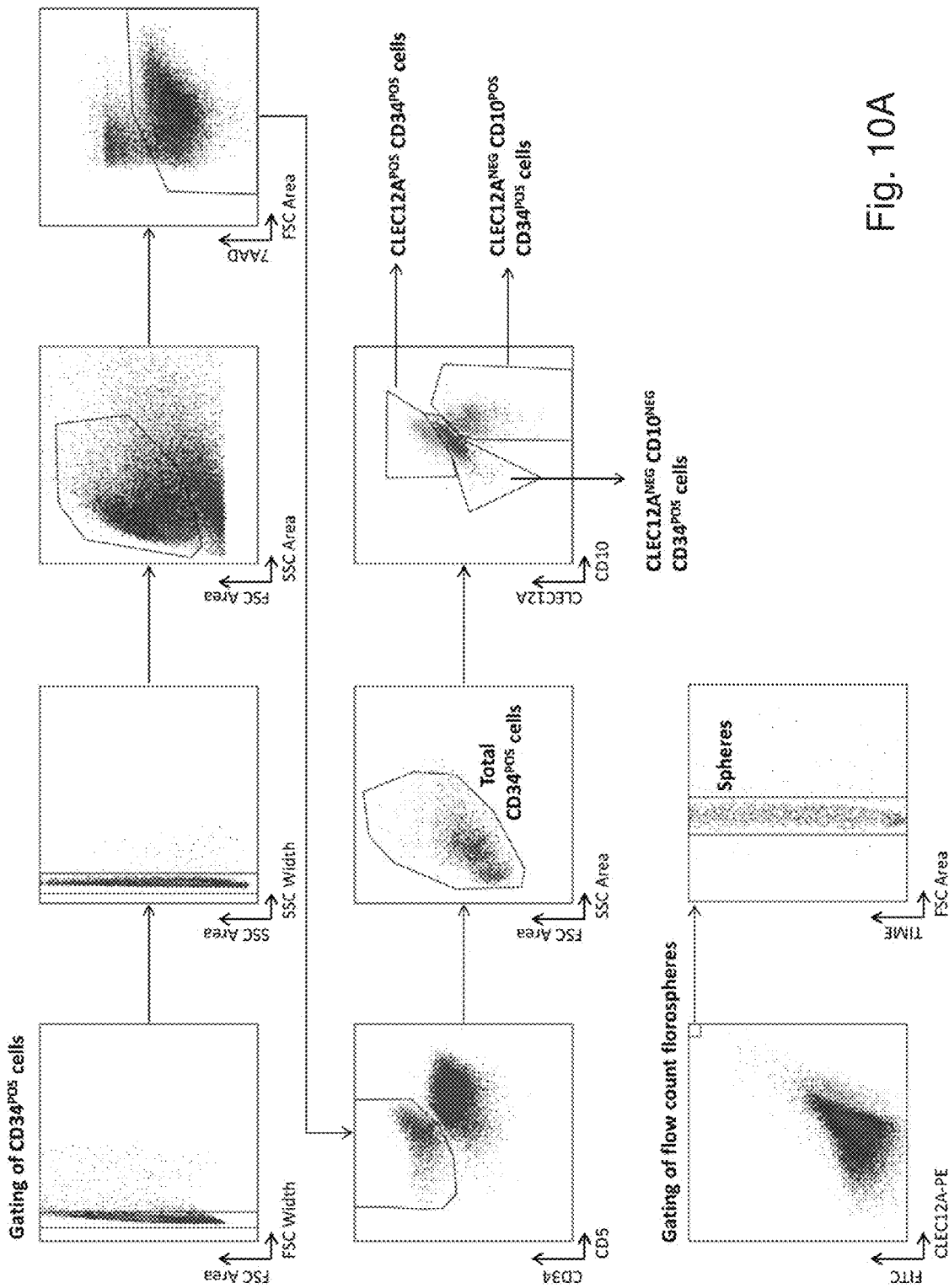
Figure 10B:
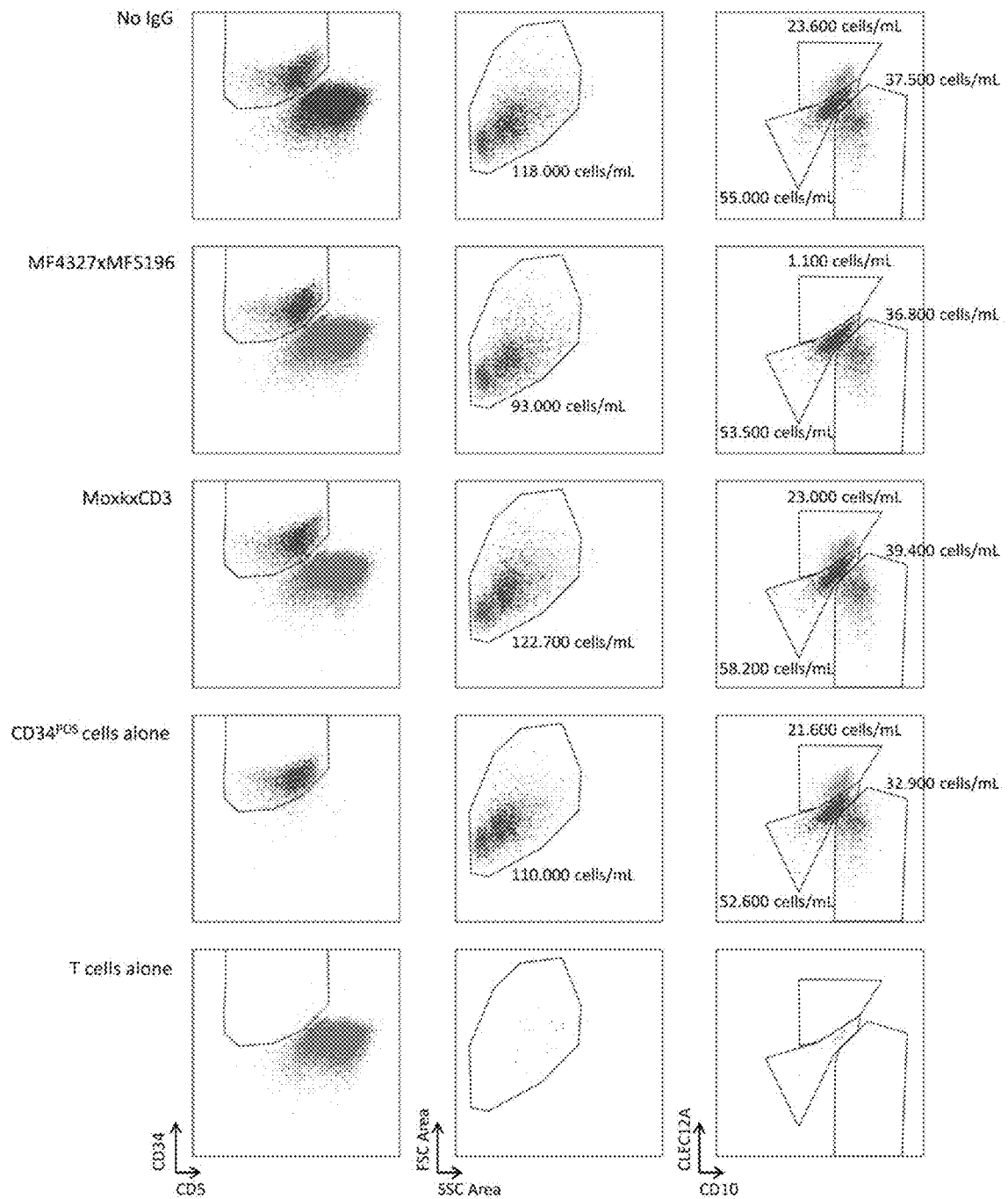
Figure 11:
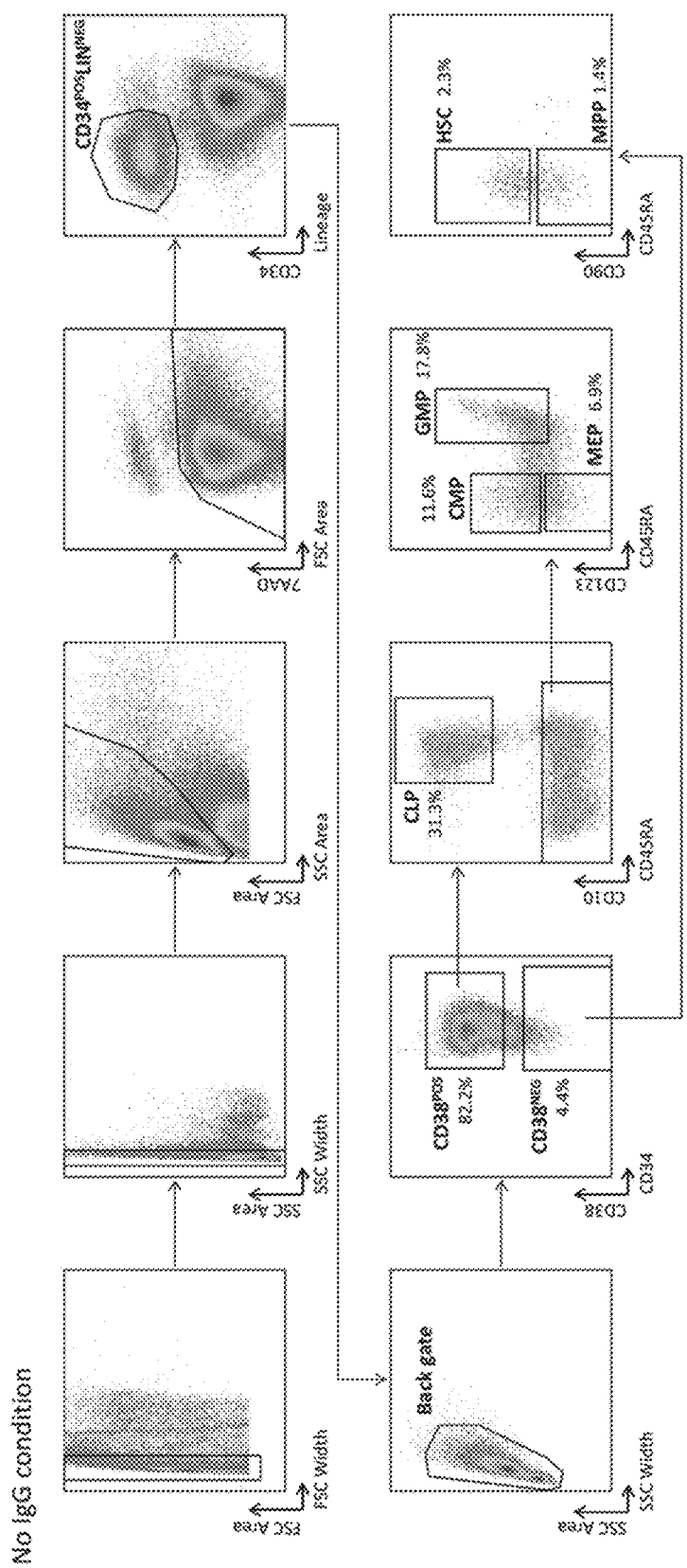

FIG. 10. Gating strategy used to quantify recovery of healthy donor bone marrow CD34$^{POS}$ progenitor cells. A) Total CD34$^{POS}$ cells, CLEC12A$^{POS}$, CLEC12A$^{NEG}$CD10$^{NEG}$ and CLEC12A$^{NEG}$CD10$^{NEG}$ cells were gated as is shown. First single cells were gated based on FSC and SSC area and width, and then live cells were defined based on FSC-SSC profile and 7AAD negativity. Within live cells, CD34$^{POS}$ cells were gated from the co-cultured T cells using CD34 and CD5. Within total CD34$^{POS}$ cells, cells were divided into three populations based on CLEC12A and CD10 expression. For quantification of the CD34$^{POS}$ populations, a fixed volume of flow count fluorospheres of known concentration was added to each sample before acquisition. The absolute number of cells per mL was calculated based on the ratio of fluorospheres and cells. B) Scatter plots showing the different CD34$^{POS}$ populations in all test conditions of one representative donor.

FIG. 11. Gating strategy used to determine identity and relative ratio of different CD34$^{POS}$ progenitor cells. First single cells were gated based on FSC and SSC area and width, and then live cells were defined based on FSC-SSC profile and 7AAD negativity. Within live cells, lineage negative CD34$^{POS}$ cells were gated, followed by a FSC-SSC back gate. Cells were subsequently divided into CD38$^{POS}$ and CD38$^{NEG}$ compartments. Within the CD34$^{POS}$CD38$^{POS}$ compartment, CLPs were gated on based on CD10 expression. Cells lacking CD10 expression were further separated into CMP, MEP and GMP based on CD123 and CD45RA expression. For some donors, CD135 was used instead of CD123 for defining these three populations. Within the CD34$^{POS}$CD38$^{NEG}$ compartment, HSC and MPP were defined according to CD90 and CD45RA expression. Gates were confirmed with fluorescence-minus one controls. HSC: hemopoietic stem cell; MPP: multipotent progenitor; CMP: common myeloid progenitor; GMP: granulocyte-macrophage progenitor; MEP: megakaryocyte-erythroid progenitor; CLP: common lymphoid progenitor.

Figure 12:
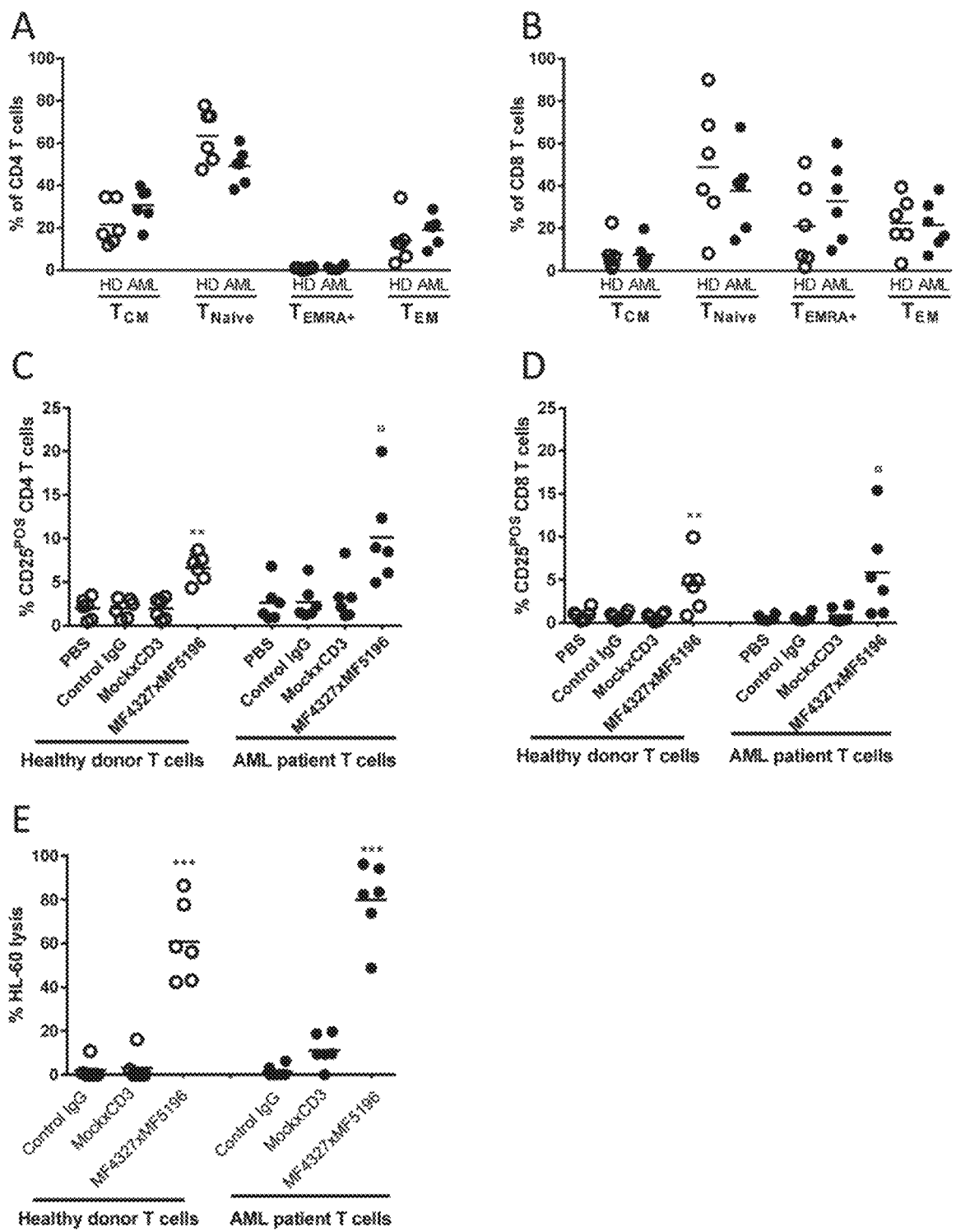

FIG. 12. antibody MF4327xMF5196 redirects AML patient T cells and healthy donor T cells to specifically lyse CLEC12A$^{POS}$ AML cell line with equal efficiency. Resting CD3$^{POS}$ T cells were isolated from the peripheral blood of six healthy donors or six AML patients in clinical remission (patients 1-6; see Table III for patient characteristics). Isolated T cells were co-cultured with CFSE-labelled HL60 target cells at an E:T ratio of 5:1 for 48 hours in the presence of 1,000 ng/mL antibody MF4327xMF5196, MockxCD3 IgG or control IgG (all with WT Fc effector function). (A-B) Flow cytometry to analyse the subset composition of the CD4$^{POS}$ T cells (A) and CD8$^{POS}$ T cells (B) within the CD3$^{POS}$ fraction of T cells taken from healthy donors (HD) or AML patients subsequently used for HL60 target cell lysis. T$_{CM}$: central memory T cells; T$_{Naïve}$: naïve T cells; T$_{EMRA+}$: effector-memory cells with reacquired CD45RA; T$_{EM}$: effector memory T cells. (C-E) Activation of CD4$^{POS}$ T cells (C) and CD8$^{POS}$ T cells (D) as well as HL60 target cell lysis (E) analysed by flow cytometry and compared to PBS condition for indicated IgGs and T cell sources. Each circle represents the mean value for a single T cell donor tested in triplicate. Data were analysed relative to PBS by ANOVA:* P<0.05,  P<0.01, * P<0.001.

Figure 13:
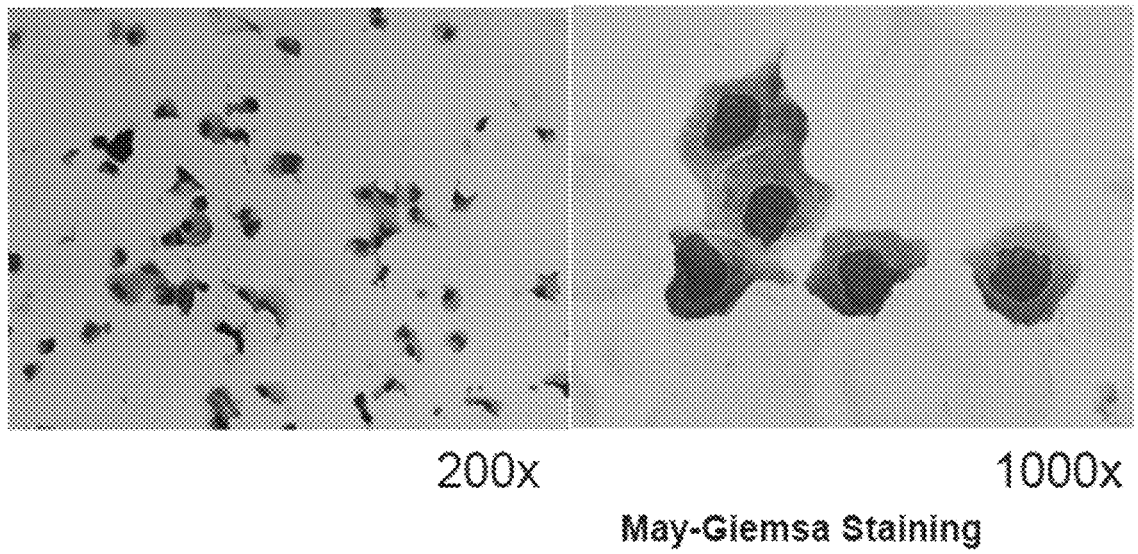

FIG. 13. Morphology and JAK2V617F Mutational Status of Cells Generated in Secondary Plating of $SSC^{low}CD45^{dim}CD34^+CD38^-CLEC12A^{+/-}$ Cells. May-Giemsa staining of re-plated CLEC12A positive cells, individual colonies were picked and tested for the JAK2 driver mutation.

Figure 14A:
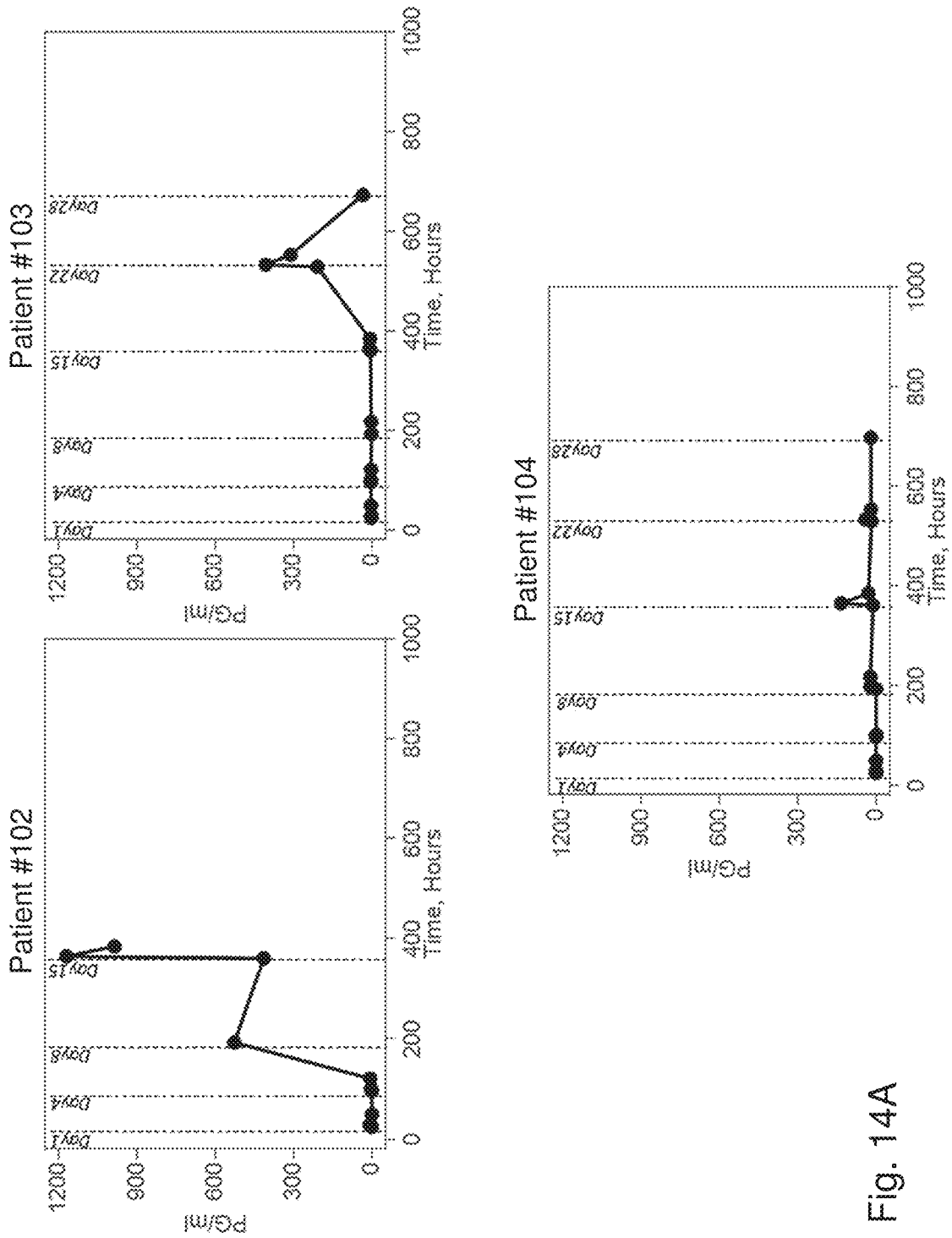

FIG. 14a. IL-6 levels of patients treated with antibody MF4327xMF5196. In PG/ml, measured before dosing, 4 hours and 24 hours after the end of infusion. Dosing took place on day 1, day 4, day 8, and day 22. The patients received a priming dose of 1 mg on day 1, followed by step-up doses of 3 mg on day 4 and 15 mg on day 8, and a full dose of 25 mg on day 15. Cytokine levels were also determined at the end of a treatment cycle (day 28).

Figure 14B:
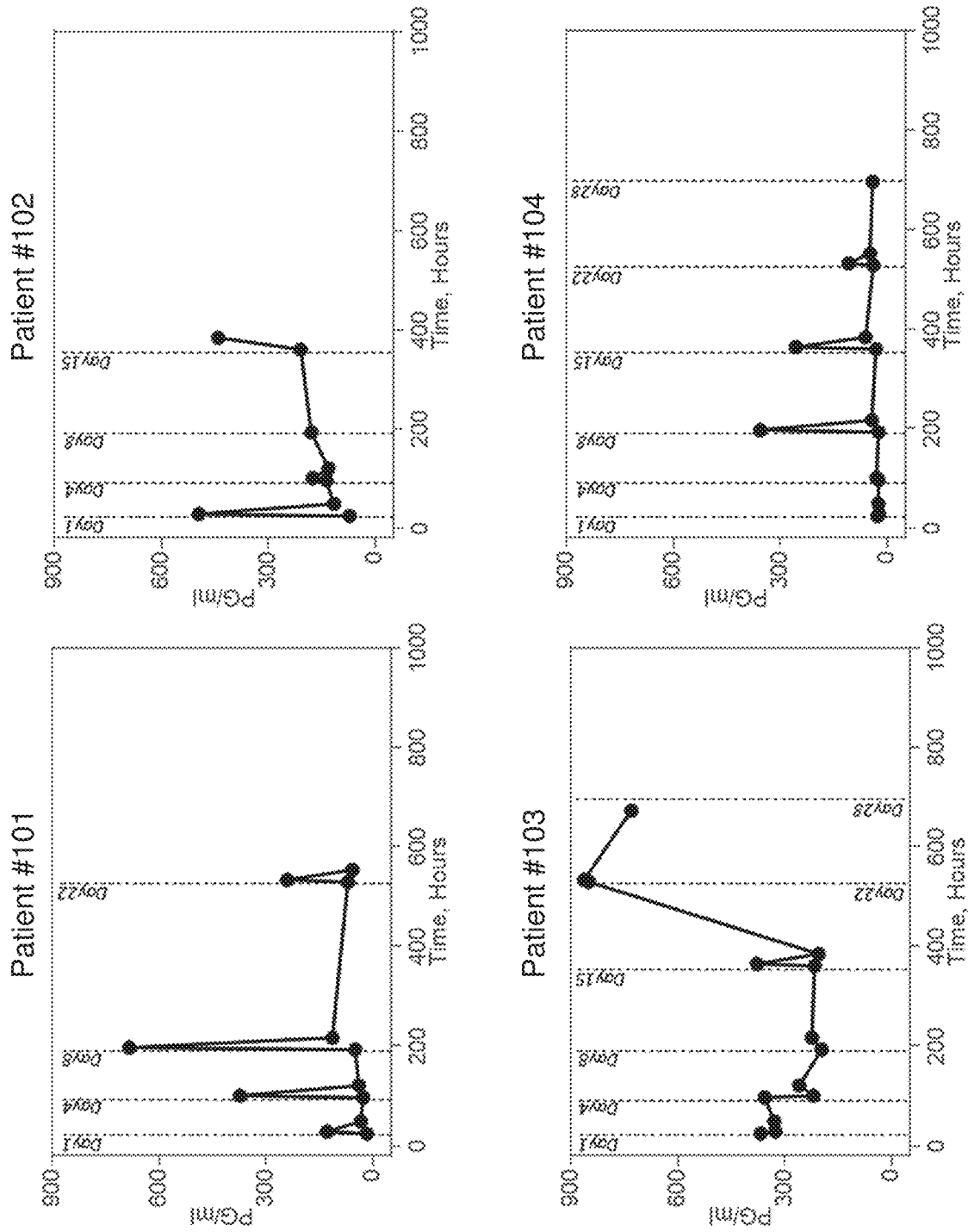

FIG. 14b. IL-8 levels of patients treated with antibody MF4327xMF5196. In PG/ml, measured before dosing, 4 hours and 24 hours after the end of infusion. Dosing took place on day 1, day 4, day 8, and day 22. The patients received a priming dose of 1 mg on day 1, followed by step-up doses of 3 mg on day 4 and 15 mg on day 8, and a full dose of 25 mg on day 15. Cytokine levels were also determined at the end of a treatment cycle (day 28).

Figure 14C:
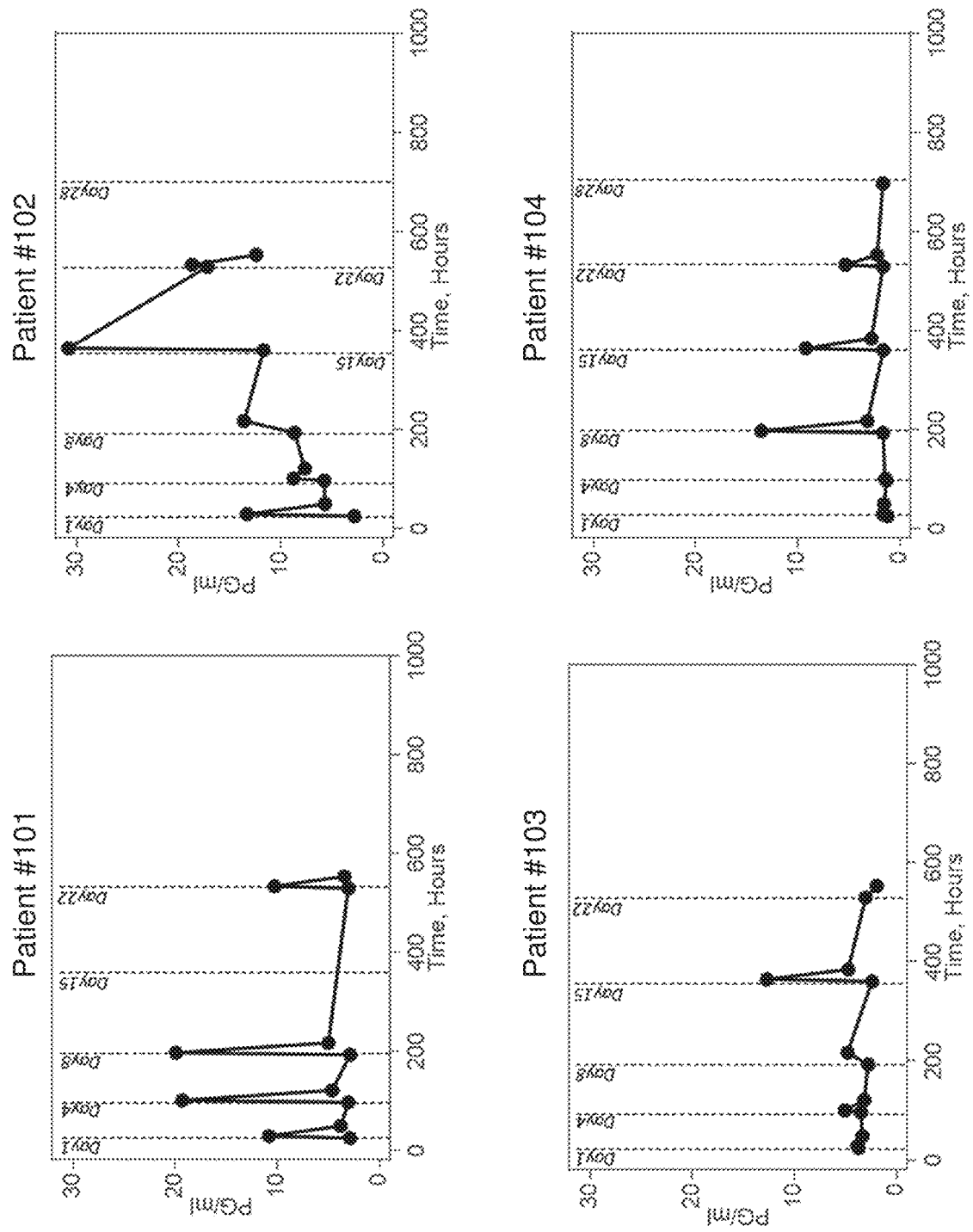

FIG. 14c. TNFα levels of patients treated with antibody MF4327xMF5196. In PG/ml, measured before dosing, 4 hours and 24 hours after the end of infusion. Dosing took place on day 1, day 4, day 8, and day 22. The patients received a priming dose of 1 mg on day 1, followed by step-up doses of 3 mg on day 4 and 15 mg on day 8, and a full dose of 25 mg on day 15. Cytokine levels were also determined at the end of a treatment cycle (day 28).

Figure 14D:
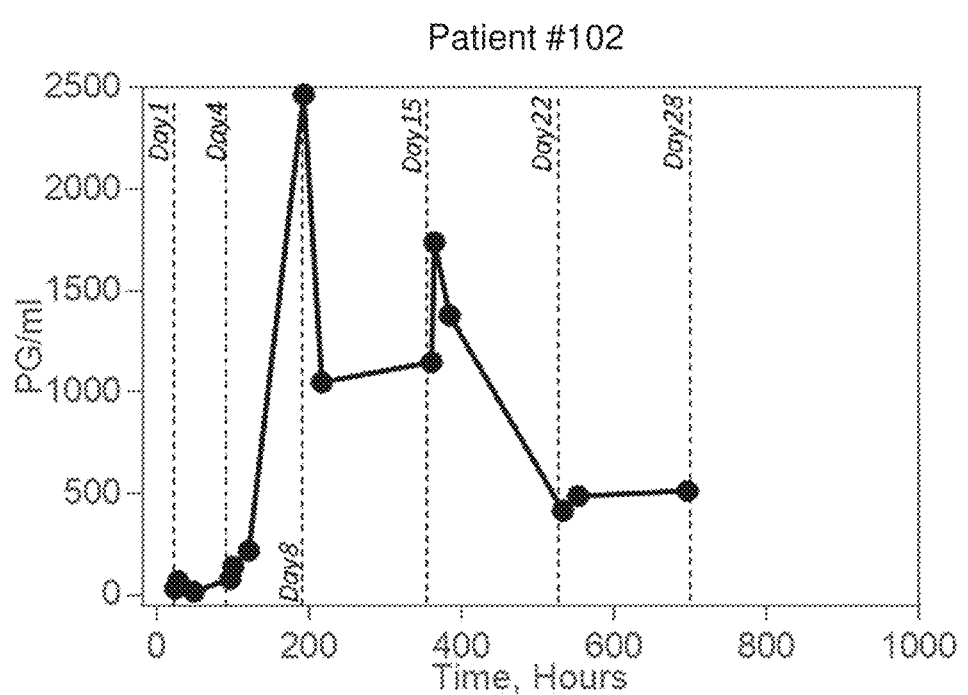

FIG. 14d. IFNγ levels of patient treated with antibody MF4327xMF5196. In PG/ml, measured before dosing, 4 hours and 24 hours after the end of infusion. Dosing took place on day 1, day 4, day 8, and day 22. The patients received a priming dose of 1 mg on day 1, followed by step-up doses of 3 mg on day 4 and 15 mg on day 8, and a full dose of 25 mg on day 15. Cytokine levels were also determined at the end of a treatment cycle (day 28).

Figure 15A:
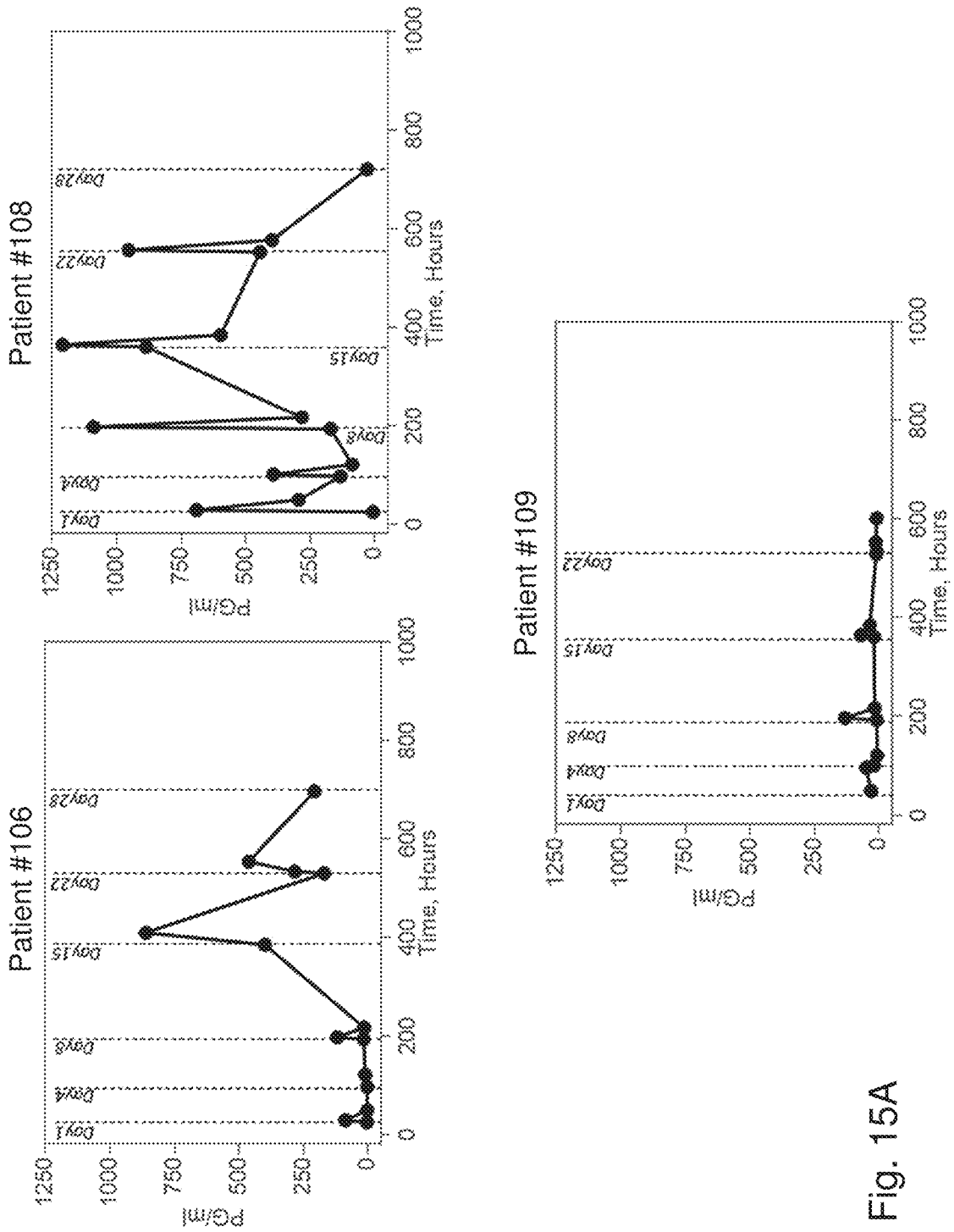

FIG. 15a. IL-6 levels of patients treated with antibody MF4327xMF5196. In PG/ml, measured before dosing, 4 hours and 24 hours after the end of infusion. Dosing took place on day 1, day 4, day 8, and day 22. The patients received a priming dose of 3 mg on day 1, followed by step-up doses of 10 mg on day 4 and 25 mg on day 8, and a full dose of 40 mg on day 15. Cytokine levels were also determined at the end of a treatment cycle (day 28).

Figure 15B:
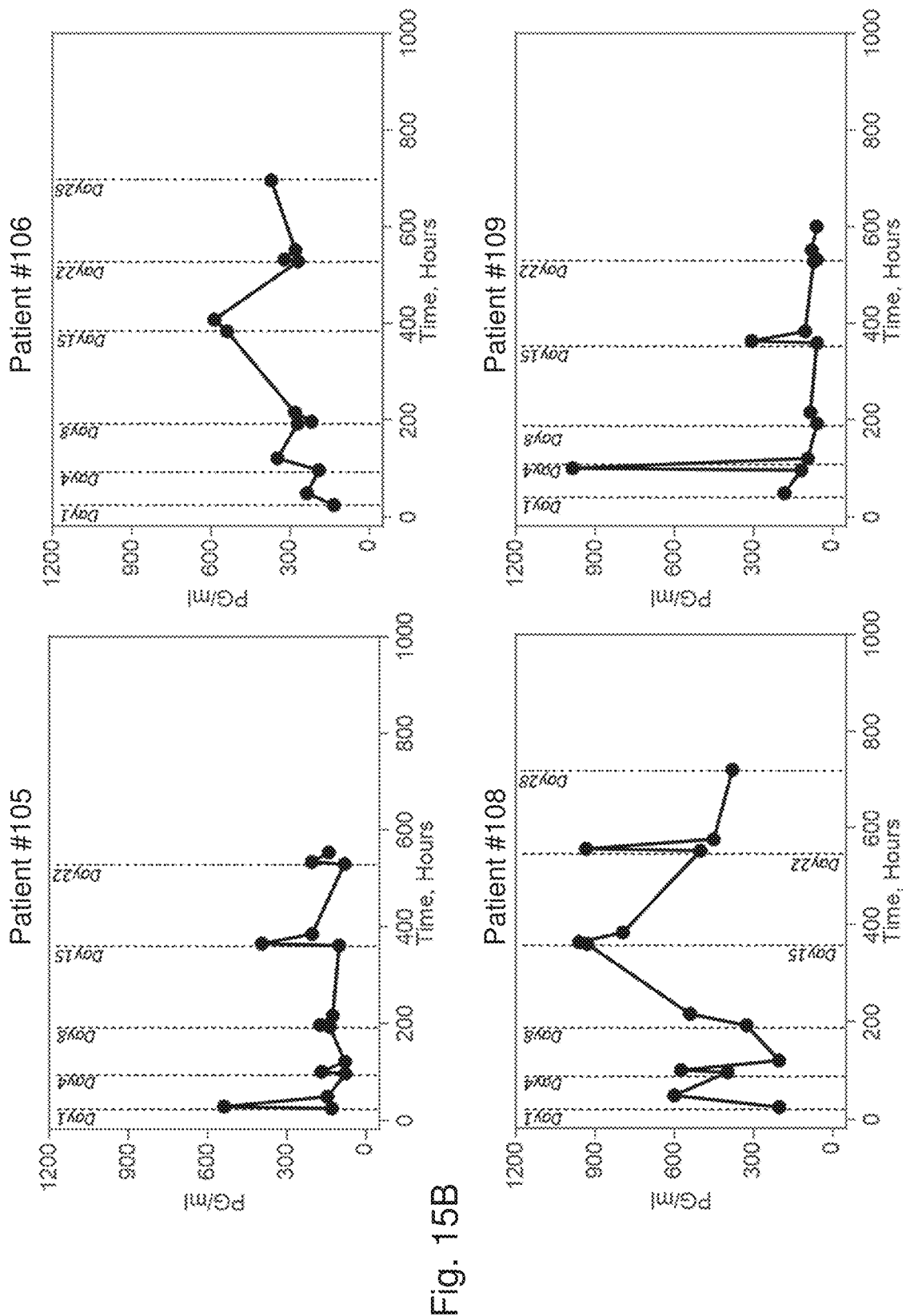

FIG. 15b. IL-8 levels of patients treated with antibody MF4327xMF5196. In PG/ml, measured before dosing, 4 hours and 24 hours after the end of infusion. Dosing took place on day 1, day 4, day 8, and day 22. The patients received a priming dose of 3 mg on day 1, followed by step-up doses of 10 mg on day 4 and 25 mg on day 8, and a full dose of 40 mg on day 15. Cytokine levels were also determined at the end of a treatment cycle (day 28).

Figure 15C:
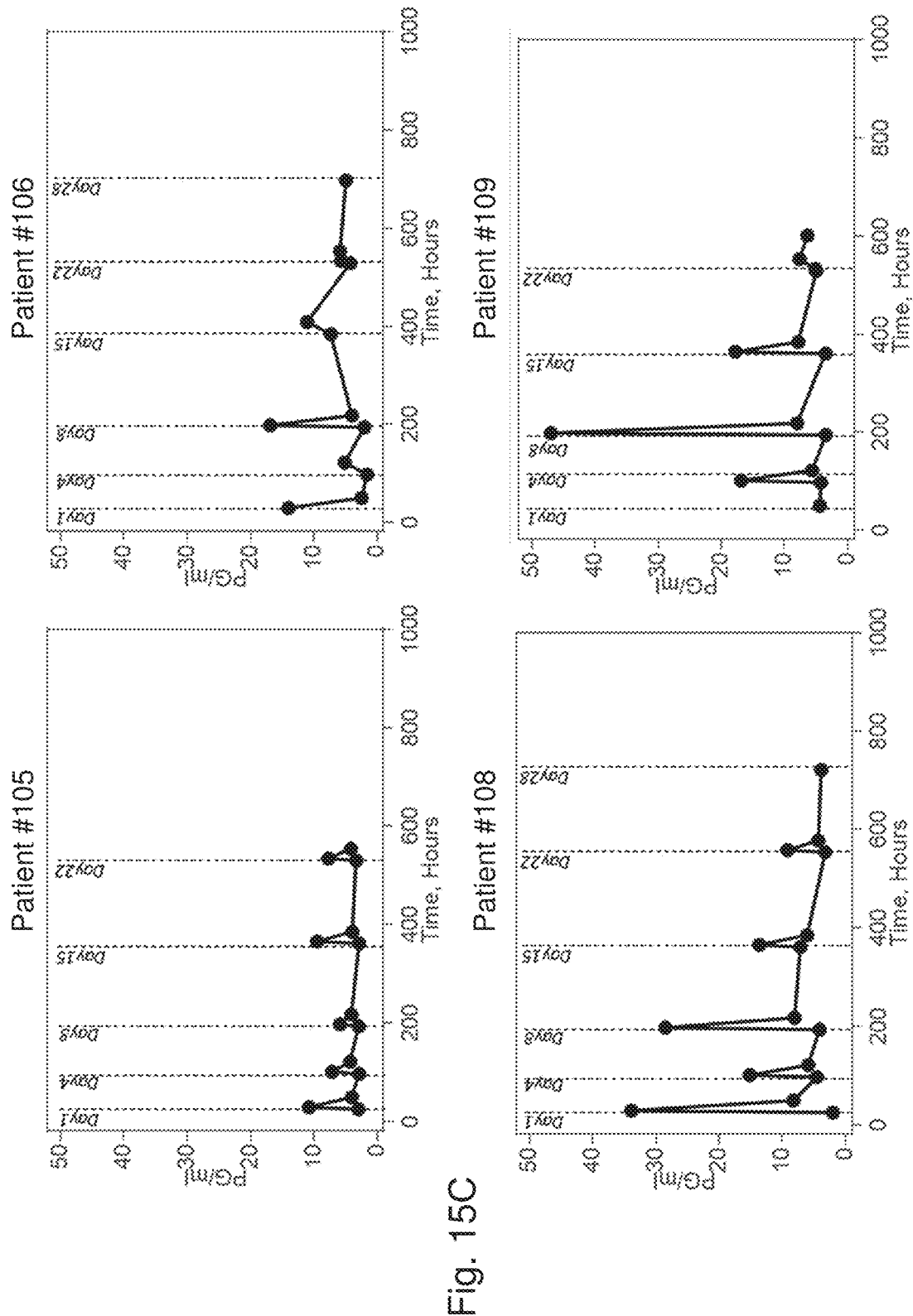

FIG. 15c. TNFα levels of patients treated with antibody MF4327xMF5196. In PG/ml, measured before dosing, 4 hours and 24 hours after the end of infusion. Dosing took place on day 1, day 4, day 8, and day 22. The patients received a priming dose of 3 mg on day 1, followed by step-up doses of 10 mg on day 4 and 25 mg on day 8, and a full dose of 40 mg on day 15. Cytokine levels were also determined at the end of a treatment cycle (day 28).

Figure 15D:
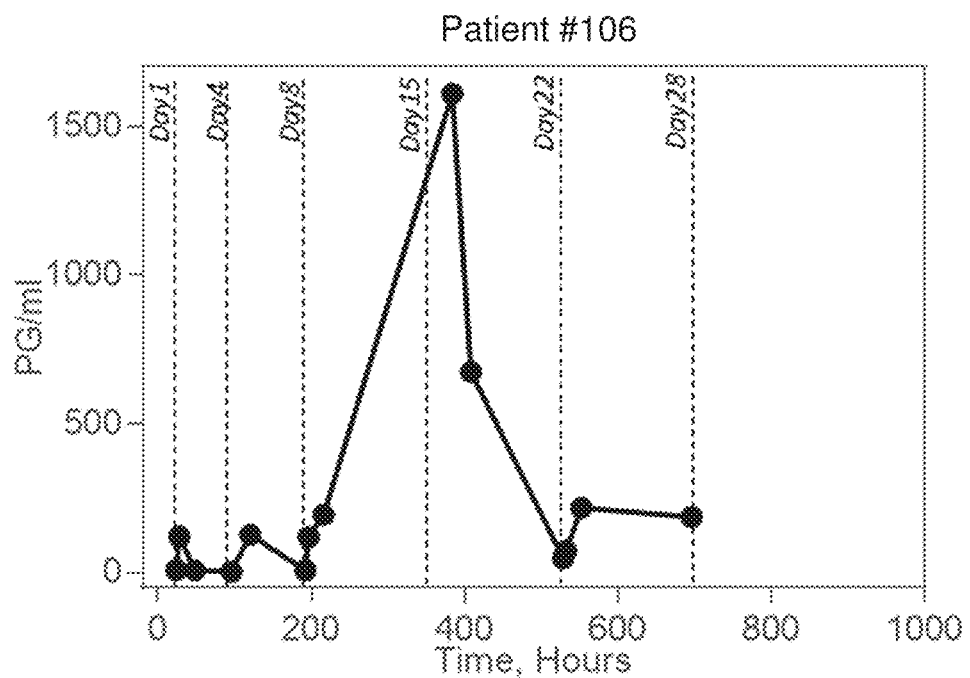

FIG. 15d. IFNγ levels of patient treated with antibody MF4327xMF5196. In PG/ml, measured before dosing, 4 hours and 24 hours after the end of infusion. Dosing took place on day 1, day 4, day 8, and day 22. The patients received a priming dose of 3 mg on day 1, followed by step-up doses of 10 mg on day 4 and 25 mg on day 8, and a full dose of 40 mg on day 15. Cytokine levels were also determined at the end of a treatment cycle (day 28).

Figure 16A:
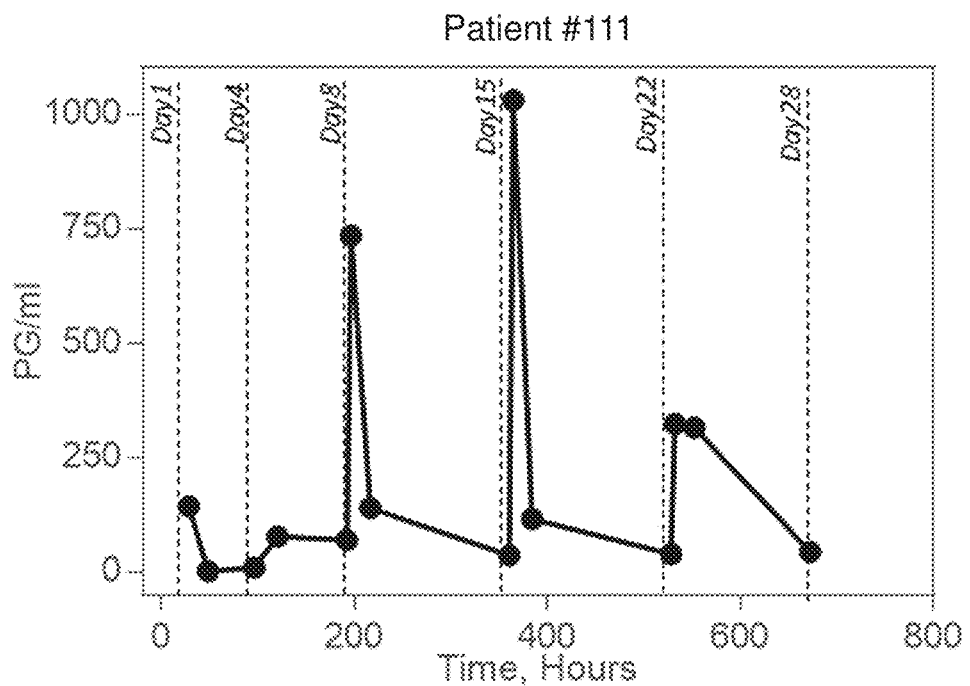

FIG. 16a. IL-6 levels of patient treated with antibody MF4327xMF5196. In PG/ml, measured before dosing, 4 hours and 24 hours after the end of infusion. Dosing took place on day 1, day 4, day 8, and day 22. The patients received a priming dose of 5 mg on day 1, followed by step-up doses of 15 mg on day 4 and 25 mg on day 8, and a full dose of 60 mg on day 15. Cytokine levels were also determined at the end of a treatment cycle (day 28).

Figure 16B:
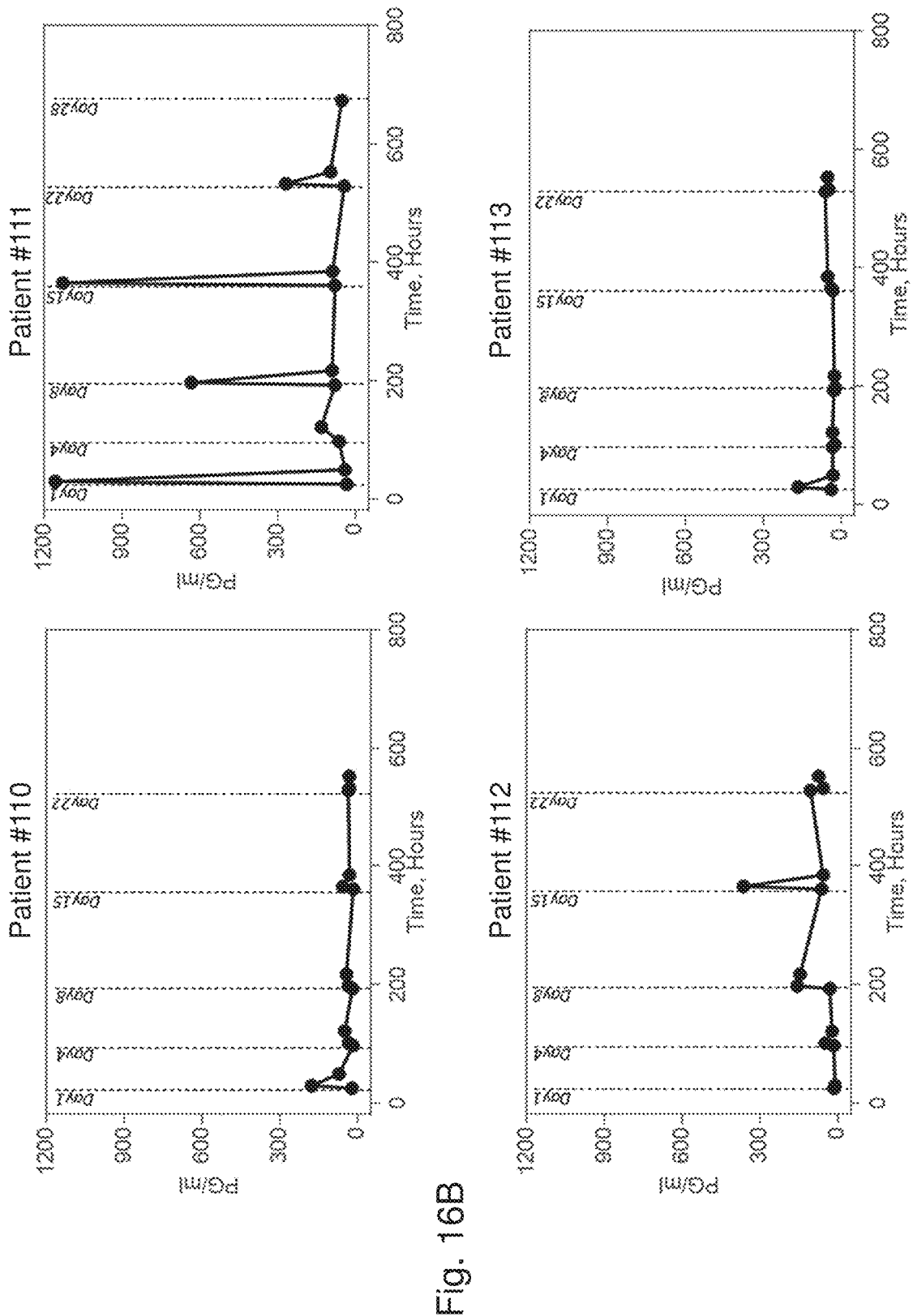

FIG. 16b. IL-8 levels of patients treated with antibody MF4327xMF5196. In PG/ml, measured before dosing, 4 hours and 24 hours after the end of infusion. Dosing took place on day 1, day 4, day 8, and day 22. The patients received a priming dose of 5 mg on day 1, followed by step-up doses of 15 mg on day 4 and 25 mg on day 8, and a full dose of 60 mg on day 15. Cytokine levels were also determined at the end of a treatment cycle (day 28).

Figure 16C:
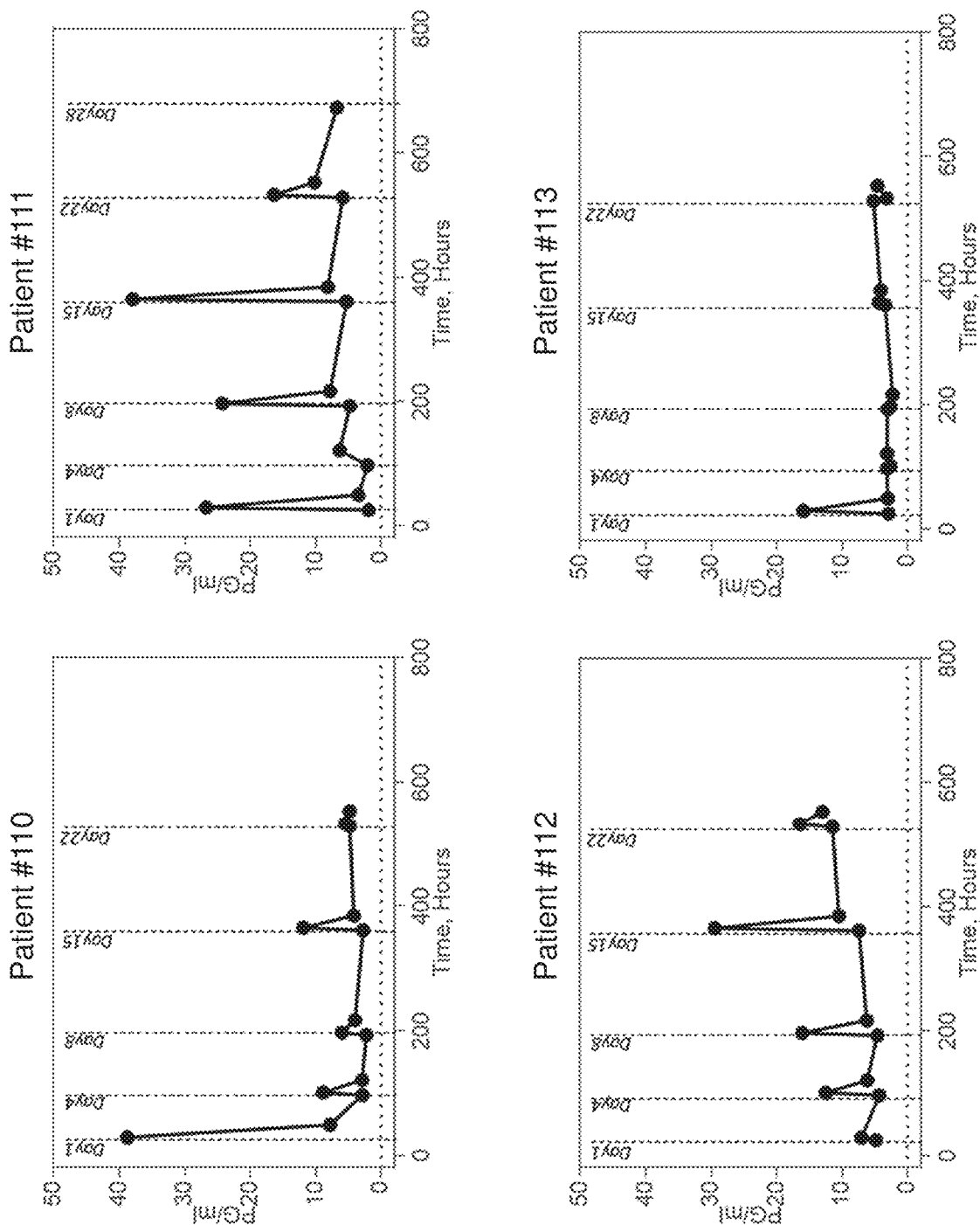

FIG. 16c. TNFα levels of patients treated with antibody MF4327xMF5196. In PG/ml, measured before dosing, 4 hours and 24 hours after the end of infusion. Dosing took place on day 1, day 4, day 8, and day 22. The patients received a priming dose of 5 mg on day 1, followed by step-up doses of 15 mg on day 4 and 25 mg on day 8, and a full dose of 60 mg on day 15. Cytokine levels were also determined at the end of a treatment cycle (day 28).

Figure 16D:
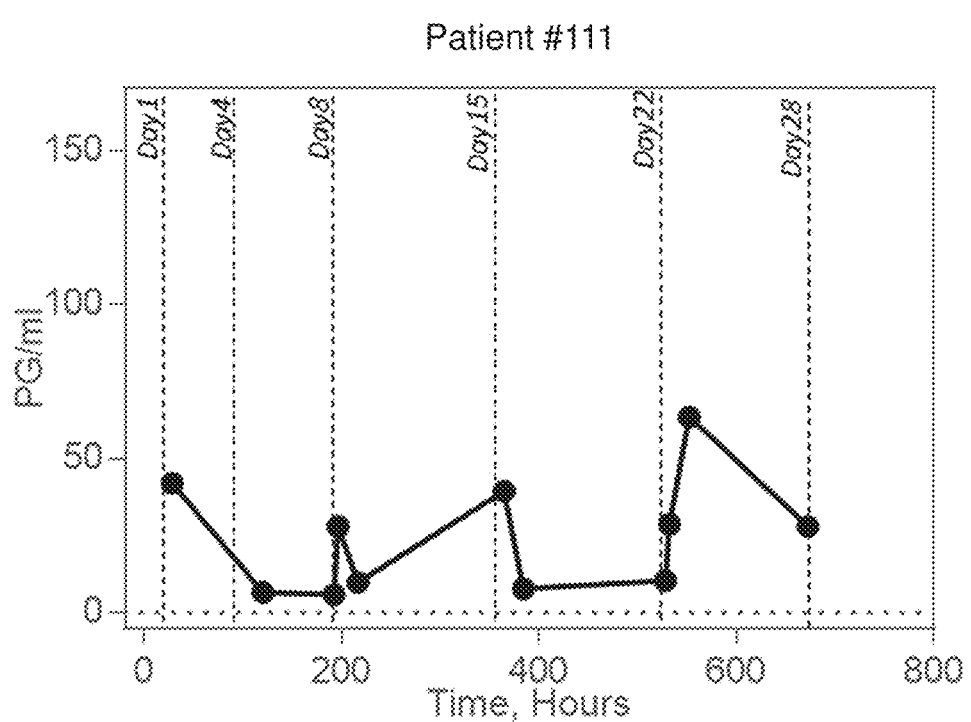

FIG. 16d. IFNγ levels of patient treated with antibody MF4327xMF5196. In PG/ml, measured before dosing, 4 hours and 24 hours after the end of infusion. Dosing took place on day 1, day 4, day 8, and day 22. The patients received a priming dose of 5 mg on day 1, followed by step-up doses of 15 mg on day 4 and 25 mg on day 8, and a full dose of 60 mg on day 15. Cytokine levels were also determined at the end of a treatment cycle (day 28).

DETAILED DESCRIPTION OF THE INVENTION

Dosing of therapeutic monoclonal antibodies (mAbs) is often based on body size. This is because of the idea that body size-based dosing would reduce inter-subject variability in drug exposure. However, most mAbs are target specific with a relatively large therapeutic window and generally a small contribution of body size to pharmacokinetic variability. On the other hand depending on the type of antibody, the target specificity of the antibody and other factors, antibodies can exhibit severe on and off target side effects. Some of the more serious of them being the conditions collectively referred to as cytokine release syndrome (CRS). Cytokine release syndrome is a form of systemic inflammatory response syndrome that arises as a complication of some diseases or infections, and is known to occur as an adverse effect of some antibody drugs and adoptive T-cell therapies. Severe cases have been also been referred to as "cytokine storms".

CRS as a potential adverse effect of antibody treatments has been known since the approval of the first monoclonal antibody drug, muromonab-CD3, which causes CRS. However, the problem became recognized as severe following the 2006 Phase I clinical trial with the agonistic CD28 binding antibody TGN 1412. All six healthy volunteers exhibited severe CRS and became seriously ill.

Recently, in the context of CD3 antibodies it is noted clinical trials with CD3/CD19 and CD3/CD123 bispecific antibodies have been put on hold (Johnson A. Oct. 9, 2018 and Sheridan C, 2016).

In the present invention it was found that a priming dose administered as a first administration followed by a full dose of an antibody that binds CD3 and CLEC12A was effective and well tolerated by subjects that were treated for a CLEC12A positive cancer. Without being bound by theory it is believed that priming with a lower dose that is escalated to the full dose in one or more steps is instrumental in this. A priming dose is typically given once but can be given twice, or more times in as many administrations. A priming dose can be followed by step-up dosing with gradual increments of the dose until the full dose is reached. A first amount of antibody is preferably a priming dose. Administrations of antibody doses are typically given at regular intervals. The interval between priming and subsequent priming or step-up administrations, if more than one, can vary between 1-7 days, but is typically one day, or three days. The interval between subsequent administrations of step-up doses, if more than one, can vary between 3-7 days, but is typically three days. The interval between administrations of a full dose is typically a week. The interval between a first priming administration and a subsequent step-up administration, if any, is typically three days. The interval between the last step-up administration and a subsequent full dose administration, if any, can vary between 3-7 days, but is typically three days. The interval between a first administration and a subsequent administration of a full dose is typically seven days. An administration of a dose is typically calculated per day. A priming dose, a step up dose or a full dose is an amount given at one day. The actual administration may take some time. It is typically but not necessarily an infusion over a period of one or more hours.

In the prior art dose escalation studies are predominantly performed in clinical trials to quickly find an effective dose and to avoid unnecessary exposure of patients to subtherapeutic doses (Tourneau, Michiels et al. 2009). In the present invention a priming dose is not given to quickly find a therapeutic dose and to avoid exposure of patients to sub-therapeutic doses. Instead it is given to subjects as part of a dosing regimen that is designed to treat the subjects while simultaneously reducing the incidence and/or extent of side effects in the treated population when the full dose is reached.

The invention provides a method of treating a subject for a CLEC12A positive cancer the method comprising treating the subject in need thereof with two or more administrations of a bispecific antibody that binds CD3 and CLEC12A wherein in a first administration a first amount of the bispecific antibody is administered and wherein in subsequent administrations the amount of bispecific antibody is higher than the amount of bispecific antibody in the first administration. The amount of administered bispecific antibody in the second of said two or more administrations is preferably higher than the amount of bispecific antibody in the first administration, and, in case of more than two administrations, lower than the amount of bispecific antibody in a third of said two or more administrations when the second administration involves a step-up dose. If the second administration is a full dose, the amount of administered bispecific antibody in the second and third administrations is equal. Preferably the amount of administered bispecific antibody in the third of said two or more administrations is higher than the amount of bispecific antibody in the second of said two or more administrations, and, in case where the third administration involves a step-up dose, lower than the amount in a fourth of said two or more administrations. After the administrations of incremental amounts of said bispecific antibody, i.e. after the priming and step-up phase, the bispecific antibody is preferably administered at an essentially constant dose in each of the subsequent administrations. The essentially constant dose is also referred to as the full dose.

The essentially constant dose in each of the subsequent administrations is preferably at least 15 mg of said bispecific antibody. The essentially constant dose is preferably at least, or equal to, 20, 25, 30, 35, 40, 45, 50, 55 mg, and preferably between 60-600 mg, such as between 60-120; 60-180; 60-200; 60-240; 60-480; 120-240; 120-480; 240-480; or 240-600 mg, of said bispecific antibody per subsequent administration.

The first amount of the bispecific antibody is preferably 9 mg or less, such as between 1-9 mg or between 1-5 mg, preferably 3 mg or less, such as between 1-3 mg, more preferably about 1 mg, even more preferably about 3 mg, most preferably about 5 mg.

The administrations of incremental amounts of antibody are preferably done with an interval of 3 to 4 days between administrations. The interval between the day of administration of the essentially constant amounts of antibody is preferably 6-8 days, preferably 7 days.

The first amount of bispecific antibody is preferably a subtherapeutic amount of bispecific antibody. A subtherapeutic amount of bispecific antibody is an amount of antibody that typically does not produce a therapeutic effect when administered in weekly administrations.

In one embodiment, a first amount of bispecific antibody of between 1-9 mg is given on day 1 of treatment. A first step up dose of between 3-20 mg, preferably between 10-20 mg, is given on day 3, 4, or 5 of treatment; a second step up dose of between 15-30 mg, preferably between 20-30 mg, is given on day 7, 8 or 9 of treatment; and a full dose of between 25-600 mg is given on day 14, 15 or 16 of treatment.

In one embodiment, a first amount of bispecific antibody of 1 mg is given on day 1 of treatment. A first step up dose of 3 mg is given on day 4 of treatment; a second step up dose of 15 mg is given on day 8 of treatment; and a full dose of 25 mg is given on day 15 of treatment.

In one embodiment, a first amount of bispecific antibody of 3 mg is given on day 1 of treatment. A step up dose of 15 mg is given on day 4 of treatment; and a full dose of 25 mg is given on day 8 of treatment.

In one embodiment, a first amount of bispecific antibody of 5 mg is given on day 1 of treatment. A step up dose of 15 mg is given on day 4 of treatment; and a full dose of 25 mg is given on day 8 of treatment.

In one embodiment, a first amount of bispecific antibody of 3 mg is given on day 1 of treatment. A first step up dose of 10 mg is given on day 4 of treatment; a second step up dose of 25 mg is given on day 8 of treatment; and a full dose of 40 mg is given on day 15 of treatment.

In one embodiment, a first amount of bispecific antibody of 3 mg is given on day 1 of treatment. A first step up dose of 15 mg is given on day 4 of treatment; a second step up dose of 25 mg is given on day 8 of treatment, a full dose of 40 mg is given on day 15 of treatment.

In another embodiment, a first amount of bispecific antibody of 5 mg is given on day 1 of treatment. A first step up dose of 10 mg is given on day 4 of treatment; a second step up dose of 25 mg is given on day 8 of treatment; and a full dose of 40 mg is given on day 15 of treatment.

In another embodiment, a first amount of bispecific antibody of 5 mg is given on day 1 of treatment. A first step up dose of 15 mg is given on day 4 of treatment; a second step up dose of 25 mg is given on day 8 of treatment and a full dose of 40 mg is given on day 15 of treatment.

In another embodiment, a first amount of bispecific antibody of 3 mg is given on day 1 of treatment. A first step up dose of 10 mg is given on day 4 of treatment; a second step up dose of 25 mg is given on day 8 of treatment; and a full dose of 60 mg is given on day 15 of treatment.

In another embodiment, a first amount of bispecific antibody of 3 mg is given on day 1 of treatment. A first step up dose of 15 mg is given on day 4 of treatment; a second step up dose of 25 mg is given on day 8 of treatment; and a full dose of 60 mg is given on day 15 of treatment.

In another embodiment, a first amount of bispecific antibody of 5 mg is given on day 1 of treatment. A first step up dose of 10 mg is given on day 4 of treatment; a second step up dose of 25 mg is given on day 8 of treatment; and a full dose of 60 mg is given on day 15 of treatment.

In another embodiment, a first amount of bispecific antibody of 5 mg is given on day 1 of treatment. A first step up dose of 15 mg is given on day 4 of treatment; a second step up dose of 25 mg is given on day 8 of treatment; and a full dose of 60 mg is given on day 15 of treatment.

In another embodiment, a first amount of bispecific antibody of 3 mg is given on day 1 of treatment. A first step up dose of 10 mg is given on day 4 of treatment; a second step up dose of 25 mg is given on day 8 of treatment, a full dose of 120 mg is given on day 15 of treatment.

In another embodiment, a first amount of bispecific antibody of 3 mg is given on day 1 of treatment. A first step up dose of 15 mg is given on day 4 of treatment; a second step up dose of 25 mg is given on day 8 of treatment, a full dose of 120 mg is given on day 15 of treatment.

In another embodiment, a first amount of bispecific antibody of 5 mg is given on day 1 of treatment. A first step up dose of 10 mg is given on day 4 of treatment; a second step up dose of 25 mg is given on day 8 of treatment, a full dose of 120 mg is given on day 15 of treatment.

In another embodiment, a first amount of bispecific antibody of 5 mg is given on day 1 of treatment. A first step up dose of 15 mg is given on day 4 of treatment; a second step up dose of 25 mg is given on day 8 of treatment, a full dose of 120 mg is given on day 15 of treatment.

In another embodiment, a first amount of bispecific antibody of 3 mg is given on day 1 of treatment. A first step up dose of 10 mg is given on day 4 of treatment; a second step up dose of 25 mg is given on day 8 of treatment, a full dose of 240 mg is given on day 15 of treatment.

In another embodiment, a first amount of bispecific antibody of 3 mg is given on day 1 of treatment. A first step up dose of 15 mg is given on day 4 of treatment; a second step up dose of 25 mg is given on day 8 of treatment, a full dose of 240 mg is given on day 15 of treatment.

In another embodiment, a first amount of bispecific antibody of 5 mg is given on day 1 of treatment. A first step up dose of 10 mg is given on day 4 of treatment; a second step up dose of 25 mg is given on day 8 of treatment, a full dose of 240 mg is given on day 15 of treatment.

In another embodiment, a first amount of bispecific antibody of 5 mg is given on day 1 of treatment. A first step up dose of 15 mg is given on day 4 of treatment; a second step up dose of 25 mg is given on day 8 of treatment, a full dose of 240 mg is given on day 15 of treatment.

In another embodiment, a first amount of bispecific antibody of 3 mg is given on day 1 of treatment. A first step up dose of 10 mg is given on day 4 of treatment; a second step up dose of 25 mg is given on day 8 of treatment, a full dose of 400 mg is given on day 15 of treatment.

In another embodiment, a first amount of bispecific antibody of 3 mg is given on day 1 of treatment. A first step up dose of 15 mg is given on day 4 of treatment; a second step up dose of 25 mg is given on day 8 of treatment, a full dose of 400 mg is given on day 15 of treatment.

In another embodiment, a first amount of bispecific antibody of 5 mg is given on day 1 of treatment. A first step up dose of 10 mg is given on day 4 of treatment; a second step up dose of 25 mg is given on day 8 of treatment, a full dose of 400 mg is given on day 15 of treatment.

In another embodiment, a first amount of bispecific antibody of 5 mg is given on day 1 of treatment. A first step up dose of 15 mg is given on day 4 of treatment; a second step up dose of 25 mg is given on day 8 of treatment, a full dose of 400 mg is given on day 15 of treatment.

In another embodiment, a first amount of bispecific antibody of 3 mg is given on day 1 of treatment. A first step up dose of 10 mg is given on day 4 of treatment; a second step up dose of 25 mg is given on day 8 of treatment, a full dose of 600 mg is given on day 15 of treatment.

In another embodiment, a first amount of bispecific antibody of 3 mg is given on day 1 of treatment. A first step up dose of 15 mg is given on day 4 of treatment; a second step up dose of 25 mg is given on day 8 of treatment, a full dose of 600 mg is given on day 15 of treatment.

In another embodiment, a first amount of bispecific antibody of 5 mg is given on day 1 of treatment. A first step up dose of 10 mg is given on day 4 of treatment; a second step up dose of 25 mg is given on day 8 of treatment, a full dose of 600 mg is given on day 15 of treatment.

In another embodiment, a first amount of bispecific antibody of 5 mg is given on day 1 of treatment. A first step up dose of 15 mg is given on day 4 of treatment; a second step up dose of 25 mg is given on day 8 of treatment, a full dose of 600 mg is given on day 15 of treatment.

If the step from one dose to another, such as for instance from 25 mg to 240 mg, appears to cause CRS symptoms, the dosage regimen can be adapted to include one or more further step-up doses, of for instance 120 mg. It can also be decided to prolong the intervals between the step-up doses and/or the full dose. These principles can be applied to any of the dosage regimens disclosed herein.

The invention uses a specific method of administration, preferably with discrete time intervals. The regimen of administration is designed to give an efficacious and safe full dose. In one aspect a safe dose aims to prevent and minimize the severity and incidence of Cytokine release syndrome (CRS).

A preferred administration regimen comprises administering a priming dose in one or more administrations, one or more step-up doses wherein the dose is increased with increments of the dose until the full dose is reached. The increments are preferably gradual. In one aspect the increments are equal increments until the full dose or maintenance dose is reached. It has, however, been found that starting with a higher priming dose and/or higher first step-up dose leads to less severe side effects, such as for instance cytokine release, at full dose as compared to starting at a low or very low priming dose and/or first step-up dose. In other words, starting with a higher priming dose mitigates cytokine release more effectively than starting with a lower priming dose. Exemplary higher priming doses are for instance 3 or 5 mg. A lower priming dose is for instance 1 mg.

The full dose is typically fixed over the treatment period but can be adjusted up or down depending on the individual therapeutic and/or side effect response of the subject.

The one or more step-up doses are preferably given in the first one or two weeks of administration. In one embodiment the first priming administration(s) and the step-up administrations are given every 3 days (D1-D4-D8) which is followed by administrations of the full dose every 7 days (on weekly basis). The dose at day 8 (D8) can be equal to the full dose. The full dose is preferably started from day 8-15 depending on the number of step-up administrations.

In one aspect of the invention one or more administrations of antibody are accompanied by a pre- and/or concomitant treatment with acetaminophen and an anti-histamine. The anti-histamine is preferably an H1-antagonist. An H1-antagonist inhibits the action of histamine at the H1 receptor. The treatment with acetaminophen and an anti-histamine is preferably given on the same day as and preferably prior to the antibody administration. The treatment with acetaminophen and an anti-histamine is preferably given with each antibody administration.

Provided is a bispecific antibody that binds CD3 and CLEC12A for use in a method of treatment of CLEC12A positive cancer in a subject, wherein said treatment comprises two or more administrations of a bispecific antibody that binds CD3 and CLEC12A, wherein in a first administration a first amount of the bispecific antibody is administered and wherein in each of the subsequent administrations the amount of bispecific antibody is higher than the amount of bispecific antibody in the first administration. The invention further provides the use of a bispecific antibody that binds CD3 and CLEC12A for the manufacture of a medicament for the treatment of CLEC12A positive cancer in a subject, wherein in a first administration a first amount of the bispecific antibody is administered and wherein in each of the subsequent administrations the amount of bispecific antibody is higher than the amount of bispecific antibody in the first administration.

Further provided is a method of purging CLEC12A positive hemopoietic cells from a subject and repopulating the hemopoietic system of said subject with normal CLEC12A positive cells, the method comprising administering to the subject in need thereof a bispecific antibody that binds CD3 and CLEC12A at intervals thereby stimulating hemopoietic stem cells of said subject to repopulate said hemopoietic system with newly formed hemopoietic stem cell derived cells, including CLEC12A positive cells. The subject is preferably a subject with AML, myeloproliferative neoplasm blast phase (MPN-BP), myelofibrosis (MF) or myelodysplastic syndrome (MDS). In a preferred embodiment the subject has myeloproliferative neoplasm blast phase (MPN-BP), myelofibrosis (MF) or myelodysplastic syndrome (MDS). Normal hemopoietic stem cells were found to be predominantly CLEC12A negative. In the progenitor fraction CLEC12A expression is restricted to the granulocyte-macrophage progenitor (GMP) cells and a fraction of the common myeloid progenitor (CMP) and megakaryocyte-erythroid progenitor (MEP) cells. Following the purging of CLEC12A positive cells those CMP and MEP that are not purged can still give rise to GMP and BFU-E (erythrocytes) and CFU-Mk (megakaryocytes). Treatment with a CD3xCLEC12A bispecific antibody as described herein can remove malignant cells, while leaving the potential of the hemopoietic stem and progenitor cells untouched. These are stimulated upon treatment with an antibody as described herein to repopulate the hemopoietic system with new, healthy cells, including CLEC12A positive cells. The stimulated cells also produce new differentiated CLEC12A negative cells. This can be achieved with a treatment with the antibody thereby at least reducing an immunological impact of removing CLEC12A positive cells from the hemopoietic system, when compared to CD3 engager approaching using CD19 or CD123 or other targets. Repopulation time is at least shorter than with other CD3 engager approaches such as CD19 and CD123. In addition because CFU-Mk and BFU-E progenitors are spared in a treatment of the invention the platelet producing capacity and the erythrocyte producing capacity of the hemopoietic system are also spared when compared to other CD3 engager formats.

Also provided is a method of purging CLEC12A positive hemopoietic cells from a subject and repopulating the hemopoietic system of said subject with normal CLEC12A positive cells, the method comprising administering to the subject in need thereof a bispecific antibody that binds CD3 and CLEC12A at intervals thereby inducing hemopoietic stem cells and/or hemopoietic progenitor cells of said subject to repopulate said hemopoietic system with newly formed hemopoietic stem cell derived CLEC12A positive cells.

Further provided is a method for stimulating granulocyte and monocyte development in a subject the method comprising administering a bispecific antibody that binds CD3 and CLEC12A at intervals to the subject in need thereof thereby inducing the development of granulocytes and monocytes from CLEC12A negative hemopoietic stem cells or progenitor cells. The administration at intervals preferably follows the interval as described herein above. The dosing schedule is preferably as described herein.

The subject is preferably a subject with AML, myeloproliferative neoplasm blast phase (MPN-BP), myelofibrosis (MF) or myelodysplastic syndrome (MDS). In a preferred embodiment the subject has myeloproliferative neoplasm blast phase (MPN-BP), myelofibrosis (MF) or myelodysplastic syndrome (MDS).

Also provided is a method of preparing an autologous bone marrow cell graft for a subject that is being treated for a CLEC12A positive cancer, the method comprising incubating a bone marrow cell preparation of said subject with a bispecific antibody that binds CD3 and CLEC12A under conditions suitable for killing of CLEC12A positive cells and subsequently collecting bone marrow cells from said incubation. Further provided is a method of treating a CLEC12A positive cancer in a subject, the method comprising incubating a bone marrow cell preparation of said subject with a bispecific antibody that binds CD3 and CLEC12A under conditions suitable for killing of CLEC12A positive cells, treating the subject with an hemopoietic system ablative therapy and providing said subject with a bone marrow cell graft comprising said incubated bone marrow cells. T-cells in the autologous graft derived from the bone marrow or the blood in the graft are retargeted to eliminate CLEC12A positive cells from the autologous graft. A CD3 and CLEC12A bispecific antibody as disclosed herein is effective even at low effector target cell ratio's, including at a range of 1:3-1:97, and at levels reflected in FIG. 6 and Table II. Conditions suitable for killing of CLEC12A positive cells as mentioned herein entail the presence of T cells such as autologous T cells or pre-activated T cells. Such cells are normally present in a bone marrow preparation as a result of the presence of a significant amount of blood that is typically also collected with many present day bone marrow harvest methods. Ablative therapy is a treatment that results in the destruction of cells as a result of the therapy. Many chemotherapies and other anti-tumor therapies also kill normal cells. One of the more sensitive organs is the bone marrow. A hemopoietic system ablative therapy in the context of the present invention is a therapy (or treatment) that has the additional or side-effect that a major part of the "normal" or "healthy" hemopoietic system is killed by the therapy or treatment. Bone marrow is often collected prior to treating the patient with the hemopoietic system ablative therapy. This bone marrow is transplanted back into the subject after completion of the therapy to stimulate the repopulation of the hemopoietic system of the subject. To prevent that aberrant cells are also transplanted, such bone marrow preparations are typically purged for aberrant cells. Sorting CD34 positive cells is one method when aberrant cells are not CD34 positive. Such purging methods often result is the removal of more cells than necessary leading to a slower than possible repopulation of the subjects hemopoietic system. A method of purging of the present invention efficiently removes aberrant cells from the bone marrow preparation allowing quicker repopulation.

In embodiments of the invention a method of providing a subject with a hemopoietic stem cell sparing cancer treatment is provided wherein the method comprises administering a bispecific antibody that binds CD3 and CLEC12A to the subject in need thereof. In some embodiment the subject has a CLEC12A positive cancer.

A bispecific antibody as disclosed herein is preferably administered as an intravenous infusion. Infusions typically take about 2-4 hours but longer and shorter administrations are also possible. Infusions do not normally extend over a period of more than 12 hours.

The increments in the amount of antibody until the essentially constant amount per administration is reached is also referred to as a dose escalation regimen within a single patient, or intra-patient dose escalation.

In order that the present description may be more readily understood, certain terms are first defined. Additional definitions are set forth throughout the detailed description. Unless stated otherwise, all technical and scientific terms used herein have the same meaning as commonly understood by one of ordinary skill in the art, and conventional methods of immunology, protein chemistry, biochemistry, recombinant DNA techniques and pharmacology are employed.

As used herein, the singular forms "a", "an" and "the" include plural referents unless the context clearly dictates otherwise. Use of the term "including" as well as other forms, such as "include", "includes", and "included", is not limiting.

As used herein, the term "CLEC12A" refers to C type lectin domain family 12 member A. CLEC12A is also referred to as C-Type Lectin Protein CLL-1; MICL; Dendritic Cell-Associated Lectin 2; C-Type Lectin Superfamily; Myeloid Inhibitory C-Type Lectin-Like Receptor; C-Type Lectin-Like Molecule-1; DCAL2; CLL1; C-Type Lectin-Like Molecule 1; DCAL-2; Killer cell lectin like receptor subfamily L, member 1 (KLRL1); CD371(cluster of differentiation 371) (Bakker, van den Oudenrijn et al. 2004; GenBank™ access.no: AY547296; Zhang W. et al. GenBank™ access.no: AF247788; Marshall, Willment et al. 2004; GenBank™ access.no: AY498550; Han, Zhang et al. 2004; Chen, Floyd et al. 2006. GenBank™ access.no: AY426759; Chen, Floyd et al. 2006. Ids: HGNC: 31713; Entrez Gene: 160364; Ensembl: ENSG00000172322; OMIM: 612088; UniProtKB: Q5QGZ9.

CLEC12A is an antigen that is expressed on leukemic blast cells and on leukemic stem cells in acute myeloid leukemia (AML), including the CD34 negative or CD34 low expressing leukemic stem cells (side population) (Bakker, van den Oudenrijn et al. 2004; van Rhenen, van Dongen et al. 2007; Moshaver, van Rhenen et al, 2008), as well as in myelodysplastic syndromes (MDS) (Bakker, van den Oudenrijn et al. 2004, and Toft-Peterson, Nederby et al, 2016). Expression of CLEC12A is otherwise thought to be restricted to cells of the hemopoietic lineage, particularly to myeloid lineage in peripheral blood and bone marrow, i.e., granulocytes, monocytes and dendritic cell precursors. More importantly, CLEC12A is absent on normal hemopoietic stem cells. Where reference is made to CLEC12A herein, the reference is to human CLEC12A (SEQ ID NO: 1), unless specifically stated otherwise.

The term "CLEC12A" means all variants (such as splice and mutation) that are referenced herein and isoforms thereof that retain the myeloid expression profile (both at surface expression level and mRNA level) including as described in Bakker, van den Oudenrijn et al. 2004 and Marshall, Willment et al. 2004. While accession numbers are primarily provided as a further method of identification, the actual sequence of the protein may vary, for instance because of a mutation in the encoding gene such as those occurring in some cancers or the like.

The term "CD3" (cluster of differentiation 3) refers a protein complex, which is composed of a CD3γ chain (SwissProt P09693), a CD3δ chain (SwissProt P04234), CD3ε chains (SwissProt P07766), and a CD3 zeta chain homodimer (SwissProt P20963). CD3ε is known under various aliases some of which are: "CD3e Molecule, Epsilon (CD3-TCR Complex)"; "CD3e Antigen, Epsilon Polypeptide (TiT3 Complex)"; T-Cell Surface Antigen T3/Leu-4 Epsilon Chain; T3E; T-Cell Antigen Receptor Complex, Epsilon Subunit Of T3; CD3e Antigen; CD3-Epsilon 3; IMD18; TCRE. Ids for CD3E Gene are HGNC: 1674; Entrez Gene: 916; Ensembl: ENSG00000198851; OMIM: 186830 and UniProtKB: P07766. These chains associate with the T-cell receptor (TCR) and the ζ-chain to generate an activation signal in T lymphocytes. The TCR, ζ-chain, and CD3 molecules together comprise the TCR complex. CD3 is expressed on T cells. Where reference is made to CD3 herein, the reference is to human CD3 (SEQ ID NOs: 2-5), unless specifically stated otherwise.

The term "antibody" as used herein means a proteinaceous molecule belonging to the immunoglobulin class of proteins, containing one or more domains that bind an epitope on an antigen, where such domains are or derived from or share sequence homology with the variable region of an antibody. Antibodies are typically made of basic structural units—each with two heavy chains and two light chains. Antibodies for therapeutic use are preferably as close to natural antibodies of the subject to be treated as possible (for instance human antibodies for human subjects). An antibody according to the present invention is not limited to any particular format or method of producing it.

A "bispecific antibody" is an antibody as described herein wherein one domain of the antibody binds to a first antigen whereas a second domain of the antibody binds to a second antigen, wherein said first and second antigens are not identical. The term "bispecific antibody" also encompasses antibodies wherein one heavy chain variable region/light chain variable region (VH/VL) combination binds a first epitope on an antigen and a second VH/VL combination that binds a second epitope. The term further includes antibodies wherein VH is capable of specifically recognizing a first antigen and the VL, paired with the VH in an immunoglobulin variable region, is capable of specifically recognizing a second antigen. The resulting VH/VL pair will bind either antigen 1 or antigen 2. Such so called "two-in-one antibodies", described in for instance WO 2008/027236, WO 2010/108127 and Schaefer, Haber et al, 2011. A bispecific antibody according to the present invention is not limited to any particular bispecific format or method of producing it.

The term 'common light chain' as used herein refers to the two light chains (or the VL part thereof) in the bispecific antibody. The two light chains (or the VL part thereof) may be identical or have some amino acid sequence differences while the binding specificity of the full length antibody is not affected. "Common" also refers to functional equivalents of the light chain of which the amino acid sequence is not identical. Many variants of said light chain exist wherein mutations (deletions, substitutions, insertions and/or additions) are present that do not influence the formation of functional binding regions. The light chain of the present invention can also be a light chain as specified herein above, having from 0 to 10, preferably from 0 to 5 amino acid insertions, deletions, substitutions, additions or a combination thereof. It is for instance within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like.

The term 'full length IgG' or 'full length antibody' according to the invention is defined as comprising an essentially complete IgG, which however does not necessarily have all functions of an intact IgG. For the avoidance of doubt, a full length IgG contains two heavy and two light chains. Each chain contains constant (C) and variable (V) regions, which can be broken down into domains designated CH1, CH2, CH3, VH, and CL, VL. An IgG antibody binds to antigen via the variable region domains contained in the Fab portion, and after binding can interact with molecules and cells of the immune system through the constant domains, mostly through the Fc portion. Full length antibodies according to the invention encompass IgG molecules wherein mutations may be present that provide desired characteristics. Full length IgG should not have deletions of substantial portions of any of the regions. However, IgG molecules wherein one or several amino acid residues are deleted, without essentially altering the binding characteristics of the resulting IgG molecule, are embraced within the term "full length IgG". For instance, such IgG molecules can have a deletion of between 1 and 10 amino acid residues, preferably in non-CDR regions, wherein the deleted amino acids are not essential for the binding specificity of the IgG.

"Percent (%) identity" as referred to amino acid sequences herein is defined as the percentage of amino acid residues in a candidate sequence that are identical with the amino acid residues in a selected sequence, after aligning the sequences for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B., 1983). The percent sequence identity between two amino acid sequences may be determined using the Needleman and Wunsch algorithm for the alignment of two sequences. (Needleman and Wunsch, 1970). The Needleman-Wunsch algorithm has been implemented in the computer program NEEDLE. For the purpose of this invention the NEEDLE program from the EMBOSS package may be used (version 2.8.0 or higher, Rice, Longden et al, 2000. For protein sequences, EBLOSUM62 is used for the substitution matrix. The optional parameters used are a gap-open penalty of 10 and a gap extension penalty of 0.5.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment.

As an antibody typically recognizes an epitope of an antigen, and such an epitope may be present in other compounds as well, antibodies according to the present invention that "specifically recognize" an antigen, for example, CLEC12A or CD3, may recognize other compounds as well, if such other compounds contain the same kind of epitope. Hence, the terms "specifically recognizes" with respect to an antigen and antibody interaction does not exclude binding of the antibodies to other compounds that contain the same kind of epitope.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein (so-called linear and conformational epitopes). Epitopes formed from contiguous, linear amino acids are typically retained on exposure to denaturing solvents, whereas epitopes formed by tertiary folding, conformation are typically lost on treatment with denaturing solvents. An epitope may typically include 3, 4, 5, 6, 7, 8, 9, 10, 11, 12, 13, 14 or 15 amino acids in a unique spatial conformation. Methods of determining spatial conformation of epitopes are known to persons of ordinary skill in the art and include techniques in the art for example, x-ray crystallography, HDX-MS and 2-dimensional nuclear magnetic resonance, pepscan, and alanine scan depending on the nature of the epitope (see, e.g., Morris G. E., 1996).

The term 'aberrant cells' as used herein includes tumor cells, more specifically tumor cells of hematological origin including also pre-leukemic cells such as cells that cause myelodysplastic syndromes (MDS) and leukemic cells such as acute myeloid leukemia (AML) tumor cells or chronic myelogenous leukemia (CML) cells.

The term 'immune effector cell' or 'effector cell' as used herein refers to a cell within the natural repertoire of cells in the mammalian immune system which can be activated to affect the viability of a target cell. Immune effector cells include cells of the lymphoid lineage such as natural killer (NK) cells, T cells including cytotoxic T cells, or B cells, and including cells of the myeloid lineage, such as monocytes or macrophages, dendritic cells and neutrophilic granulocytes. Hence, said effector cell is preferably an NK cell, a T cell, a B cell, a monocyte, a macrophage, a dendritic cell or a neutrophilic granulocyte. The recruitment of effector cells to aberrant cells means that immune effector cells are brought in proximity to the aberrant target cells such that the effector cells can directly kill, or indirectly initiate the killing of the aberrant cells.

As used herein, the terms "subject" and "patient" are used interchangeably and refer to a mammal such as a human, mouse, rat, hamster, guinea pig, rabbit, cat, dog, monkey, cow, horse, pig and the like (e.g., a patient, such as a human patient, having cancer).

The terms "treat," "treating," and "treatment," as used herein, refer to any type of intervention or process performed on, or administering an active agent or combination of active agents to the subject with the objective of reversing, alleviating, ameliorating, inhibiting, or slowing down or preventing the progression, development, severity or recurrence of a symptom, complication, condition or biochemical indicia associated with a disease.

As used herein, "effective treatment" or "positive therapeutic response" refers to a treatment producing a beneficial effect, e.g., amelioration of at least one symptom of a disease or disorder, e.g., cancer. A beneficial effect can take the form of an improvement over baseline, including an improvement over a measurement or observation made prior to initiation of therapy according to the method. For example, a beneficial effect can take the form of slowing, stabilizing, stopping or reversing the progression of a cancer in a subject at any clinical stage, as evidenced by a decrease or elimination of a clinical or diagnostic symptom of the disease, or of a marker of cancer. Effective treatment may, for example, decrease in tumor size, decrease the presence of circulating tumor cells, reduce or prevent metastases of a tumor, slow or arrest tumor growth and/or prevent or delay tumor recurrence or relapse.

The term "therapeutic amount" refers to an amount of an agent or combination of agents that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In some embodiments, a therapeutic amount is an amount sufficient to delay tumor development. In some embodiments, a therapeutic amount is an amount sufficient to prevent or delay tumor recurrence. A therapeutic amount can be administered in one or more administrations. The therapeutic amount of the drug or composition may: (i) reduce the number of cancer cells; (ii) reduce tumor size; (iii) inhibit, retard, slow to some extent and may stop cancer cell infiltration into peripheral organs; (iv) inhibit tumor metastasis; (v) inhibit tumor growth; (vi) prevent or delay occurrence and/or recurrence of tumor; and/or (vii) relieve to some extent one or more of the symptoms associated with the cancer. In one example, an "therapeutic amount" is the amount of a CLEC12A/CD3 bispecific antibody that effects a decrease in a cancer (for example a decrease in the number of cancer cells) or slowing of progression of a cancer, such as acute myeloid leukemia, myelodysplastic syndrome or chronic myelogenous leukemia.

As disclosed herein bispecific antibodies for use in the methods provided herein include bispecific antibodies that comprise one heavy chain variable region/light chain variable region (VH/VL) combination that binds CLEC12A, and a second VH/VL combination that binds CD3.

Suitable CLEC12A heavy chain variable (VH) regions for use in a CLEC12A/CD3 bispecific antibody include those which bind to CLEC12A. In preferred embodiments, the CLEC12A VH region of a CLEC12A/CD3 bispecific antibody binds to CLEC12A expressed on tumor cells. Exemplary CLEC12A VH regions for use in the CLEC12A/CD3 bispecific antibody are disclosed, for example, in WO2017/010874, WO2014/051433, and WO2005/000894 (each of which is incorporated herein by reference).

In some embodiments, the binding affinity of the CLEC12A/CD3 bispecific antibody for CLEC12A on tumor cells is at least 2 times, 4 times, 6 times, 10 times, 20 times, 30 times, 40 times or 50 times higher than the affinity of binding to CD3. In certain embodiments, the CLEC12A binding affinity of the CLEC12A/CD3 bispecific antibody for CLEC12A is between about $1 \times 10e-6$ M and $1 \times 10e-10$ M, between about $1 \times 10e-7$ M and $1 \times 10e-10$ M, or between about $1 \times 10e-8$ and $1 \times 10e-10$. In some embodiments, CLEC12A binding affinity of the CLEC12A/CD3 bispecific antibody for CLEC12A is at least $1 \times 10-e8$ M, preferably at least $1 \times 10-e9$ M. In certain embodiments, the binding affinity of the CLEC12A/CD3 bispecific antibody for CLEC12A is between about $1 \times 10e-8$ M and $1 \times 10e-9$ M including, for example, about $2 \times 10e-9$ M, about $3 \times 10e-9$ M, about $4 \times 10e-9$ M, about $5 \times 10e-9$ M, about $6 \times 10e-9$ M, about $7 \times 10e-9$ M, $8 \times 10e-9$ M or about $9 \times 10e-9$ M, and the binding affinity of the CLEC12A/CD3 bispecific antibody for CD3 is at least 30 times lower, at least 40 times lower, or at least 50 times lower.

In certain embodiments, the CD3 VH region of the CLEC12A/CD3 bispecific antibody binds to cell surface expressed CD3/TCR on human T cell lines with an affinity (KD) that is significantly less than the affinity of murine anti-CD3 antibody, mOKT3. In some embodiments, the CD3 VH region of the CLEC12A/CD3 bispecific antibody binds to CD3 with a binding affinity of at least $1 \times 10-e6$ M. In some embodiments, the CD3 binding affinity of the bispecific antibody is between about $1 \times 10e-6$ M and $1 \times 10e-10$ M. In some embodiments, the CD3 binding affinity of the CD3 VH region of the bispecific antibody is between about $1 \times 10e-7$ M-$1 \times 10e-8$ M.

In some embodiments, the CLEC12A/CD3 bispecific antibody comprises a first heavy chain variable region that binds human CLEC12A, wherein the heavy chain variable region comprises:

(a) a heavy chain CDR1 comprising the amino acid sequence SGYTFTGY (SEQ ID NO: 9), a heavy chain CDR2 comprising the amino acid sequence IINPSGGS (SEQ ID NO: 10-), and a heavy chain CDR3 comprising the amino acid sequence GTTGDWFDY (SEQ ID NO: 11);

(b) a heavy chain CDR1 comprising the amino acid sequence SGYTFTSY (SEQ ID NO: 13), a heavy chain CDR2 comprising the amino acid sequence IINPSGGS (SEQ ID NO: 14), and a heavy chain CDR3 comprising the amino acid sequence GNYGDEFDY (SEQ ID NO:15); or (c) a heavy chain CDR1 comprises the amino acid sequence SGYTFTGY (SEQ ID NO: 17), a heavy chain CDR2 comprising the amino acid sequence WINPNSGG (SEQ ID NO: 18), and a heavy chain CDR3 comprising the amino acid sequence DGYFADAFDY (SEQ ID NO: 19).

Conservative variations of 1, 2 or 3 amino acid residues from the recited CDR sequences are allowed while retaining the same kind of binding activity (in kind, not necessarily in amount). Hence, said heavy chain CDR 1, 2 and 3 sequences preferably contain sequences that deviate in no more than three, preferably no more than two, more preferably no more than one amino acid from the recited CDR sequences. In certain embodiments, the heavy chain CDR 1, 2 and 3 sequences are identical to the recited CDR sequences.

In some embodiments, the CLEC12A/CD3 bispecific antibody comprises a heavy chain variable region that binds human CLEC12A, wherein said heavy chain variable region comprises the HCDR1, HCDR2 and HCDR3 of the VH region set forth in SEQ ID NOs: 12, 16 or 20.

In some embodiments, the CLEC12A/CD3 bispecific antibody comprises a heavy chain variable region that binds human CLEC12A, wherein said heavy chain variable region comprises an amino acid sequence at least 90%, preferably at least 95%, more preferably at least 97%, more preferably at least 98%, more preferably at least 99% identical or 100% identical to the amino acid sequence set forth in SEQ ID NOs: 12, 16 or 20.

For example, in some embodiments, the heavy chain variable region of the bispecific antibody that binds human CLEC12A can have 0-10, preferably 0-5 amino acid insertions, deletions, substitutions, additions in the sequence of the heavy chain variable region outside of the three CDR sequences, or a combination thereof. In some embodiments, the heavy chain variable region comprises from 0 to 9, from 0 to 8, from 0 to 7, from 0 to 6, from 0 to 5, from 0 to 4, preferably from 0 to 3, preferably from 0 to 2, preferably from 0 to 1 and preferably 0 amino acid insertions, deletions, substitutions, additions with respect to the indicated amino acid sequence, or a combination thereof.

In certain embodiments, the CLEC12A/CD3 bispecific antibody comprises a heavy chain variable region that binds human CLEC12A, wherein said heavy chain variable region comprises an amino acid sequence selected from SEQ ID NOs: 12, 16 and 20.

CD3 heavy chain variable (VH) regions suitable for use in the CLEC12A/CD3 bispecific antibody include those which can bind a CD3γ chain, a CD3δ chain, a CD3ε chain or a combination of CD3δ/CD3ε or CD3γ/CD3ε. In some embodiments, the CD3 VH region of the bispecific antibody binds the CD3ε chain. In some embodiments, the CD3 VH region binds to human CD3. In some embodiments, the CD3 VH region binds to the human CD3ε chain.

Exemplary CD3 binding regions for use in the CLEC12A/CD3 bispecific antibody are disclosed in WO2017/010874, WO2014/051433 and WO2005/118635 (each of which is incorporated herein by reference).

In certain embodiments, the CLEC12A/CD3 bispecific antibody comprises a heavy chain variable region that binds CD3, wherein said heavy chain variable region comprises:

(a) a heavy chain CDR1 comprising the amino acid sequence GFTFSSYG (SEQ ID NO: 21), a heavy chain CDR2 sequence comprising the amino acid sequence IWYNGRKQ (SEQ ID NO: 22), and a heavy chain CDR3 comprising the amino acid sequence GTGYNWFDP (SEQ ID NO: 23);

(b) a heavy chain CDR1 comprising the amino acid sequence GFTFSSYG (SEQ ID NO: 21), a heavy chain CDR2 sequence comprising the amino acid sequence IWYSGSKKN(SEQ ID NO: 30), and a heavy chain CDR3 comprising the amino acid sequence GTGYNWFDP (SEQ ID NO: 23);

(c) a heavy chain CDR1 comprising the amino acid sequence GFTFSSYG (SEQ ID NO: 21), a heavy chain CDR2 sequence comprising the amino acid sequence IWYHGRKQ (SEQ ID NO: 32), and a heavy chain CDR3 comprising the amino acid sequence GTGYNWFDP (SEQ ID NO: 23);

(d) a heavy chain CDR1 comprising the amino acid sequence GFTFSSYG (SEQ ID NO: 21), a heavy chain CDR2 sequence comprising the amino acid sequence IWY-HARKQ (SEQ ID NO: 34), and a heavy chain CDR3 comprising the amino acid sequence GTGYNWFDP (SEQ ID NO: 23);

(e) a heavy chain CDR1 comprising the amino acid sequence GFTFSSYG (SEQ ID NO: 21), a heavy chain CDR2 sequence comprising the amino acid sequence IWY-NARKQ (SEQ ID NO: 36), and a heavy chain CDR3 comprising the amino acid sequence GTGYNWFDP (SEQ ID NO: 23);

(g) a heavy chain CDR1 comprising the amino acid sequence GFTFSSYG (SEQ ID NO: 21), a heavy chain CDR2 sequence comprising the amino acid sequence IWYNTRKQ (SEQ ID NO: 45), and a heavy chain CDR3 comprising the amino acid sequence GTGYNWFDP (SEQ ID NO: 23);

(h) a heavy chain CDR1 comprising the amino acid sequence GFTFSSYG (SEQ ID NO: 21), a heavy chain CDR2 sequence comprising the amino acid sequence IWYDGKNT (SEQ ID NO: 47), and a heavy chain CDR3 comprising the amino acid sequence GTGYNWFDP (SEQ ID NO: 23);

(i) a heavy chain CDR1 comprising the amino acid sequence GFTFSSYG (SEQ ID NO: 21), a heavy chain CDR2 sequence comprising the amino acid sequence IYYDGSRT (SEQ ID NO: 49), and a heavy chain CDR3 comprising the amino acid sequence GTGYNWFDP (SEQ ID NO: 23); or (j) a heavy chain CDR1 comprising the amino acid sequence GFTFSSYG (SEQ ID NO: 21), a heavy chain CDR2 sequence comprising the amino acid sequence IWHDGRKT (SEQ ID NO: 51), and a heavy chain CDR3 comprising the amino acid sequence GTGYNWFDP (SEQ ID NO: 23).

The CDR1 comprising the amino acid sequence GFTFSSYG (SEQ ID NO: 21) is defined according to IMGT. The CDR1 may comprise the amino acid sequence SYGMH (SEQ ID NO: 60) as defined according to Kabat.

Variations of 1, 2 or 3 amino acid residues from the recited CDR sequences are allowed while retaining the same kind of binding activity (in kind, not necessarily in amount). Hence, said heavy chain CDR 1, 2 and 3 sequences preferably contain sequences that deviate in no more than three, preferably no more than two, more preferably no more than one amino acid from the recited CDR sequences. In certain embodiments, the heavy chain CDR 1, 2 and 3 sequences are identical to the recited CDR sequences.

In some embodiments, the CLEC12A/CD3 bispecific antibody comprises a heavy chain variable region that binds human CD3, wherein said heavy chain variable region comprises the HCDR1, HCDR2 and HCDR3 of the VH region set forth in SEQ ID NOs: 24-29, 31, 33, 35, 37-44, 46, 48, 50 and 52.

In some embodiments, the CLEC12A/CD3 bispecific antibody comprises a heavy chain variable region that binds human CD3, wherein said heavy chain variable region comprises at least 90%, preferably at least 95%, more preferably at least 97%, more preferably at least 98%, more preferably at least 99% identical or 100% identical to the amino acid sequence of one of the VH region sequences set forth in SEQ ID NO: 24-29, 31, 33, 35, 37-44, 46, 48, 50 and 52.

In certain embodiments, the CLEC12A/CD3 bispecific antibody comprises a heavy chain variable region that binds human CD3, wherein said heavy chain variable region comprises at least 90%, preferably at least 95%, more preferably at least 97%, more preferably at least 98%, more preferably at least 99% identical or 100% identical to the amino acid sequence of one of the sequences VH region set forth in SEQ ID NO: 37-44.

For example, in some embodiments, the heavy chain variable region of the bispecific antibody that binds human CD3 can have from 0 to 10, preferably from 0 to 5 amino acid insertions, deletions, substitutions, additions in the sequence of the heavy chain variable region outside of the three CDR sequences, or a combination thereof. In some embodiments, the heavy chain variable region comprises from 0 to 9, from 0 to 8, from 0 to 7, from 0 to 6, from 0 to 5, from 0 to 4, preferably from 0 to 3, preferably from 0 to 2, preferably from 0 to 1 and preferably 0 amino acid insertions, deletions, substitutions, additions with respect to the indicated amino acid sequence, or a combination thereof.

Additional variants of the disclosed amino acid sequences which retain CLEC12A or CD3 binding can be obtained, for example, from phage display libraries which contain the rearranged human IGKV1-39/IGKJ1 VL region (de Kruif, Kramer et al. 2010), and a collection of VH regions incorporating amino acid substitutions into the amino acid sequence of a CLEC12A or CD3 VH region disclosed herein, as previously described (e.g., US 2016/0368988). Phages encoding Fab regions which bind CLEC12A or CD3 may be selected and analyzed by flow cytometry, and sequenced to identify variants with amino acid substitutions, insertions, deletions or additions which retain antigen binding. For example, as described in US 2016/0368988, the CD3 VH region may be substituted at position A50 and be modified by an S, Y, M or a Q; D59 may be substituted by L, I, V, F, R, A, N, H, S, T, Y or E, preferably by an Y or an E; A61 may be substituted by N, I, H, Q, L, R, Y, E, S, T, D, K, V; and F105 may be substituted by an Y or an M. Tolerated amino acid substitutions can readily be found.

In certain embodiments, the CLEC12A/CD3 bispecific antibody comprises a heavy chain variable region that binds human CD3, wherein said heavy chain variable region comprises an amino acid sequence selected from SEQ ID NO: 24-29, 31, 33, 35, 37-44, 46, 48, 50 or 52.

In certain embodiments, CLEC12A/CD3 bispecific antibody comprises a heavy chain variable region that binds human CD3, wherein said heavy chain variable region comprises an amino acid sequence selected from SEQ ID NO: 37-44.

In certain embodiments, the CLEC12A/CD3 bispecific antibody comprises a first heavy chain variable region that binds human CLEC12A, wherein the first VH region comprises an amino acid sequence that is at least 90%, preferably at least 95%, more preferably at least 97%, more preferably at least 98%, more preferably at least 99% identical or 100% identical to the amino acid sequence of the VH region set forth in SEQ ID NO: 12, 16 and 20; and a second heavy chain variable region that binds human CD3 comprising, wherein the second VH region comprises an amino acid sequence that is at least 90%, preferably at least 95%, more preferably at least 97%, more preferably at least 98%, more preferably at least 99% identical or 100% identical to the amino acid sequence of one of the VH region sequences set forth in SEQ ID NO: 37-44.

In certain embodiments, the CLEC12A/CD3 bispecific antibody comprises a first heavy chain variable region that binds human CLEC12A, and a second heavy chain variable region that binds human CD3, wherein
(a) the first heavy chain variable region comprises:
(i) a heavy chain CDR1 comprising the amino acid sequence SGYTFTGY (SEQ ID NO: 9), a heavy chain CDR2 comprising the amino acid sequence IINPSGGS (SEQ ID NO: 10), and a heavy chain CDR3 comprising the amino acid sequence GTTGDWFDY (SEQ ID NO: 11);
(ii) a heavy chain CDR1 comprising the amino acid sequence SGYTFTSY (SEQ ID NO: 13), a heavy chain CDR2 comprising the amino acid sequence IINPSGGS (SEQ ID NO: 14), and a heavy chain CDR3 comprising the amino acid sequence GNYGDEFDY (SEQ ID NO: 15); or
(iii) a heavy chain CDR1 comprises the amino acid sequence SGYTFTGY (SEQ ID NO: 17), a heavy chain CDR2 comprising the amino acid sequence WINPNSGG (SEQ ID NO: 18), and a heavy chain CDR3 comprising the amino acid sequence DGYFADAFDY (SEQ ID NO: 19); and
(b) the second heavy chain variable region comprises,
(i) a heavy chain CDR1 comprising the amino acid sequence GFTFSSYG (SEQ ID NO: 21), a heavy chain CDR2 sequence comprising the amino acid sequence IWYNGRKQ (SEQ ID NO: 22), and a heavy chain CDR3 comprising the amino acid sequence GTGYNWFDP (SEQ ID NO: 23);
(ii) a heavy chain CDR1 comprising the amino acid sequence GFTFSSYG (SEQ ID NO: 21), a heavy chain CDR2 sequence comprising the amino acid sequence IWYSGSKKN (SEQ ID NO: 30), and a heavy chain CDR3 comprising the amino acid sequence GTGYNWFDP (SEQ ID NO: 23);
(iii) a heavy chain CDR1 comprising the amino acid sequence GFTFSSYG (SEQ ID NO: 21), a heavy chain CDR2 sequence comprising the amino acid sequence IWYHGRKQ (SEQ ID NO: 32), and a heavy chain CDR3 comprising the amino acid sequence GTGYNWFDP (SEQ ID NO: 23);
(iv) a heavy chain CDR1 comprising the amino acid sequence GFTFSSYG (SEQ ID NO: 21), a heavy chain CDR2 sequence comprising the amino acid sequence IWYHARKQ (SEQ ID NO: 34), and a heavy chain CDR3 comprising the amino acid sequence GTGYNWFDP (SEQ ID NO: 23);
(v) a heavy chain CDR1 comprising the amino acid sequence GFTFSSYG (SEQ ID NO: 21), a heavy chain CDR2 sequence comprising the amino acid sequence IWYNARKQ (SEQ ID NO: 36), and a heavy chain CDR3 comprising the amino acid sequence GTGYNWFDP (SEQ ID NO: 23);
(vi) a heavy chain CDR1 comprising the amino acid sequence GFTFSSYG (SEQ ID NO: 21), a heavy chain CDR2 sequence comprising the amino acid sequence IWYNTRKQ (SEQ ID NO: 45), and a heavy chain CDR3 comprising the amino acid sequence GTGYNWFDP (SEQ ID NO: 23);
(vii) a heavy chain CDR1 comprising the amino acid sequence GFTFSSYG (SEQ ID NO: 21), a heavy chain CDR2 sequence comprising the amino acid sequence IWYDGKNT (SEQ ID NO: 47), and a heavy chain CDR3 comprising the amino acid sequence GTGYNWFDP (SEQ ID NO: 23);
(viii) a heavy chain CDR1 comprising the amino acid sequence GFTFSSYG (SEQ ID NO: 21), a heavy chain CDR2 sequence comprising the amino acid sequence IYYDGSRT (SEQ ID NO: 49), and a heavy chain CDR3 comprising the amino acid sequence GTGYNWFDP (SEQ ID NO: 23); or
(ix) a heavy chain CDR1 comprising the amino acid sequence GFTFSSYG (SEQ ID NO: 21), a heavy chain CDR2 sequence comprising the amino acid sequence IWHDGRKT (SEQ ID NO: 51), and a heavy chain CDR3 comprising the amino acid sequence GTGY-NWFDP (SEQ ID NO: 23).

In certain embodiments, the CLEC12A/CD3 bispecific antibody comprises a first heavy chain variable region that binds human CLEC12A, wherein the first VH region comprises a heavy chain CDR1 comprising the amino acid sequence SGYTFTGY (SEQ ID NO: 9), a heavy chain CDR2 comprising the amino acid sequence IINPSGGS (SEQ ID NO: 10), and a heavy chain CDR3 comprising the amino acid sequence GTTGDWFDY (SEQ ID NO: 11); and a second heavy chain variable region, wherein the second VH region comprises a heavy chain CDR1 comprising the amino acid sequence GFTFSSYG (SEQ ID NO: 21), a heavy chain CDR2 comprising the amino acid sequence IWYNARKQ (SEQ ID NO: 36), and a heavy chain CDR3 comprising the amino acid sequence GTGYNWFDP (SEQ ID NO: 23).

In certain embodiments, the CLEC12A/CD3 bispecific antibody comprises a first heavy chain variable region that binds human CLEC12A, wherein the amino acid sequence of the first VH region is selected from SEQ ID NOs: 12, 16 and 20; and a second heavy chain variable region that binds human CD3, wherein the amino acid sequence of the second VH region is selected from SEQ ID NOs: 24-29, 31, 33, 35, 37-44, 46, 48, 50 and 52.

In certain embodiments, the CLEC12A/CD3 bispecific antibody comprises a first heavy chain variable region that binds human CLEC12A, wherein the amino acid sequence of the first VH region is SEQ ID NO: 12; and a second heavy chain variable region that binds human CD3, wherein the amino acid sequence of the second VH region is selected from SEQ ID NOs: 37-44.

In one embodiment, the CLEC12A/CD3 bispecific antibody comprises a first heavy chain variable region that binds human CLEC12A, wherein the amino acid sequence of the first VH region is set forth in SEQ ID NO: 12; and a second heavy chain variable region that binds human, wherein the amino acid sequence of the second VH region is set forth in SEQ ID NO: 37.

The light chain variable regions of the VH/VL CLEC12A binding region and the VH/VL binding region of the CD3 binding region of the CLEC12A/CD3 bispecific antibody may be the same as the VL region of parental CLEC12A monospecific antibody and/or the VL region of parental CD3 monospecific antibody, or alternative VL regions may be used for one or both VH/VL region combinations as long as the bispecific antibody retains binding to both the CLEC12A and CD3 antigens.

In some embodiments, the VL region of the VH/VL CLEC12A binding region of the CLEC12A/CD3 bispecific antibody is similar to the VL region of the VH/VL CD3 binding region. In certain embodiments, VL regions in the first and second VH/VL region combinations are identical.

In certain embodiments, the light chain variable region of one or both VH/VL binding regions of the CLEC12A/CD3 bispecific antibody comprises a common light chain. In some embodiments, the common light chain variable region of one or both VH/VL binding regions comprises a germline 012 variable region V-segment. In certain embodiment, the light chain variable region of one or both VH/VL binding regions comprises the kappa light chain V-segment IgVκ1-39*01. IgVκ1-39 is short for Immunoglobulin Variable Kappa 1-39 Gene. The gene is also known as Immunoglobulin Kappa Variable 1-39; IGKV139; IGKV1-39; 012a or 012. External Ids for the gene are HGNC: 5740; Entrez Gene: 28930; Ensembl: ENSG00000242371. The amino acid sequence for the V-region is provided in SEQ ID NO: 56. The V-region can be combined with one of five J-regions. Preferred J-regions are jk1 and jk5, and the joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org). In certain embodiments, the light chain variable region of one or both VH/VL binding regions comprises the kappa light chain IgVκ1-39*01/IGJκ1*01 or IgVκ1-39*01/IGJκ1*05 (SEQ ID NO: 57 and SEQ ID NO: 58, respectively).

In some embodiments, the light chain variable region of one or both VH/VL binding regions of the CLEC12A/CD3 bispecific antibody comprises an LCDR1 comprising the amino acid sequence QSISSY (SEQ ID NO: 53), an LCDR2 comprising the amino acid sequence AAS, and an LCDR3 comprising the amino acid sequence QQSYSTP (SEQ ID NO: 55) (i.e., the CDRs of IGKV1-39 according to IMGT). In some embodiments, the light chain variable region of one or both VH/VL binding regions of the CLEC12A/CD3 bispecific antibody comprises an LCDR1 comprising the amino acid sequence QSISSY (SEQ ID NO: 53), an LCDR2 comprising the amino acid sequence AASLQS (SEQ ID NO: 54), and an LCDR3 comprising the amino acid sequence QQSYSTP (SEQ ID NO: 55).

In some embodiments, one or both VH/VL binding regions of the CLEC12A/CD3 bispecific antibody comprise a light chain variable region comprising an amino acid sequence that is at least 90%, preferably at least 95%, more preferably at least 97%, more preferably at least 98%, more preferably at least 99% identical or 100% identical to the amino acid sequence of set forth in SEQ ID NO: 57. In some embodiments, one or both VH/VL binding regions of the CLEC12A/CD3 bispecific antibody comprise a light chain variable region comprising an amino acid sequence that is at least 90%, preferably at least 95%, more preferably at least 97%, more preferably at least 98%, more preferably at least 99% identical or 100% identical to the amino acid sequence of set forth in SEQ ID NO: 58.

For example, in some embodiments, the variable light chain of one or both VH/VL binding regions of the CLEC12A/CD3 bispecific antibody can have from 0 to 10, preferably from 0 to 5 amino acid insertions, deletions, substitutions, additions or a combination thereof with respect to SEQ ID NO: 57 or SEQ ID NO: 58. In some embodiments, the light chain variable region of one or both VH/VL binding regions of the CLEC12A/CD3 bispecific antibody comprises from 0 to 9, from 0 to 8, from 0 to 7, from 0 to 6, from 0 to 5, from 0 to 4, preferably from 0 to 3, preferably from 0 to 2, preferably from 0 to 1 and preferably 0 amino acid insertions, deletions, substitutions, additions with respect to the indicated amino acid sequence, or a combination thereof.

In other embodiments, the light chain variable region of one or both VH/VL binding regions of the CLEC12A/CD3 bispecific antibody comprises the amino acid sequence of SEQ ID NO: 57 or SEQ ID NO: 58. In certain embodiments, both VH/VL binding regions of the CLEC12A/CD3 bispecific antibody comprise identical VL regions. In one embodiment, the VL of both VH/VL binding regions of the CLEC12A/CD3 bispecific antibody comprises the amino acid sequence set forth in SEQ ID NO: 57. In one embodiment, the VL of both VH/VL binding regions of the CLEC12A/CD3 bispecific antibody comprises the amino acid sequence set forth in SEQ ID NO: 58.

CLEC12A/CD3 bispecific antibodies for use in the methods disclosed herein can be provided in a number of formats.

Many different formats of bispecific antibodies are known in the art, and have been reviewed by Kontermann, Brinkmann, 2015, 2018 and in Spiess, Zhai et al, 2015), which are each incorporated herein by reference. For example, bispecific antibody formats that are not classical antibodies with two VH/VL combinations, have at least a variable domain comprising a heavy chain variable region and a light chain variable region. This variable domain may be linked to a single chain Fv-fragment, monobody, a VH and a Fab-fragment that provides the second binding activity.

In some embodiments, the CLEC12A/CD3 bispecific antibodies used in the methods provided herein are generally of the human IgG subclass (e.g., for instance IgG1, IgG2, IgG3, IgG4). In certain embodiments, the antibodies are of the human IgG1 subclass. Full length IgG antibodies are preferred because of their favorable half-life and for reasons of low immunogenicity. Accordingly, in certain embodiments, the CLEC12A/CD3 bispecific antibody is a full length IgG molecule. In an embodiment, the CLEC12A/CD3 bispecific antibody is a full length IgG1 molecule.

Accordingly, in certain embodiments, the CLEC12A/CD3 bispecific antibody comprises a fragment crystallizable (Fc). The Fc of the CLEC12A/CD3 bispecific antibody is preferably comprised of a human constant region. A constant region or Fc of the CLEC12A/CD3 bispecific antibody may contain one or more, preferably not more than 10, preferably not more than 5 amino-acid differences with a constant region of a naturally occurring human antibody. For example, in certain embodiments, each Fab-arm of the bispecific antibodies may further include an Fc-region comprising modifications promoting the formation of the bispecific antibody, modifications affecting Fc-mediated effector functions, and/or other features described herein.

In preferred embodiments, a CLEC12A/CD3 bispecific full length IgG antibody has a mutated lower hinge and/or CH2 domains such that interaction of said bispecific IgG antibody with Fc gamma (Fcγ) receptors is reduced. As used herein, the term "such that interaction of said bispecific IgG antibody with Fc gamma receptors is reduced" means that the interaction of the CLEC12A/CD3 bispecific antibody with Fc gamma receptors, if such Fc gamma receptors are present in the vicinity of the antibody, is reduced. In certain embodiments, the interaction of the CLEC12A/CD3 bispecific antibody with the Fc receptor is essentially abolished. Bispecific antibodies with reduced Fcγ receptor binding have been previously described (US 2014/0120096, incorporated herein by reference).

In certain embodiments, the CLEC12A/CD3 bispecific antibody comprises a mutated lower hinge and/or CH2 domain with at least one substitution at amino acids positions 235 and/or 236 (EU numbering). Preferably, both amino acids positions 235 and 236 are substituted. As described in US 2014/0120096, substitutions at these sites are capable of essentially preventing the interaction between an antibody and the Fc receptor present on tumor cells or effector cells. Accordingly, in certain embodiments, the CLEC12A/CD3 bispecific antibody comprises a mutated CH2 and/or lower hinge domains comprising an L235G and/or G236R substitution. Preferably, both L235G and G236R are substituted. Alternatively, a person skilled in the art may introduce lower hinge and/or the CH2 domain mutations that comprise the substitutions 234F, 235E and/or 331S (Oganesyan, Gao et al. 2008). Preferably, all three substitutions are introduced in this alternative.

Bispecific antibodies are typically produced by cells that express nucleic acid(s) encoding the antibody. Accordingly, in some embodiments, the bispecific CLEC12A/CD3 antibodies disclosed herein are produced by providing a cell comprising one or more nucleic acids that encode the heavy and light chain variable regions and constant regions of the bispecific CLEC12A/CD3 antibody. The cell is preferably an animal cell, more preferably a mammal cell, more preferably a primate cell, most preferably a human cell. A suitable cell is any cell capable of comprising and preferably of producing the CLEC12A/CD3 bispecific antibody.

Suitable cells for antibody production are known in the art and include a hybridoma cell, a Chinese hamster ovary (CHO) cell, an NS0 cell or a PER-C6 cell. Various institutions and companies have developed cell lines for the large scale production of antibodies, for instance for clinical use. Non-limiting examples of such cell lines are CHO cells, NS0 cells or PER.C6 cells. In a particularly preferred embodiment said cell is a human cell. Preferably a cell that is transformed by an adenovirus E1 region or a functional equivalent thereof. A preferred example of such a cell line is the PER.C6 cell line or equivalent thereof. In a particularly preferred embodiment said cell is a CHO cell or a variant thereof. Preferably a variant that makes use of a Glutamine synthetase (GS) vector system for expression of an antibody. In one preferred embodiment, the cell is a CHO cell.

In some embodiments, the cell expresses the different light and heavy chains that make up the CLEC12A/CD3 bispecific antibody. In certain embodiments, the cell expresses two different heavy chains and at least one light chain. In one preferred embodiment, the cell expresses a "common light chain" as described herein to reduce the number of different antibody species (combinations of different heavy and light chains). For example, the respective VH regions are cloned into expression vectors using methods known in the art for production of bispecific IgG (WO2013/157954; incorporated herein by reference), in conjunction with the rearranged human IGKV1 39/IGKJ1 (huVκ1 39) light chain. The huVκ1 39 was previously shown to be able to pair with more than one heavy chain thereby giving rise to antibodies with diverse specificities, which facilitates the generation of bispecific molecules (de Kruif, Kramer et al. 2009; WO2009/157771).

An antibody producing cell that expresses a common light chain and equal amounts of the two heavy chains typically produces 50% bispecific antibody and 25% of each of the monospecific antibodies (i.e. having identical heavy light chain combinations). Several methods have been published to favor the production of the bispecific antibody over the production of the respective monospecific antibodies. Such is typically achieved by modifying the constant region of the heavy chains such that they favor heterodimerization (i.e. dimerization with the heavy chain of the other heavy/light chain combination) over homodimerization. In a preferred embodiment the bispecific antibody of the invention comprises two different immunoglobulin heavy chains with compatible heterodimerization domains. Various compatible heterodimerization domains have been described in the art. The compatible heterodimerization domains are preferably compatible immunoglobulin heavy chain CH3 heterodimerization domains. The art describes various ways in which such hetero-dimerization of heavy chains can be achieved.

One preferred method for producing the CLEC12A/CD3 bispecific antibody is disclosed in U.S. Pat. Nos. 9,248,181 and 9,358,286. Specifically, preferred mutations to produce essentially only bispecific full length IgG molecules are the amino acid substitutions L351K and T366K (EU numbering) in the first CH3 domain (the 'KK-variant' heavy chain) and the amino acid substitutions L351D and L368E in the second domain (the 'DE-variant' heavy chain), or vice versa. As previously described, the DE-variant and KK-variant preferentially pair to form heterodimers (so-called 'DEKK' bispecific molecules). Homodimerization of DE-variant heavy chains (DEDE homodimers) or KK-variant heavy chains (KKKK homodimers) hardly occurs due to strong repulsion between the charged residues in the CH3-CH3 interface between identical heavy chains.

Accordingly, in one embodiment the heavy chain/light chain combination that comprises the variable domain that binds CLEC12A, comprises a DE variant of the heavy chain. In this embodiment the heavy chain/light chain combination that comprises the variable domain that binds CD3 comprises a KK variant of the heavy chain.

A candidate CLEC12A/CD3 IgG bispecific antibody can be tested for binding using any suitable assay. For example, binding to membrane-expressed CD3 on HPB-ALL cells can be assessed by flow cytometry (according to the FACS procedure as previously described in WO2014/051433). In one embodiment, the binding of a candidate CLEC12A/CD3 bispecific antibody to CD3 on HPB ALL cells is demonstrated by flow cytometry, performed according to standard procedures known in the art. Binding to cell expressed CD3 is confirmed using CHO cell transfected with CD3δ/ε or CD3γ/ε. The binding of the candidate bispecific IgG1 to CLEC12A is determined using CHO cells transfected with a CLEC12A expression construct; a CD3 monospecific antibody and a CLEC12A monospecific antibody, as well as an irrelevant IgG1 isotype control mAb are included in the assay as controls (e.g., an antibody which binds CD3 and another antigen such as tetanus toxin (TT)).

The affinities of the CD3 and CLEC12A Fabs of a candidate CLEC12A/CD3 bispecific antibody for their targets can be measured by surface plasmon resonance (SPR) technology using a BIAcore T100. Briefly, an anti-human IgG mouse monoclonal antibody (Becton and Dickinson, cat. Nr. 555784) is coupled to the surfaces of a CM5 sensor chip using free amine chemistry (NHS/EDC). Then the bsAb is captured onto the sensor surface. Subsequently, the recombinant purified antigens human CLEC12A (Sino Biological Inc, cat. Nr. 11896-H07H) and human CD3δε-Fc protein are run over the sensor surface in a concentration range to measure on- and off-rates. After each cycle, the sensor surface is regenerated by a pulse of HCl and the bsAb is captured again. From the obtained sensorgrams, on- and off-rates and affinity values for binding to human CD3 and CLEC12A are determined using the BIAevaluation software, as previously described (e.g., US 2016/0368988).

The T-cell stimulatory capacity of a CLEC12A/CD3 bispecific antibody can be determined in an assay using healthy donor resting T-cells obtained according to the procedure described in WO2014/051433 and US 2016/0368988. For example, a candidate CLEC12A/CD3 bispecific antibody is tested in purified healthy donor resting T cells incubated with cells from the leukemia derived HL60 cell line in 10% fetal bovine serum (FBS) or 10% normal human serum (HS) at an effector: target cell ratio of 10:1 or 5:1 for two days. Results are expressed as the percentage of CD69 positive or CD25 positive cells within the CD4 positive or CD8 positive T cell population.

The ability of a CLEC12A/CD3 bispecific antibody to induce target cell lysis may be tested in an assay using leukemia cells, e.g., HL-60 cells, labeled with carboxyfluorescein diacetate succimidyl ester (CFSE) and co-cultured with T-cells from healthy donor, according to the procedure described in WO2014/051433 and US 2016/0368988. The surviving CFSE-positive cells are quantified by flow cytometry, and the results are expressed as the percentage of specific lysis related to the PBS control condition.

In one aspect, provided is a pharmaceutical composition comprising a CLEC12A/CD3 bispecific antibody and a pharmaceutically acceptable carrier. As used herein, the term "pharmaceutically acceptable" means approved by a government regulatory agency or listed in the U.S. Pharmacopeia or another generally recognized pharmacopeia for use in animals, particularly in humans, and includes any and all solvents, salts, dispersion media, coatings, antibacterial and antifungal agents, isotonic and absorption delaying agents, and the like that are physiologically compatible. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil, glycerol polyethylene glycol ricinoleate, and the like. Water or aqueous solution saline and aqueous dextrose and glycerol solutions may be employed as carriers, particularly for injectable solutions. Liquid compositions for parenteral administration can be formulated for administration by injection or continuous infusion. Routes of administration by injection or infusion include intravesical, intratumoral, intravenous, intraperitoneal, intramuscular, intrathecal and subcutaneous. Depending on the route of administration (e.g., intravenously, subcutaneously, intra articularly and the like) the active compound may be coated in a material to protect the compound from the action of acids and other natural conditions that may inactivate the compound.

Pharmaceutical compositions suitable for administration to human patients are typically formulated for parenteral administration, e.g., in a liquid carrier, or suitable for reconstitution into liquid solution or suspension for intravenous administration. The compositions may be formulated in dosage unit form for ease of administration and uniformity of dosage.

Also included are solid preparations which are intended for conversion, shortly before use, to liquid preparations for either oral or parenteral administration. Such liquid forms include solutions, suspensions and emulsions.

The compositions and methods provided herein are particularly useful for activating a T cell or T cells in a patient. The patient has a cancer or is at risk of having cancer. The latter being patients in which are in remission of a cancer and are at risk of recurrence, relapse or metastasis of the cancer. Accordingly, the compositions and methods may be used in the treatment of various myeloid malignancies, including myeloid leukemias and pre-leukemic diseases of myeloid origin. Accordingly, disease that can be treated according to the methods provided herein include myeloid leukemias (e.g., AML and CIVIL) or pre-leukemic diseases such myelodysplastic syndrome (MDS) (and progression to AML), myelofibrosis (MF) or myeloproliferative neoplasm blast phase (MPN-BP).

As used herein, the bispecific antibody CLEC12A/CD3 bispecific antibody may be combined with another therapeutic molecule. Such combined administration (co-administration) includes simultaneous administration of the CLEC12A/CD3 bispecific antibody and IL-15 moiety in the same or different dosage form, separate administration or sequential administration. Accordingly, in some embodiments, a CLEC12A/CD3 bispecific antibody may be used in a method for activating a T cell in a subject, wherein the CLEC12A/CD3 bispecific antibody is administered simultaneously, separately or sequentially with an IL-15 moiety. In other embodiments, a CLEC12A/CD3 bispecific antibody may be used in the treatment of a cancer in a subject, wherein the CLEC12A/CD3 bispecific antibody may be administered simultaneously, separately or sequentially with an IL-15 moiety.

In other embodiments, a CLEC12A/CD3 bispecific antibody may be for use in the manufacture of a medicament for activating a T cell in a subject, wherein the CLEC12A/CD3 bispecific antibody is administered simultaneously, separately or sequentially with an IL-15 moiety. A product comprising a CLEC12A/CD3 bispecific antibody and an IL-15 moiety may be a combined preparation for simultaneous, separate or sequential use in activating a T cell in a subject. In other embodiments, a CLEC12A/CD3 bispecific antibody may be for use in the manufacture of a medicament for treating a cancer in a subject, wherein the CLEC12A/CD3 bispecific antibody may be administered simultaneously, separately or sequentially with an IL-15 moiety. A product comprising a CLEC12A/CD3 bispecific antibody and an IL-15 moiety may be a combined preparation for simultaneous, separate or sequential use in treating a cancer in a subject.

The IL-15 moiety can be administered according to a suitable dosage, route (e.g., intravenous, intraperitoneal, intramuscular, intrathecal or subcutaneous).

The CLEC12A/CD3 bispecific antibody and IL-15 moiety can be simultaneously administered in a single formulation. Alternatively, the CLEC12A/CD3 bispecific antibody and IL-15 moiety can be formulated for separate administration, wherein they are administered concurrently or sequentially.

In some embodiments, the IL-15 moiety and the CLEC12A/CD3 bispecific antibody are administered simultaneously.

In one embodiment, a subject is administered a single dose of an IL-15 moiety and a single dose of the CLEC12A/CD3 bispecific antibody. In some embodiments, the CLEC12A/CD3 bispecific antibody and IL-15 moiety will be administered repeatedly, over a course of treatment. For example, in certain embodiments, multiple (e.g., 2, 3, 4, 5, 6, 7, 8, 9, 10 or more) doses of an IL-15 moiety and multiple (e.g., 2, 3, 4, 5, 6, 7, 8, 9, 10 or more) doses of a CLEC12A/CD3 bispecific antibody are administered to a subject in need of treatment.

In some embodiments, administrations of an IL-15 moiety and a CLEC12A/CD3 bispecific antibody may be done weekly, in which regimen, they may be administered on the same day (e.g., simultaneously), or one after the other (e.g., one or more minutes, hours or days before or after one another). When administered separately, the CLEC12A/CD3 bispecific antibody and IL-15 moiety may be, but are not necessarily administered according to the same administration (i.e., dosing) protocol. A therapeutically effective dose of the IL-15 moiety may be administered either more or less frequently the CLEC12A/CD3 bispecific antibody. In certain embodiments, administration of each dose of the IL-15 moiety and the CLEC12A/CD3 bispecific antibody may be on the same day, or alternatively, the IL-15 moiety may be administered 1 or more days before or after the CLEC12A/CD3 antibody.

For convenience, the total daily dosage may be divided and administered in portions during the day if desired. Intermittent therapy (e.g., one week out of three weeks or three out of four weeks) may also be used.

In some embodiments, the IL-15 moiety used in the methods provided herein is recombinant human IL-15 (rhIL-15). In certain embodiments, the rhIL-15 is administered at doses of about 0.125 µg/kg per day to 2.0 µg/kg per day. In certain embodiments, the rhIL-15 is administered at 0.125, 0.25, 0.5, 1.0 or 2.0 µg/kg per day. In certain embodiments, the rhIL-15 is administered by intravenous bolus. In other embodiments, the rhIL-15 is administered by continuous intravenous infusion (CIV). In certain embodiments, the rhIL-15 is administered by CIV for between 2 to 10 days, 5 to 10 days, or 7 to 10 days. In one embodiment, the rhIL-15 is administered by CIV for 10 days. In related embodiments, the rhIL-15 is administered in treatment cycle of between about 30 and 60 days, in which the rhIL-15 is administered by CIV for the first 5 to 10 days of each cycle.

In some embodiment, the IL-15 moiety administered according to the methods provided herein is a soluble IL-15 receptor or receptor fragment (sIL-15Ra). In other embodiments, the IL-15 moiety is a complex comprising IL-15 and sIL-15Ra, for example, as described in U.S. Pat. Nos. 9,255,141 and 9,328,159. In certain embodiments, the IL-15/IL-15Ra complex is administered at a dose of approximately 0.1 µg/kg to approximately 20 µg/kg, approximately 10 µg/kg to approximately 20 µg/kg, approximately 20 µg/kg to approximately 40 µg/kg, or approximately 25 µg/kg to 50 µg/kg to a subject.

In certain embodiments, the IL-15 moiety is an IL-15/IL-15Ra which is administered subcutaneously. In some embodiments, the IL-15/IL-15Ra complex is administered at a frequency of every day, every other day, every 3, 4, 5, 6 or 7 days. In certain embodiments, the IL-15/IL-15Ra is administered 1, 2, 3, 4, 5, 6 or 7 days per week. In certain embodiments, the dose of the first cycle and each subsequent cycle is 0.1 µg/kg to 1 µg/kg, 1 µg/kg to 5 µg/kg, or 5 µg/kg to 10 µg/kg. In another embodiment, the first dose of the first cycle and each subsequent cycle is 0.1 µg/kg to 0.5 µg/kg, 1 µg/kg to 2 µg/kg, 1 µg/kg to 3 µg/kg, 2 µg/kg to 5 µg/kg, or 2 µg/kg to 4 µg/kg. In another embodiment, the dose of the first cycle and each subsequent cycle is 0.1 µg/kg, 0.25 µg/kg, 0.5 µg/kg, 1 µg/kg, 1.25 µg/kg, 1.5 µg/kg, 1.75 µg/kg, 2 µg/kg, 2.25 µg/kg, 2.5 µg/kg, 2.75 µg/kg, 3 µg/kg, 3.25 µg/kg, 3.5 µg/kg, 4 µg/kg, 4.25 µg/kg, 4.5 µg/kg, 4.75 µg/kg, or 5 µg/kg. In one embodiment, the IL-15/IL-15Ra complex is administered according to a 28 day cycle in which the IL-15/IL-15Ra complex is administered subcutaneously three time per week for two consecutive weeks.

In still other embodiments, the IL-15 moiety used in the methods provided herein is a long-acting form of IL-15, for example, a conjugate of IL-15 and a water soluble polymer as described, for example, in WO 2015815373. One of ordinary skill in the art can determine the quantity of a long-acting, IL-15 agonist that is sufficient to provide clinically relevant agonist activity at the IL-15 receptor ("IL-15R"). In some embodiments, the IL-15 polymer conjugate is administered at a dose of from about 0.001 mg/kg to about 10 mg/kg, preferably from about 0.001 to about 5 mg/kg. In certain embodiments, the IL-15 polymer conjugate is administered at a dose of about 0.03 mg/kg to about 3 mg/kg. In certain embodiments, the IL-15 polymer conjugate is administered at a dose of about 0.03 mg/kg, about 0.1 mg/kg, about 0.3 mg/kg or about 3.0 mg/kg. In other embodiments, the IL-15 polymer conjugate is administered at a dose of about 0.0025 mg/kg, about 0.008 mg/kg, about 0.01 mg/kg, about 0.025 mg/kg, 0.05 mg/kg or about 0.25 mg/kg.

The treatment method described herein is typically continued for as long as the clinician overseeing the patient's care deems the treatment method to be effective, i.e., that the patient is responding to treatment. Non-limiting parameters that indicate the treatment method is effective may include one or more of the following: decrease in tumor cells; inhibition of tumor cell proliferation; tumor cell elimination;

progression-free survival; appropriate response by a suitable tumor marker (if applicable); increased number of NK (natural killer) cells; increased number of CLEC12A specific T cells; and increased number of CLEC12A specific memory T cells.

With regard to the frequency of administering the CLEC12A/CD3 bispecific antibody, one of ordinary skill in the art will be able to determine an appropriate frequency. For example, a clinician can decide to administer the CLEC12A/CD3 bispecific antibody relatively infrequently (e.g., once every two weeks) and progressively shorten the period between doses as tolerated by the patient. When an IL-15 moiety is administered, the frequency for these agents can be determined in a similar fashion. Exemplary lengths of time associated with the course of therapy in accordance with the claimed method include: about one week; two weeks; about three weeks; about four weeks; about five weeks; about six weeks; about seven weeks; about eight weeks; about nine weeks; about ten weeks; about eleven weeks; about twelve weeks; about thirteen weeks; about fourteen weeks; about fifteen weeks; about sixteen weeks; about seventeen weeks; about eighteen weeks; about nineteen weeks; about twenty weeks; about twenty-one weeks; about twenty-two weeks; about twenty-three weeks; about twenty four weeks; about seven months; about eight months; about nine months; about ten months; about eleven months; about twelve months; about thirteen months; about fourteen months; about fifteen months; about sixteen months; about seventeen months; about eighteen months; about nineteen months; about twenty months; about twenty one months; about twenty-two months; about twenty-three months; about twenty-four months; about thirty months; about three years; about four years; about five years; perpetual (e.g., ongoing maintenance therapy). The foregoing duration may be associated with one or multiple rounds/cycles of treatment.

The efficacy of the treatment methods provided herein can be assessed using any suitable means. In one embodiment, the clinical efficacy of the combination treatment is analyzed using AML blast reduction in the bone marrow as an objective response criterion. Patients, e.g., humans, treated according to the methods disclosed herein preferably experience improvement in at least one sign of cancer. In some embodiments, one or more of the following can occur: the number of cancer cells can be reduced; cancer recurrence is prevented or delayed; one or more of the symptoms associated with cancer can be relieved to some extent. In addition, in vitro assays to determine the T cell mediated target cell lysis (as described in WO2017/010874) can be performed with AML tumor blasts isolated from the subject.

In some embodiment, the tumor cells are no longer detectable following treatment as described herein. In some embodiments, a subject is in partial or full remission. In certain embodiments, a subject has an increased overall survival, median survival rate, and/or progression free survival.

The treatments of the present invention (e.g., CLEC12A/CD3 bispecific antibody) or the combination treatment with an IL-15 moiety, may also be used in conjunction with other well-known therapies that are selected for their particular usefulness against the cancer that is being treated. Combinations of the instant invention may alternatively be used sequentially with known pharmaceutically acceptable agent(s) when appropriate.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

All documents and references, including Genbank entries, patents and published patent applications, and websites, described herein are each expressly incorporated herein by reference to the same extent as if were written in this document in full or in part.

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

For the purpose of clarity and a concise description features are described herein as part of the same or separate embodiments, however, it will be appreciated that the scope of the invention may include embodiments having combinations of all or some of the features described.

EXAMPLES

Example 1

Materials and Methods
Flow Cytometry

Flow cytometry was performed using a Coulter FC500, Cyan-ADP, Gallios or NAVIOS™ flow cytometer (Beckman Coulter) or FACS CantoA (BD Biosciences). Data were analysed using Flowjo software (TreeStar Inc) or Kaluza Software® (Beckman Coulter). Blasts were defined as SSC+/−CD45DIM and/or CD45POS cells excluding lymphocytes based on CD45/SSC and CD3 (for T cells).

1. The specific binding pattern of antibody MF4327xMF5196 versus isotype control IgG on cell lines was evaluated with non-conjugated antibodies visualized with an anti-human IgG-PE antibody.

2. The specific binding pattern of antibody MF4327xMF5196 bispecific antibody versus isotype control IgG in healthy donor-derived peripheral blood samples was tested using Oregon Green-conjugated IgG batches in combination with a) CD1c-PE, CD19-ECD, CD3-PECY5, CD56-PECY7 (Beckman Coulter), CD8-AF700, CD4-Pacific blue, CD45-Krome orange; or b) CD303-PE, CD304-PE, CD14-ECD, CD33-PECY5, CD16-PECY7 and CD45-Krome orange.

3. The specific binding pattern of antibody MF4327xMF5196 bispecific antibody versus isotype control IgG in the CD34POS fraction of healthy donor-derived bone marrow samples was tested using PE-conjugated IgG batches in combination with Lineage (CD3, CD14, CD16, CD19, CD20, CD56)-FITC, CD38-ECD, 7AAD, CD34-

PECY7, CD10-APC, CD45RA-AF700, CD135a-BV421, CD90-BV510 and CLEC12A-PE (R&D Systems).

4. T cell activation in cytotoxicity assay with HL60 cells was determined using CD25-PE, 7AAD, CD3-PECY7, CD69-APC, CD8-AF700 and CD4-BV421.

5. Monocyte cytotoxicity was quantified using CD14-FITC, CD16-PE, CD19-ECD, 7AAD, CD3-PECY7, CD69-APC and CD8-AF700.

6. To quantify T cell proliferation, T cells were visualized with 7AAD, CD3-PECY7, CD8-AF700 and CD4-BV421.

7. Cytotoxicity of CD34POS bone marrow progenitor cells was quantified using a) CLEC12A-PE (Biolegend), 7AAD, CD34-PECY7, CD10-APC-AF750 and CD5-BV421; and b) with CD90-FITC, CLEC12A-PE (Biolegend)/IgG2a-PE, CD38-ECD, 7AAD, CD34-PECY7, CD10-APC, CD45RA-AF700, CD123-BV421 or CD135a-BV421 and Lineage (CD3, CD14, CD16, CD19, CD20, CD56)-BV510.

8. CLEC12A expression on AML blasts used for cytotoxicity assays with AML blasts and purified T cells was quantified using a) CLEC12A-PE (R&D Systems), CD14-ECD, CD33-PECY5, CD38-PECY7, CD117-APC, CD19-AF700, CD34-BV421 and CD45-krome orange; orb) CLEC12A-PE (R&D Systems), CD19-ECD, CD3-PECY5, CD56-PECY7 (Biolegend), CD8-AF700, CD4-BV421 and CD45-krome orange.

9. Efficacy of antibody MF4327xMF5196 in cytotoxicity assays using AML blasts and purified T cells was quantified using a) CD197-AF488, CD4-PE, CD45RO-ECD, 7AAD, CD3-PECY7, CD8-AF700 and CD45RA-Pacific blue; and b) CD25-PE, CD4-ECD, 7AAD, CD3-PECY7, CD117-APC, CD8-AF700, CD34-BV421 and CD45-krome orange.

10. CLEC12A expression on AML blasts was determined using a) (1,000 ng/mL condition) CD14-FITC, CLEC12A-PE (R&D Systems)/IgG2b-PE, CD34-ECD, 7AAD, CD33-PECY7, CD8-AF700, CD4-BV421 and CD45-krome orange; orb) (200 ng/mL condition) CD14-FITC, CLEC12A-PE (R&D Systems), CD34-ECD, CD4-PECY5.5, CD117-APC, CD8-AF700, CD33-APC AF750 and CD45-krome orange.

11. Efficacy of antibody MF4327xMF5196 in primary AML blast samples was assessed using a) (1,000 ng/mL condition) CD14-FITC, CD34-ECD, 7AAD, CD33-PECY7, CD3-APC, CD8-AF700, CD4-BV421 and CD45-krome orange; orb) (200 ng/mL condition) CD3-FITC, 7AAD, CD4-PECY7, CD8-AF647, CD45RA-AF700, CD33-APC AF750 and CD45-krome orange.

Bispecific Antibodies

Antibody MF4327xMF5196 as used in the examples and the figures referred to in the examples is a full length human IgG1 bispecific antibody specific for CLEC12A and CD3 with a common light chain variable region of IgVk1-39*01 of SEQ ID: NO 56 in the sequence listing summary. It has the heavy chain variable region of MF4327 and the heavy chain variable region of MF5196 depicted in the sequence listing summary. The constant part of the antibody can be effector function silenced or not as indicated. The negative control antibodies were a cLC monospecific antibody against tetanus toxoid (TTxTT IgG, isotype control (de Kruif, Kramer et al. 2009)) and a cLC bispecific antibody against tetanus toxoid and CD3 (MockxCD3 or TTxCD3 IgG, using the same CD3 Fab as in antibody MF4327XMF5196); the positive control antibody was a bivalent cLC monospecific antibody against CD3 (CD3xCD3, also using the same CD3 Fab as in antibody MF4327xMF5196). In initial batches of the bispecific antibodies, electrostatically engineered heavy chains were used for transient production, resulting in bispecific IgG1 with >95% purity (Gunasekaran, Pentony et al. 2010). Later batches were produced using heavy chain Fc engineering wherein proprietary mutations involving charged residues at the CH3 interface were introduced (De Nardis, Hendriks et al. 2017). Unless otherwise specified, the IgG batches of antibody MF4327xMF5196, MockxCD3 and TTxTT IgG lacked Fc effector function upon introduction of changes in the CH2 regions.

Affinity Measurement

Antibody MF4327xMF5196 was immobilized on a CM5 chip (GE Healthcare) through a mouse anti-human IgG monoclonal antibody (BD Biosciences). Recombinant purified CLEC12A-His (Sino Biologicals) or recombinant CD3δε-Fc protein was subsequently run over the surface using a Biacore T100 instrument (GE Healthcare).

In Vivo Pharmacokinetic Study

C57Bl/6J mice received a single intravenous dose of 1 mg/kg antibody MF4327xMF5196. Antibody MF4327xMF5196 serum levels were quantified at various time points using an anti-human IgG ELISA (ZeptoMetrix).

Cell Lines

HL60 cells (DSMZ) were cultured in IMDM (GIBCO Invitrogen, 21980-065) containing 2 mM 1-glutamine and 10% FBS (Integro). CHO-K1 (DSMZ), Jurkat E6.1 (LGC) and J.RT-T3.5 (LGC) cell lines were maintained in DMEM/F12 (GIBCO Invitrogen, 11320-033) supplemented with 2 mM 1-glutamine and 10% FBS (ThermoFisher Scientific). The CLEC12A-CHO-K1 cell line was generated by stable integration of pcDNA3.1+ vector (ThermoFisher Scientific) encoding human CLEC12A.

Clinical Samples

AML patient samples (Table III) and healthy donor bone marrow were obtained in accordance with the Declaration of Helsinki and RUMC institutional guidelines and regulations. For storage in liquid nitrogen, cells were resuspended in IMDM medium containing 7% dimethyl sulfoxide (DMSO; Sigma-Aldrich, W387509) and 10% foetal bovine serum (FBS, Integro). Upon thawing, cells were incubated in 10% human serum (HS, PAA laboratories) containing 250 µg/mL DNAse (Roche, 11284932001) and 1.25 mM $MgCl_2$ for 10 min. Subsequently, cells were washed with excess volumes of medium.

Cytotoxicity Assay with Purified T Cells

Human peripheral blood mononuclear cells (PBMCs) were isolated from peripheral blood (PB) collected from healthy donors or AML patients by density gradient centrifugation (see Table III for patient characteristics). $CD3^{POS}$ T cells were purified from freshly isolated or cryopreserved PBMCs by negative selection by using magnetic cell sorting (MACS, Miltenyi, 130-096-535). Cytotoxicity assays were performed in IMDM supplemented with 10% AB+HS (Sanquin) in 96-well plates (Nunc™, ThermoFisher Scientific). Unless otherwise specified, $10^5$ T cells were used. CFSE-labelled HL60 or primary AML blast target cells were used (ThermoFisher Scientific, C11-57). Prior to CFSE labelling, AML blasts were pre-cultured overnight in assay medium supplemented with 100 ng/mL GM-CSF (Immunotools, 11343125), 100 ng/mL G-CSF (Amgen Inc, Neupogen®), 50 ng/mL IL-3 (Cellgenix), 25 ng/mL SCF (Immunotools, 11343325) and 20 ng/mL Flt3L (Immunotools, 11343305). Subsequently, T cells and target cells were co-cultured in the same cytokine-supplemented assay medium in the presence of antibody MF4327xMF5196 or control IgGs. After 24-72 hours, T cell activation and the number of remaining $CFSE^{POS}$ target cells were quantified by flow cytometry (for gating strategy see FIG. 7). The percentage of specific lysis was calculated as follows: Specific lysis (%)=100−[(100× target cell number in condition with IgG)/(average target cell number in condition without IgG)].

PBMC-Based Monocyte Cytotoxicity Assay

PBMCs ($2\times10^5$) were incubated in IMDM with 10% AB+HS for 48 hours in the presence of antibody MF4327xMF5196 or control IgGs. Prior to harvesting, the assay plates were centrifuged (500 g, 5 minutes) to collect supernatant for cytokine quantification. After a subsequent incubation at 2-8° C. for 1 hour, cells were stained in the assay medium without washing. The specific lysis of monocytes, B cells and natural killer (NK) cells was quantified by flow cytometry in a fixed volume collected from each assay well (FIG. 8).

T Cell Proliferation Assay

CFSE-labelled $CD3^{POS}$ T cells were co-cultured with $CD14^{POS}$ MACS-purified (Miltenyi, 130-050-201) autologous monocytes in IMDM with 10% AB+HS with or without test IgG at an E:T ratio of 5:1. After 5 days, the fraction of proliferating T cells was visualized as $CFSE^{LOW}$ T cells by flow cytometry.

Cytokine Analysis

The levels of IL-1β, IL-2, IL-4, IL-5, IL-6, IL-8, IL-10, GM-CSF, TNF-α and IFN-γ in culture supernatants were measured using the Luminex® platform (Life Technologies, LHC0001).

Cytotoxicity Assay with Healthy Donor Bone Marrow Cells $CD3^{POS}$ T cells and $CD34^{POS}$ cells were isolated from healthy donor bone marrow mononuclear cells (obtained from orthopaedic patients or purchased from Lonza, 2M-125C) by positive selection using MACS (Miltenyi, 130-046-702 and 130-050-101, respectively). Pre-activated T cells were generated by activating purified T cells for 6 days in plates pre-coated with anti-CD3 (1 μg/mL, BD Bioscience, 555329) and anti-CD28 (2 μg/mL, BD Bioscience, 555725) in IMDM supplemented with 10% HS A+(Sanquin blood bank) and 30 IU/mL IL-2 (Chiron, Proleukin®) followed by overnight rest in plates with 30 IU/mL IL-2. On the next day, pre-activated T cells were co-cultured with autologous CD34POS cells at a 10:1 E:T ratio in IMDM supplemented with 10% A+HS in 96-well plates (Corning Costar, 3799) in the presence of antibody MF4327xMF5196 or control concentration. After 16 hours, impact of antibody MF4327xMF5196 was quantified by flow cytometry for various $CD34^{POS}$ progenitor populations and colony forming unit (CFU) assays as described below. For quantification by flow cytometry, flow count fluorospheres (Beckman Coulter, 7547053) were used. For gating strategy see FIGS. 10 and 11.

Colony Forming Unit (CFU) Assays

Co-cultures of T cells and $CD34^{POS}$ cells were seeded upon washing in MethoCult GF H84435 (Stemcell Technologies, 84435) for analysis of erythroid and mono-myelocytic colony outgrowth and MegaCult™-C (complete kit with cytokines (04971) with added human low-density lipoproteins (40 μg/mL, 02698), both from Stemcell Technologies) for analysis of megakaryocyte colony formation according to the manufacturer's instructions. For both the MethoCult and MegaCult™-C assays, co-cultures were seeded at two different concentrations based on the $CD34^{POS}$ cell count in the no-IgG condition, and an equal volume of cells was seeded of the antibody MF4327xMF5196- and control IgG-treated co-cultures. For the MethoCult assay, $1\times10^3$ and $5\times10^2$ $CD34^{POS}$ cells of the non-IgG condition were seeded in triplicate in 35 mm culture dishes (Corning, 430165), and for the MegaCult-C assay, $7.5\times10^3$ and $2.5\times10^3$ $CD34^{POS}$ cells were seeded per chamber of a double-chamber culture slide and two slides prepared per condition. The number of erythroid, mono-myelocytic and megakaryocyte colonies were scored after 13-15 day culture, and subsequently the MethoCult cultures were harvested and analysed by flow cytometry for monocytic and myelocytic markers.

Cytotoxicity Assay with Primary AML Samples

Primary AML patient samples ($5\times10^5$ cells) were cultured in the presence of antibody MF4327xMF5196 or control bispecific IgG in IMDM containing 10% AB+HS, 2.5 ng/mL GM-CSF, 12.5 ng/mL G-CSF (Neupogen, Amgen), 6.25 ng/mL IL-3 (Immunotools, 11340035), 3.0 ng/mL SCF and 2.5 ng/mL Flt3L. After 24 hours, 20 ng/mL IL-15 (Miltenyi, 130-095-766) was added to the culture. After 10 days, AML blast lysis and T cell expansion was quantified by flow cytometry.

Antibody MF4327xMF5196 Dosing Regimen in Human AML Patients.

The MF4327xMF5196 antibody is being explored as a single agent in a first in human study using a dose escalation in cohorts of 3-6 patients. Patients received the antibody with a regimen of administration designed to provide an efficacious and safe dose. The antibody was administered in infusions of 2-4 hours. The treatment was planned with time intervals. The regimen of administration was designed to prevent and minimize the severity and incidence of Cytokine release syndrome (CRS).

The treatment regimen has components that are applied at the first cycle (during the first 28 days). The priming dose (C1D1); a step-up and fixed full dosing (C1D4, C1D8, C1D15) and the use of pre-medication. A priming dose: the first administration (C1D1) is given with a low dose (1 mg, 3 mg, 5 mg). Step-up dosing: subsequent doses after C1D1 are given with gradual increments of the dose until the planned full dose is given. The step-up dosing includes more frequent administration during the first week. In the first week the treatment is given every 3 days (D1-D4-D8) and then the treatment is given every 7 days (on weekly basis). Fixed full dosing: the full dose is given at day 15 and from there the treatment is given at a fixed full dose. Pre-medication: given prior to each MF4327xMF5196 antibody dose includes acetaminophen and anti-histamines (anti-H1).

After the first cycle, the treatment continues with full doses given on a weekly regimen (days 1-8-15-22). The infusion is always given in 2-4 hours with pre-medications.

In one cohort, patients received a priming dose of 1 mg on day 1, followed by step-up doses of 3 mg on day 4 and 15 mg on day 8, and a full dose of 25 mg on day 15.

In another cohort, patients received a priming dose of 3 mg on day 1, followed by step-up doses of 10 mg on day 4 and 25 mg on day 8, and a full dose of 40 mg on day 15.

In a further cohort, patients received a priming dose of 5 mg on day 1, followed by step-up doses of 15 mg on day 4 and 25 mg on day 8, and a full dose of 60 mg on day 15.

The patient's response to the treatment was followed, including analysis of cytokine levels before each dose, and 4 hours and 24 hours after the end of infusion.

Results

Antibody MF4327xMF5196 Binds Specifically to $CLEC12A^{POS}$ and $CD3^{POS}$ Cells within the Normal Hemopoietic Compartment Antibody MF4327xMF5196 is a T cell-targeting bispecific antibody that has been developed to treat CLEC12a positive cancer cells, such as present in AML. It binds to CD3 on T cells and CLEC12A on the AML blasts and LSCs.

Antibody MF4327xMF5196 is a human full-length IgG1 bispecific antibody based on a common light chain (cLC) bispecific IgG format.

Flow cytometry using tumor cell lines showed that antibody MF4327xMF5196 binds specifically to CLEC12A and CD3 (FIG. 1A). Via its CLEC12A arm, it bound CLEC12A$^{POS}$ HL60 cells as well as CHO-K1 cells transfected with human CLEC12A, but not to parental CHO-K1 cells. Via its CD3 arm, it bound to CD3$^{POS}$ JurkatE6.1 cells, but not to CD3$^{NEG}$ Jurkat J.RT-T3.5 cells.

The affinity of antibody MF4327xMF5196 for its target proteins was 3 nM for CLEC12A and 177 nM for CD3, as determined by surface plasmon resonance technology using recombinant proteins. To investigate whether the engineered Fc region of antibody MF4327xMF5196 has a potential impact on pharmacokinetics (PK), the in vivo half-life of antibody MF4327xMF5196 was determined in C57BL/6J mice and found to be 226 hours (9.4 days). This half-life is within the range of in vivo half-lives typically observed for human IgG1 antibodies in rodents, indicating that the specific design of the human cLC bispecific antibody has no effect on the non-specific elimination pathways for IgG.

Figure 1B:
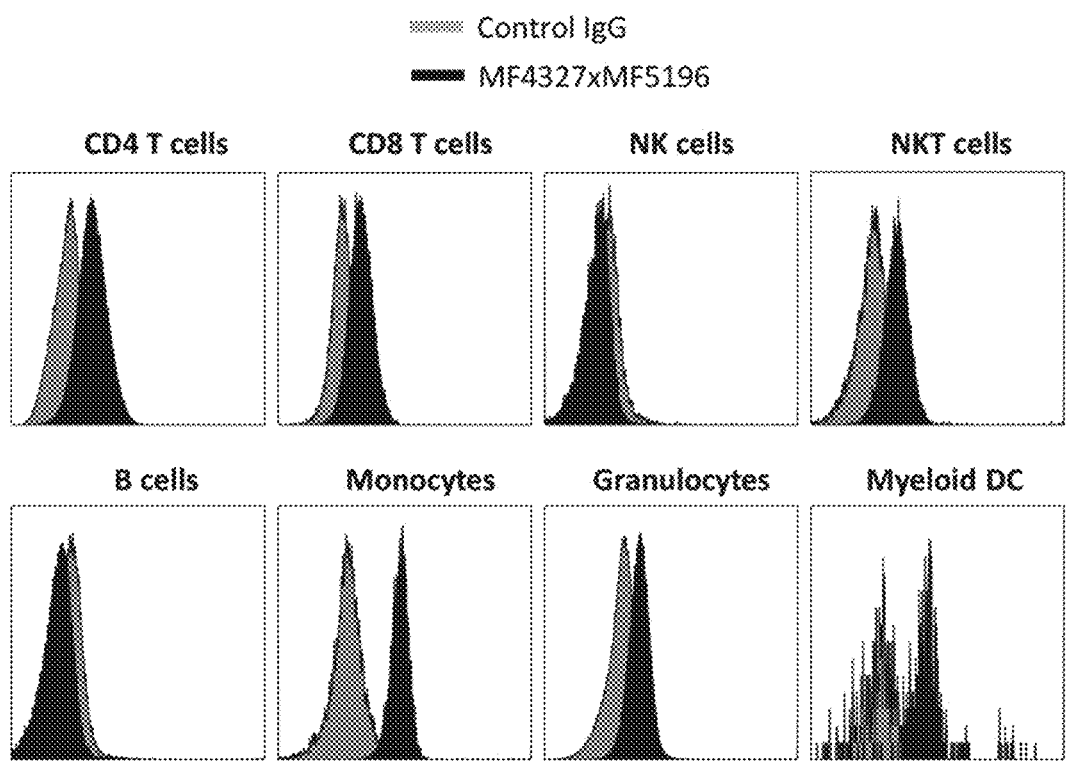
Figure 1C:
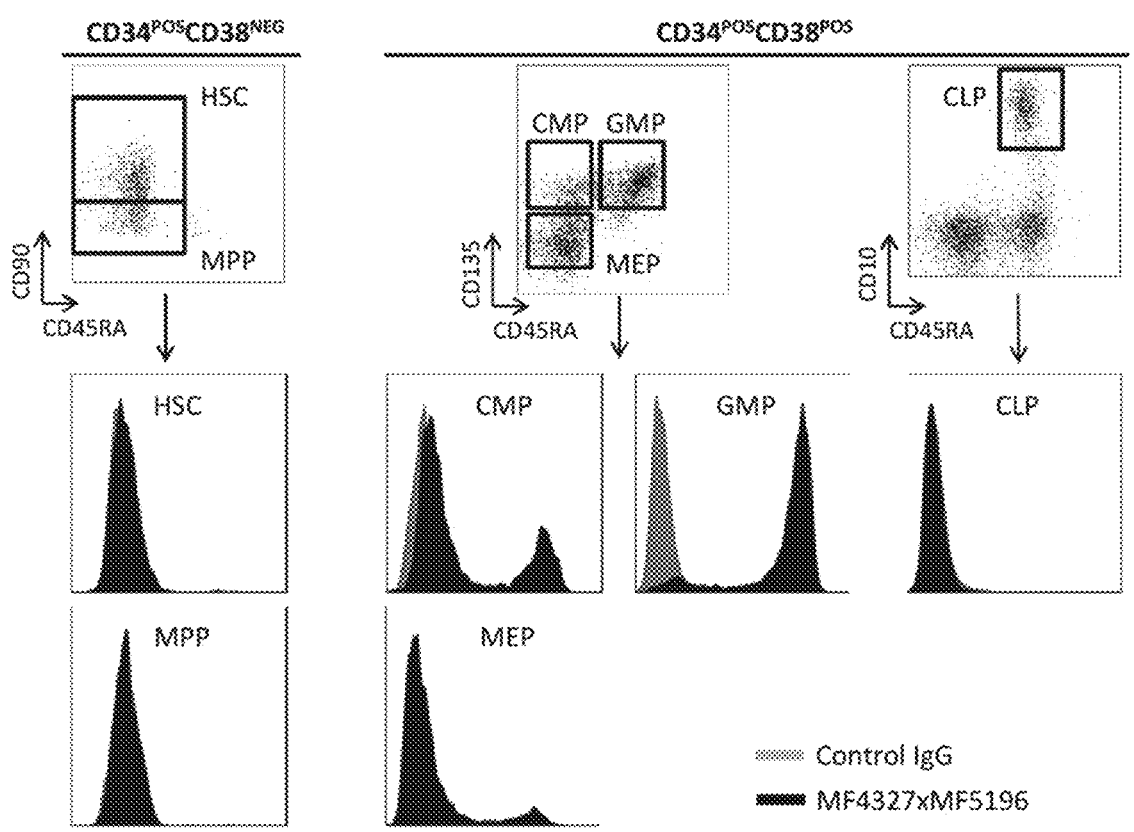

Analysis of the binding profile of antibody MF4327xMF5196 in normal peripheral blood showed that antibody MF4327xMF5196 binds to CD3-expressing CD4$^{POS}$ and CD8$^{POS}$ T cells as well as to CD3$^{POS}$CD56$^{POS}$ NK T (NKT) cells (FIG. 1B). In accordance with a previously reported expression profile for CLEC12A (Bakker, van den Oudenrijn et al. 2004, Marshall, Willment et al. 2004, Lahoud, Proietto et al. 2009), antibody MF4327xMF5196 also bound to monocytes, myeloid dendritic cells (mDC), plasmacytoid dendritic cells (pDC) and granulocytes, but not to natural killer (NK) cells or B cells (FIG. 1B and data not shown). In normal bone marrow, the binding profile of antibody MF4327xMF5196 within the CD34$^{POS}$ progenitor compartment (FIG. 1C) also resembled the reported CLEC12A expression profile (van Rhenen, van Dongen et al. 2007). Antibody MF4327xMF5196 bound uniformly to granulocyte-macrophage progenitor (GMP) cells, whereas it bound only a minor fraction of the common myeloid progenitor (CMP) and megakaryocyte-erythroid progenitor (MEP) subsets. Notably, antibody MF4327xMF5196 binding was not observed within the CD34$^{POS}$CD38$^{NEG}$ compartment, which includes the multipotent progenitors (MPP) and pluripotent hemopoietic stem cells (HSC).

Figure 2A:
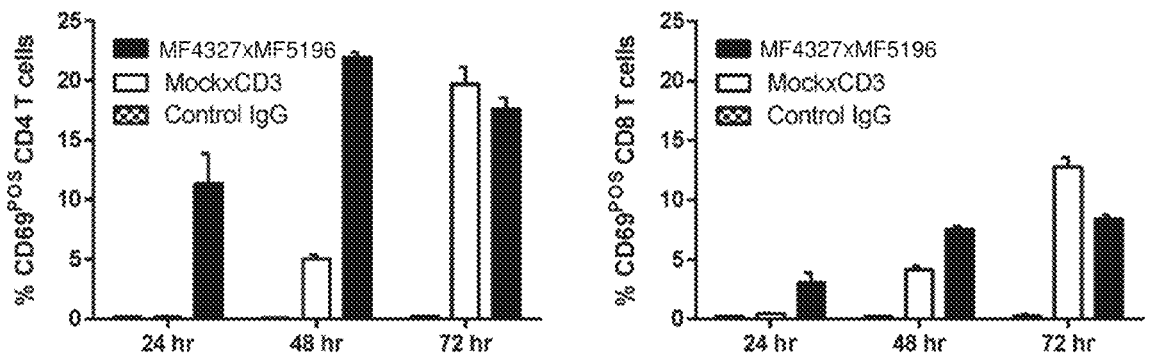
FIG. 2. antibody MF4327xMF5196 mediates CLEC12A-specific activation of T cells and redirects these T cells to induce lysis of a CLEC12A$^{POS}$ HL60 cells. Resting T cells derived from healthy donors were purified by negative selection and co-cultured with CFSE-labelled HL60 cells in the presence of antibody MF4327xMF5196, MockxCD3, control IgG or PBS. (A-B) Cells were co-incubated at an E:T ratio of 5:1 together with indicated IgGs—all with WT Fc effector function—at an IgG concentration of 1000 ng/mL. The capacity of the antibody MF4327xMF5196 prototype with WT Fc effector function to induce T cell activation (A) and target cell lysis (B) was quantified after 24/48/72 hours by flow cytometry relative to the PBS condition. The data shown for representative two healthy donors out of >10 tested. (C-E) Cells were co-incubated at an E:T ratio of 5:1 with indicated IgGs—all with silenced Fc effector function—at a range of IgG concentrations. The capacity of antibody MF4327xMF5196 (with silenced Fc effector function) to induce activation of CD4 and CD8 T cells (C, D) and target cell lysis (E) was quantified after 48 hours by flow cytometry relative to the PBS condition. The data shown are from a representative donor, whereby a total of 6 donors were tested in 3 independent assays.
Figure 2B:
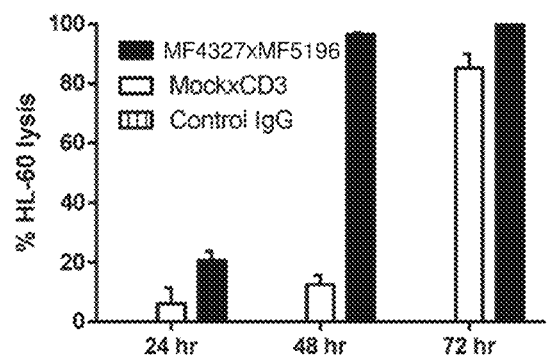

Antibody MF4327xMF5196 Induces CLEC12A-Specific T Cell Activation and Lysis of CLEC12A$^{POS}$ HL60 Cells Next, we determined the capacity of the CLEC12AxCD3 bispecific IgG antibody to induce CLEC12A antigen-specific T cell activation and lysis of CLEC12A$^{POS}$ target cells in a cytotoxicity assay. The effector cells were healthy donor-derived resting T cells and the target cells were CLEC12A$^{POS}$ HL60 cells. In this assay, an MF4327xMF5196 bispecific antibody with a wild-type (WT) Fc region (intact Fc effector function) was compared with MockxCD3 control IgG formatted with a WT Fc region. The MF4327xMF5196 bispecific antibody induced upregulation of CD69 (FIG. 2A) and CD25 (data not shown) on CD4 and CD8 T cells after 24 and 48 hours. T cell-mediated lysis of HL60 cells was already evident after 24 hours and >95% HL60 cell cytotoxicity was measured after 48 hours (FIG. 2B). Target cell lysis correlates to the effector-to-target ratio (E:T ratio) with a maximum lysis at E:T ratios of 5:1 or higher (FIG. 9). Notably, the CLEC12AxCD3-induced lytic activity was CLEC12A antigen-mediated (FIG. 2A, B); only at later time points some T cell activation and HL60 target cell lysis was observed for the MockxCD3 control. Nevertheless, this revealed that the bispecific IgG format with WT Fc could induce Fcγ receptor-mediated T cell activation without the need for CLEC12A binding (FIGS. 2A and B, 72 hours).

Figure 2C:
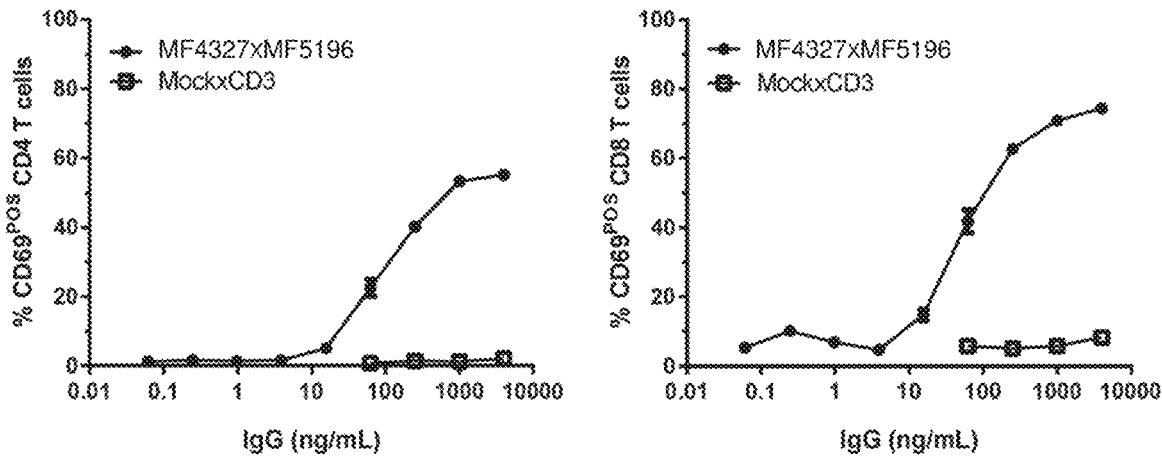
Figure 2D:
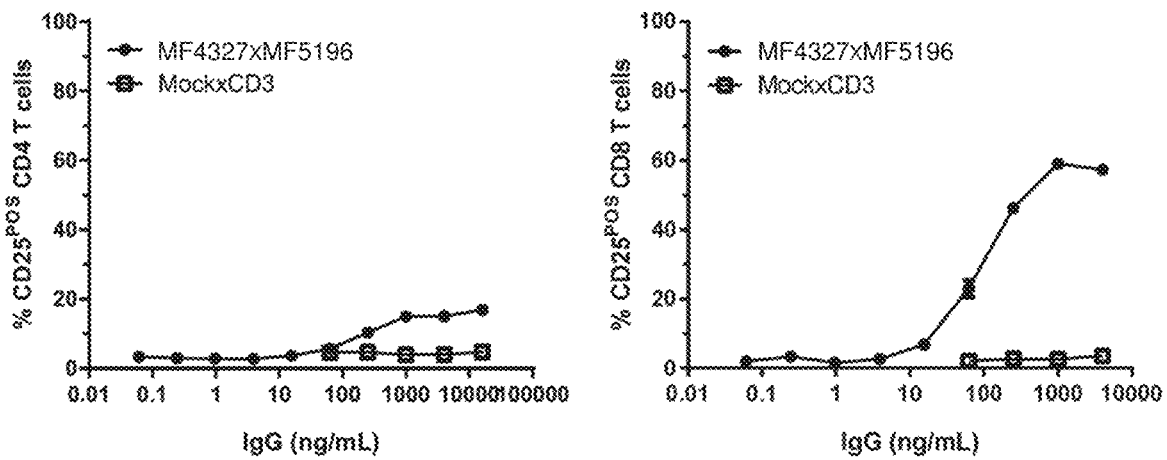
Figure 2E:
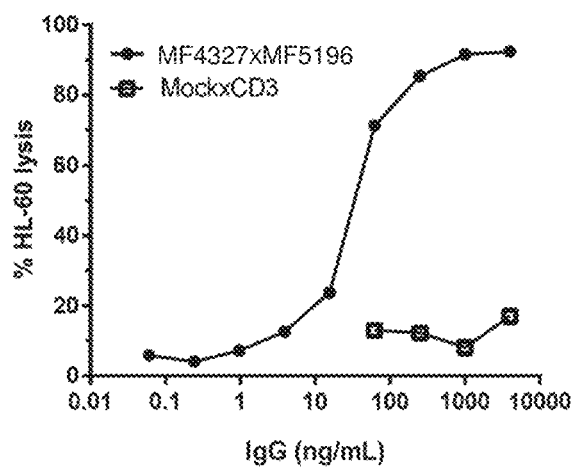

Antibody MF4327xMF5196 with Silenced Fc Effector Function Induces Specific Lysis of CLEC12A$^{POS}$ AML Cell Line To prevent bispecific antibody MF4327xMF5196 from inducing non-specific Fcγ receptor-mediated cell lysis, a bispecific IgG format lacking Fc effector function was generated by introducing changes into the CH2 region of both IgG1 heavy chains. A variety of means of mitigating Fc effector function are known in the art. Binding to CD16, CD32 and C1q, and diminished binding to CD64 >200-fold was accomplished via Fc engineering modifying residues in the CH2 domain. In cytotoxicity assays using normal resting T cells and CLEC12A$^{POS}$ HL60 cells, antibody MF4327xMF5196 induced upregulation of CD69 (FIG. 2C) and CD25 (FIG. 2D) on CD4 T cells and CD8 T cells. The most sensitive read-out for antibody MF4327xMF5196-induced activity was upregulation of CD69 on CD8 T cells with a mean half-maximal effective concentration (EC$_{50}$) of 44 ng/mL (Table I). More importantly, antibody MF4327xMF5196 induced T cell-mediated lysis of HL60 cells with >80% lysis at concentrations of 100 ng/mL and above, and a mean EC$_{50}$ of 68 ng/mL (FIG. 2E, Table I). While activation of CD4 and CD8 T cells by the MockxCD3 antibody with wild-type Fc effector function was already seen at day 2 (FIG. 2A, 1000 ng/mL), no T cell activation was observed with the Fcγ receptor-silenced MockxCD3 antibody after 48 hours, not even at 8000 ng/mL (FIG. 2C-D). All together this shows that the T cell cytotoxicity induced by Fcγ receptor-silenced antibody MF4327xMF5196 (FIG. 2C-E) is CLEC12A antigen-specific.

Collectively, these data demonstrate the capacity of antibody MF4327xMF5196 having reduced Fc effector function to mediate CLEC12A-specific T cell activation and to effectively redirect these T cells to induce lysis of CLEC12A$^{POS}$ HL60 cells.

Figure 3A:
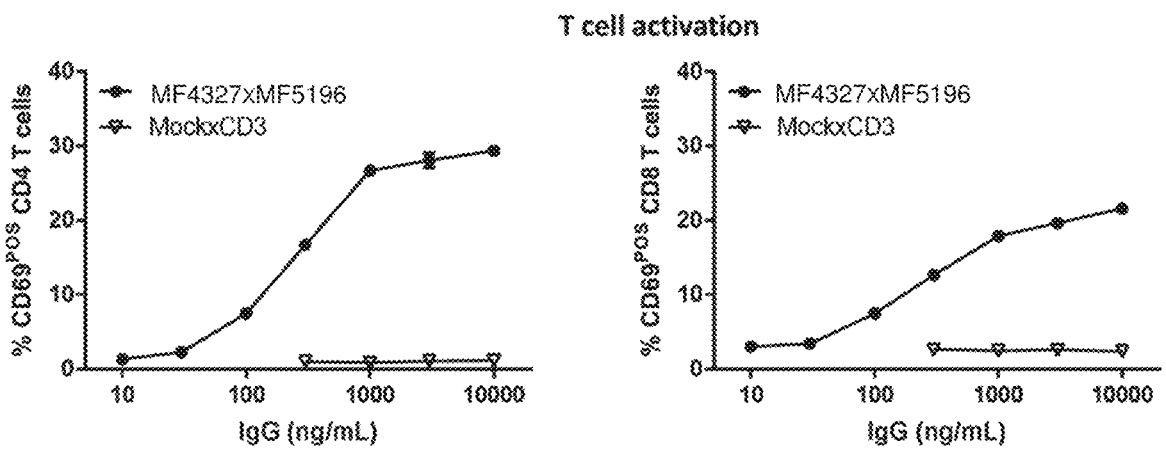
FIG. 3. antibody MF4327xMF5196 induces CLEC12A-mediated lysis of monocytes, and inflammatory cytokine release, and has the capacity to induce CLEC12A-antigen specific T cell proliferation.
Figure 3B:
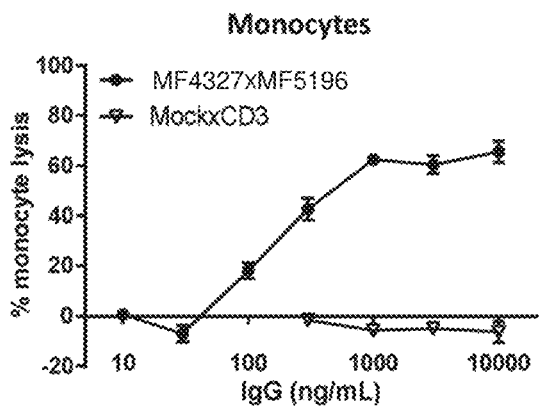
Figure 3C:
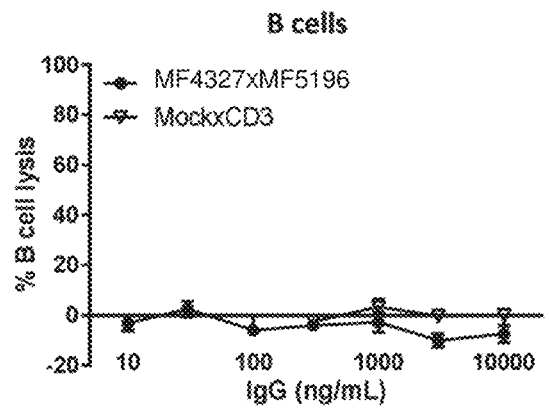

Antibody MF4327xMF5196 Induces Specific Lysis of CLEC12A$^{POS}$ Monocytes by Autologous T Cells The capacity of antibody MF4327xMF5196 to induce redirected lysis of CLEC12A$^{POS}$ monocytes by resting autologous T cells was determined in PBMC cultures. Antibody MF4327xMF5196 induced activation of CD4 T cells and CD8 T cells (FIG. 3A), and lysis of monocytes (from 100 ng/mL, FIG. 3B). Importantly, the antibody MF4327xMF5196-induced activity was CLEC12A-specific as the MockxCD3 control did not induce observable T cell activation or monocyte lysis at concentrations up to 10,000 ng/mL (FIG. 3A-B). Furthermore, the lytic activity of antibody MF4327xMF5196-activated cytotoxic T cells was selective for CLEC12A-antigen expressing cells, as B cell and NK cell fractions were not affected, even at the highest tested antibody MF4327xMF5196 concentrations (FIG. 3C and data not shown).

These data demonstrate that antibody MF4327xMF5196 can efficiently induce CLEC12A-restricted redirected lysis of CLEC12A$^{POS}$ monocytes via re-direction and activation of autologous T cells.

CLEC12A—Specific Induction of Cytokine Release and T Cell Proliferation

Figure 3D:
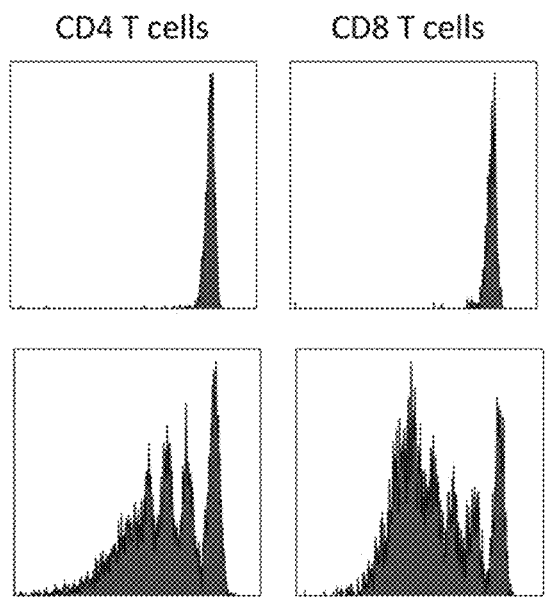

Next, the capacity of antibody MF4327xMF5196 to induce T cell proliferation was studied upon co-incubation of monocytes with autologous resting T cells. Antibody MF4327xMF5196 efficiently induced CLEC12A-specific proliferation of both CD4 and CD8 T cells at 100 and 1,000 ng/mL (FIG. 3D). After 5 days of co-culture, the MockxCD3 control did not induce any T cell proliferation, proving once more that antibody MF4327xMF5196 function is CLEC12A-specific.

Figure 3E:
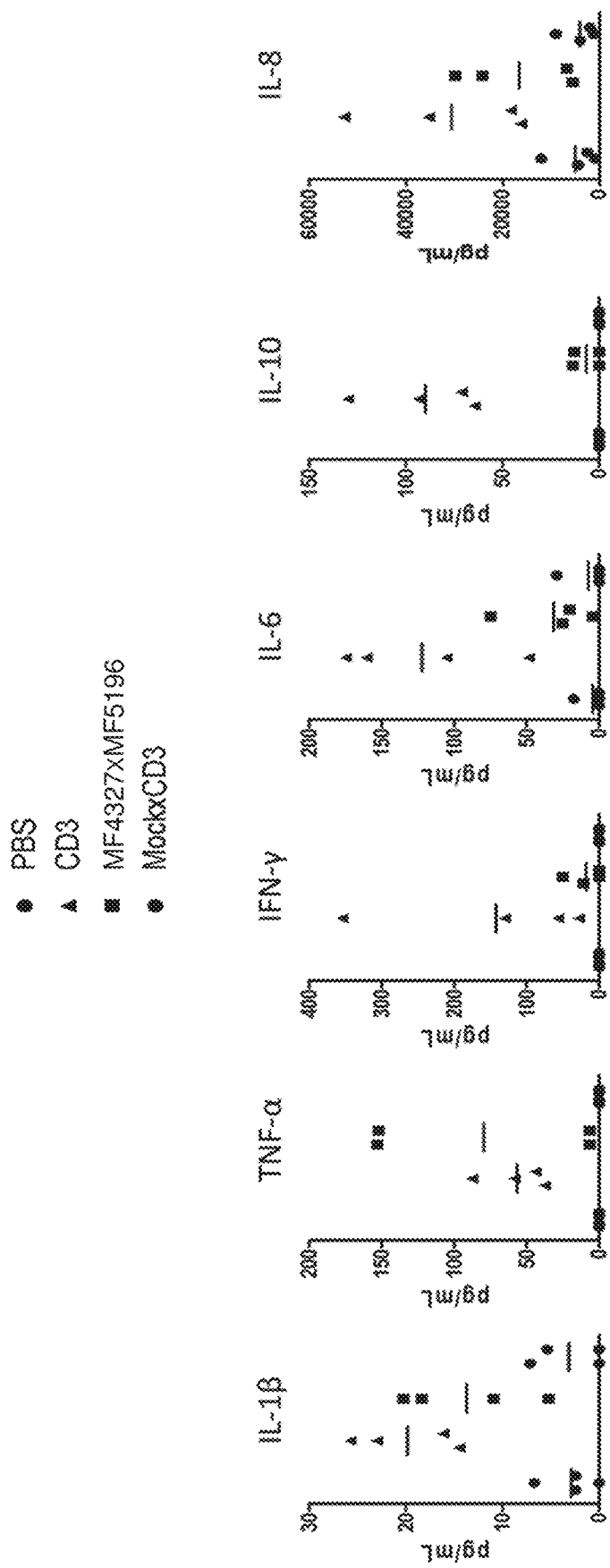

Next, levels of cytokines were measured in these PBMC cultures after 48 hours of antibody MF4327xMF5196 exposure at 1,000 ng/mL. Antibody MF4327xMF5196 induced the release of IL-1β, TNF-α, IFN-γ, IL-6 and IL-10 in the range of 10-200 μg/mL, and IL-8 release in the range of 10,000-30,000 μg/mL (FIG. 3E). In general, antibody MF4327xMF5196-induced cytokine levels were lower than those obtained after stimulation with an anti-CD3 bivalent monospecific antibody. The antibody MF4327xMF5196-induced cytokine release was CLEC12A-specific as cytokine release in the presence of the MockxCD3 control was absent or limited.

These data demonstrate that antibody MF4327xMF5196 can induce autologous T cells to proliferate and release cytokines upon co-incubation with CLEC12A$^{POS}$ monocytes.

Figure 4A:
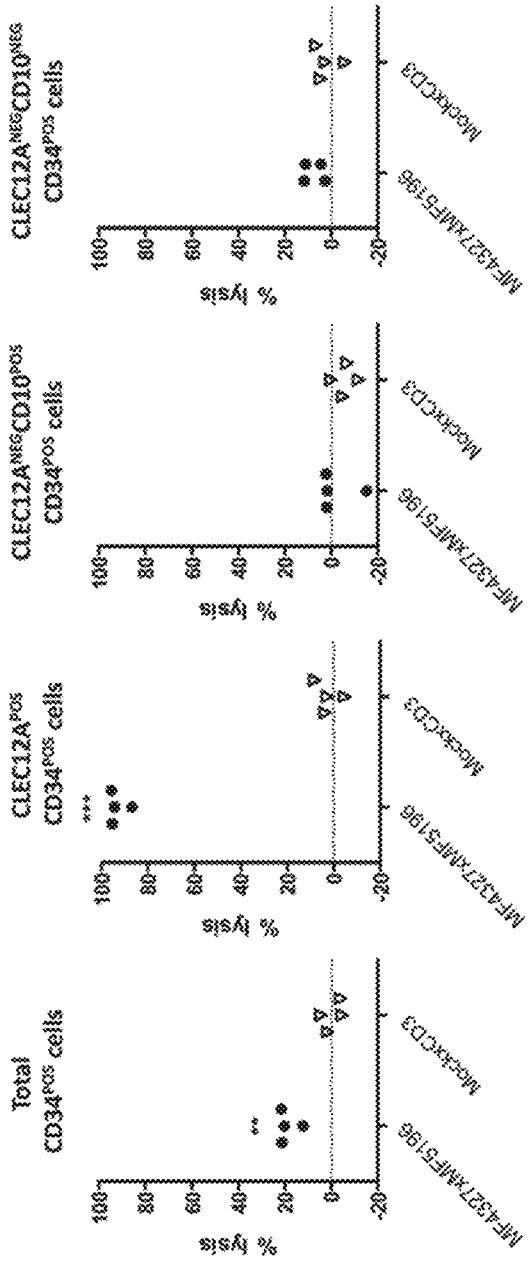
Figure 4B:
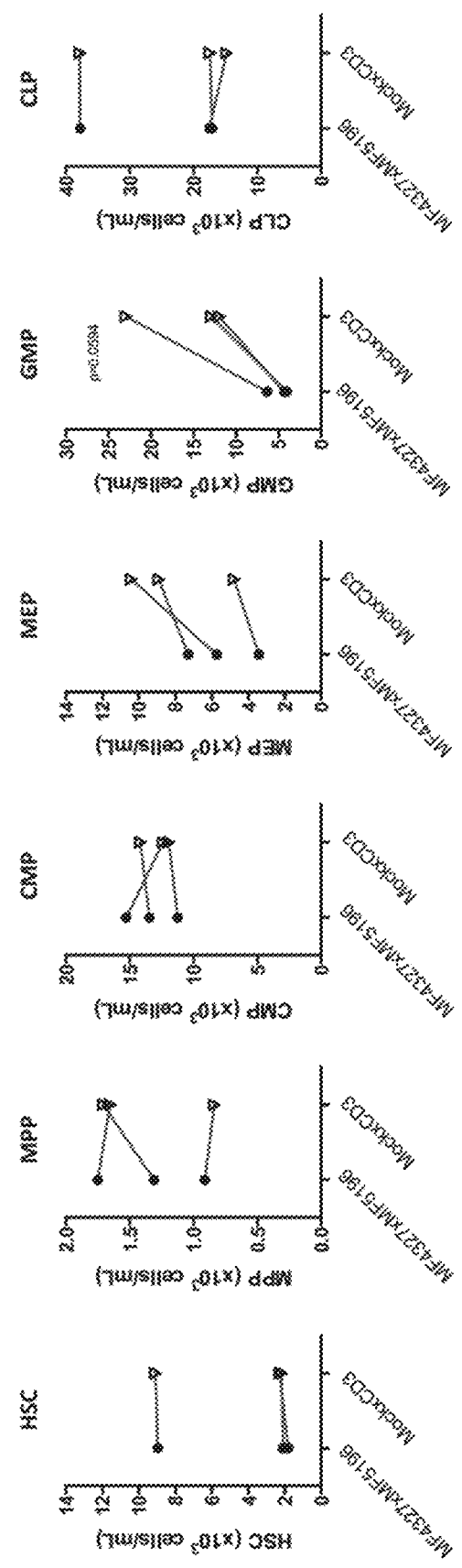
Figure 4C:
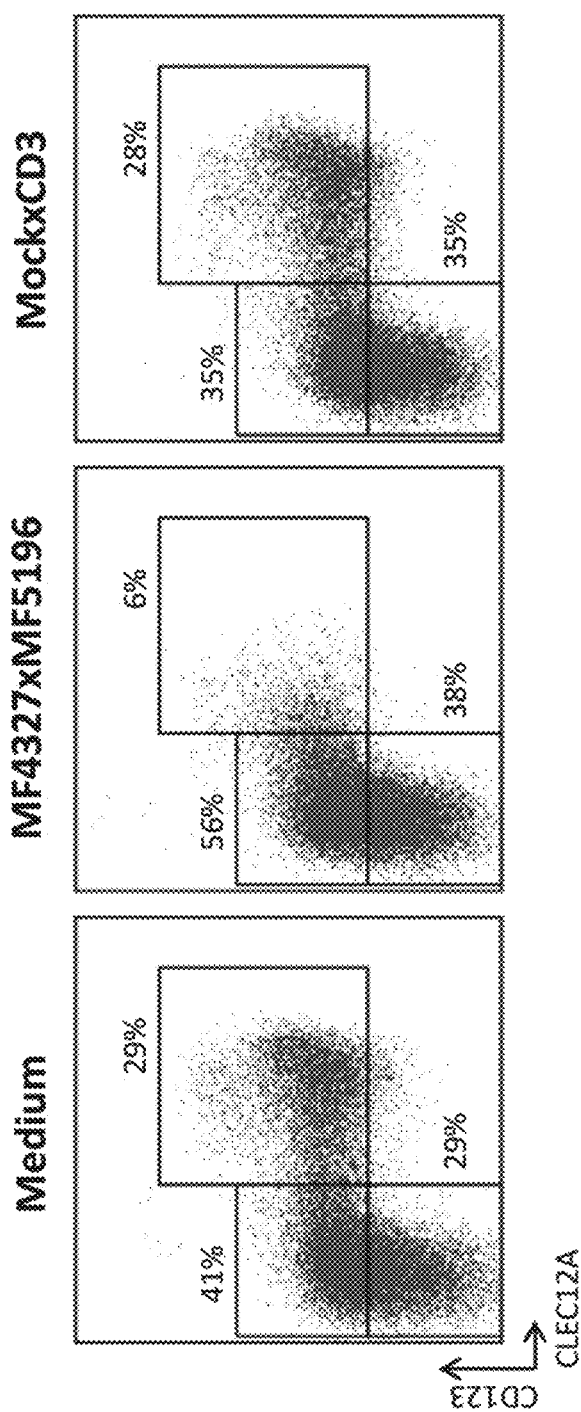

Antibody MF4327xMF5196-Induced Targeting of Normal CD34+ Cells Spares Erythrocyte and Megakaryocyte Differentiation as Well as Retains Potential to Develop the Mono-Myelocytic Lineage As CLEC12A is expressed in the mono-myelocytic progenitor compartment within the normal CD34$^{POS}$ compartment we aimed to evaluate the impact of antibody MF4327xMF5196 on normal haematopoiesis. To this end, cytotoxicity assays with healthy donor bone marrow-derived CD34$^{POS}$ cells and pre-activated autologous T cells were performed. Pre-activated T cells were used to have a short 16 hour cytotoxicity assay window which minimizes the impact of in vitro differentiation of the CD34$^{POS}$ cells on the outcome of the assay. We observed that antibody MF4327xMF5196 specifically lysed >86% of the CLEC12A$^{POS}$CD34$^{POS}$ cells, while leaving the CLEC12A$^{NEG}$ CD10$^{POS}$ or CD10$^{NEG}$ cell fractions unaffected (FIG. 4A). Detailed analysis of the various CD34$^{POS}$ progenitor fractions revealed that antibody MF4327xMF5196 targets CLEC12A-expressing GMPs (three-fold reduction, FIG. 4B). Antibody MF4327xMF5196 did neither significantly impact the cell fractions partially expressing CLEC12A (CMP and MEP) nor the CLEC12A-negative HSC, MPP and common lymphoid progenitors (CLP). Interestingly, antibody MF4327xMF5196 only lysed a fraction of CD123$^{POS}$ cells, showing that a large subset of CD123$^{POS}$CLEC12A$^{NEG}$ cells is not affected by antibody MF4327xMF5196, a subset that comprises CMPs (FIG. 4C).

Figure 4D:
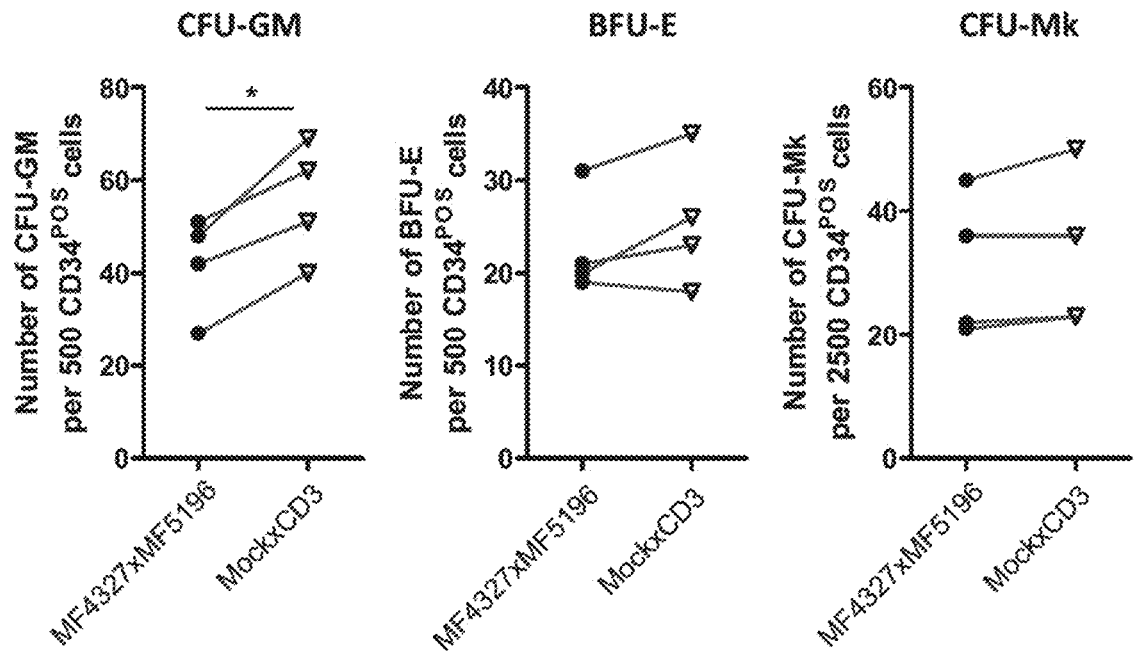
Figure 4E:
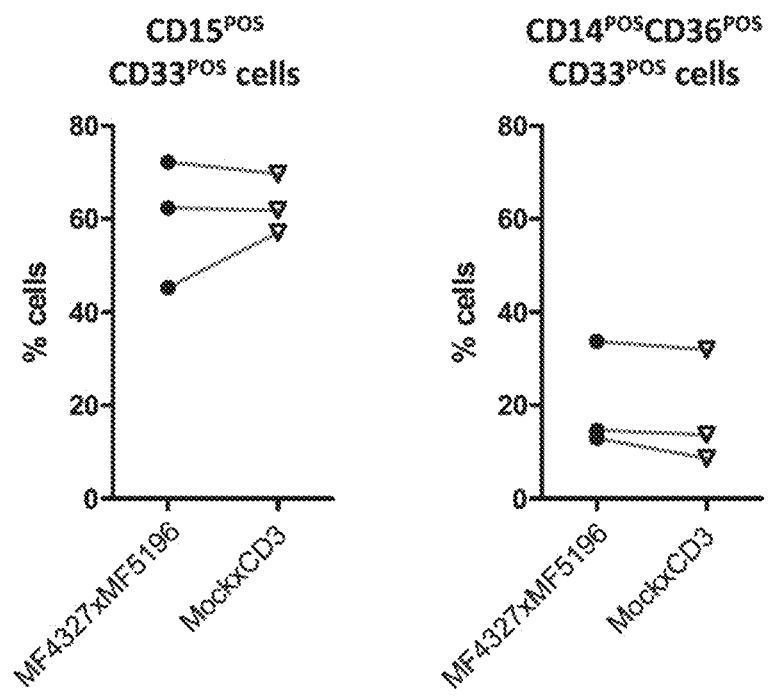

Next, the ability of the normal CD34$^{POS}$ cell fraction to give rise to monocytes, granulocytes, erythrocytes and megakaryocytes upon antibody MF4327xMF5196-induced redirected lysis was evaluated at a functional level using CFU assays. The outgrowth of the erythroid (BFU-E; burst-forming units-erythroid) or megakaryocyte (CFU-Mk; colony forming unit-megakaryocyte) colonies from the bone marrow CD34$^{POS}$ hemopoietic progenitor cells were not affected by antibody MF4327xMF5196 (FIG. 4D). Notably, despite that antibody MF4327xMF5196 induced redirected lysis caused a strong reduction in GMPs only a modest reduction of 24% in the outgrowth of granulocyte-macrophage colonies (CFU-GM) was observed at functional level. Interestingly, the GM-progenitor cells, unaffected by antibody MF4327xMF5196, retained their capacity to develop both CD14$^{POS}$CD36$^{POS}$CD33$^{POS}$ monocytic and CD15$^{POS}$CD33$^{POS}$ myelocytic cells (FIG. 4E), as determined by flow cytometric analysis of the CFU-GM colonies.

Taken together these data show that antibody MF4327xMF5196 does not affect erythroid megakaryocytic development. Furthermore, while it efficiently eradicates CLEC12A$^{POS}$CD34$^{POS}$ progenitors, granulocyte and monocyte development potential is retained upon antibody MF4327xMF5196 treatment.

Antibody MF4327xMF5196 Induces Redirected Lysis of Primary AML Blasts by Autologous T Cells Next, we determined the capacity of antibody MF4327xMF5196 to induce AML patient-derived T cells to lyse CLEC12A$^{POS}$ target cells. The T cell compartment from AML patients in morphologic clinical remission showed normal composition of naïve, central memory (CM), effector memory (EM) and effector memory cells with reacquired CD45RA (EMRA+) (FIG. 12A, B and Table III, patients 1-6). Analyzing the capacity of AML patient T cells to mediate antibody MF4327xMF5196 cytotoxicity of CLEC12A$^{POS}$ target cells revealed no differences between the ability of AML patient-derived T cells and that of healthy donor-derived T cells to induce antibody MF4327xMF5196-mediated T cell activation and lysis of CLEC12A$^{POS}$ cells (FIG. 12C-E).

Figure 5A:
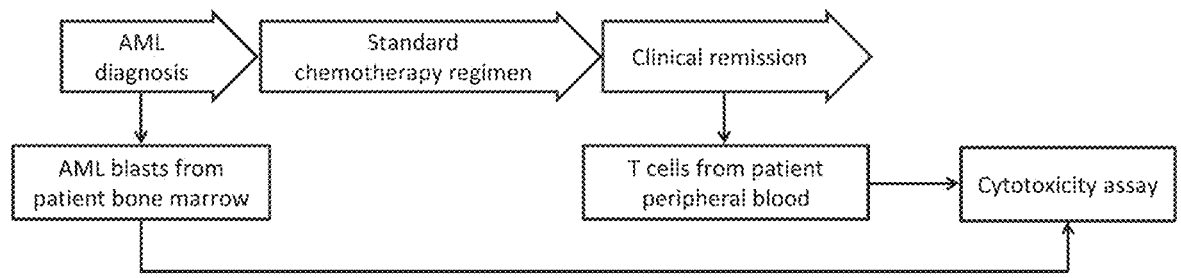
Figure 5B:
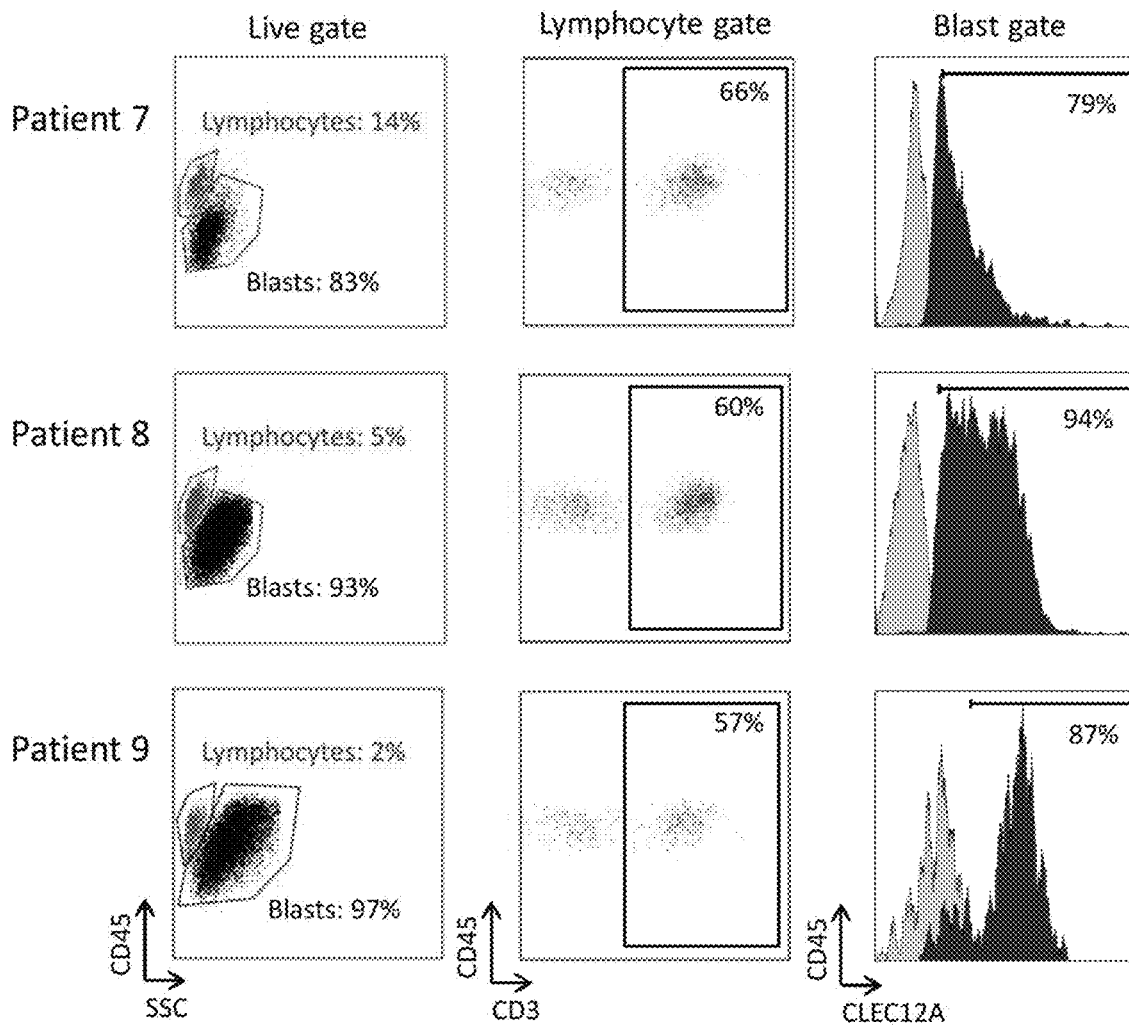
Figure 5C:
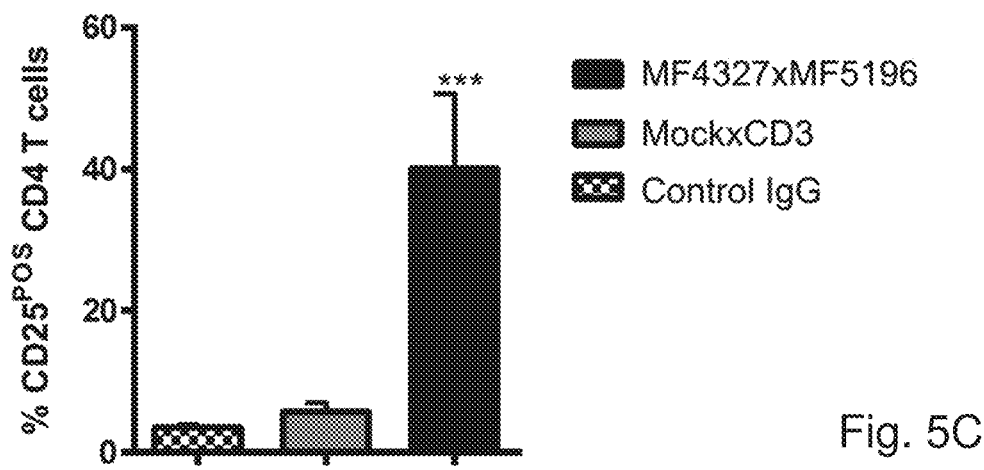
Figure 5D:
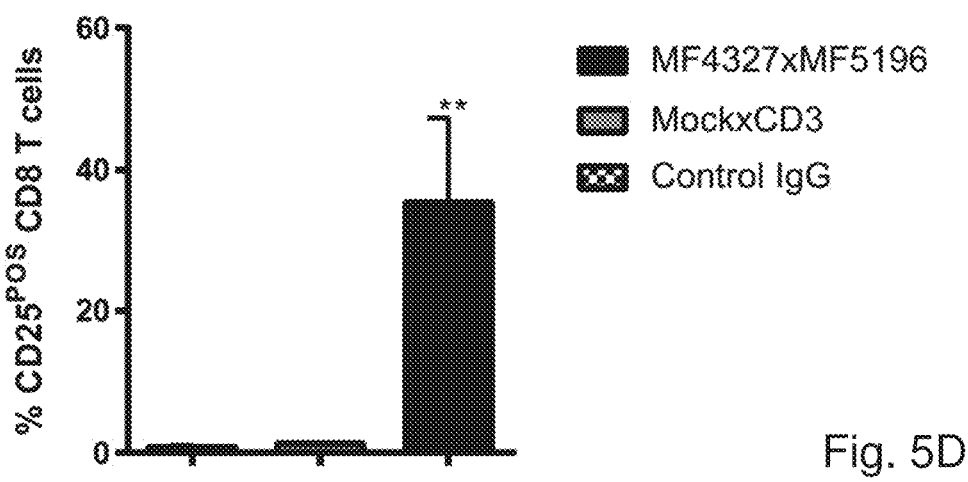
Figure 5E:
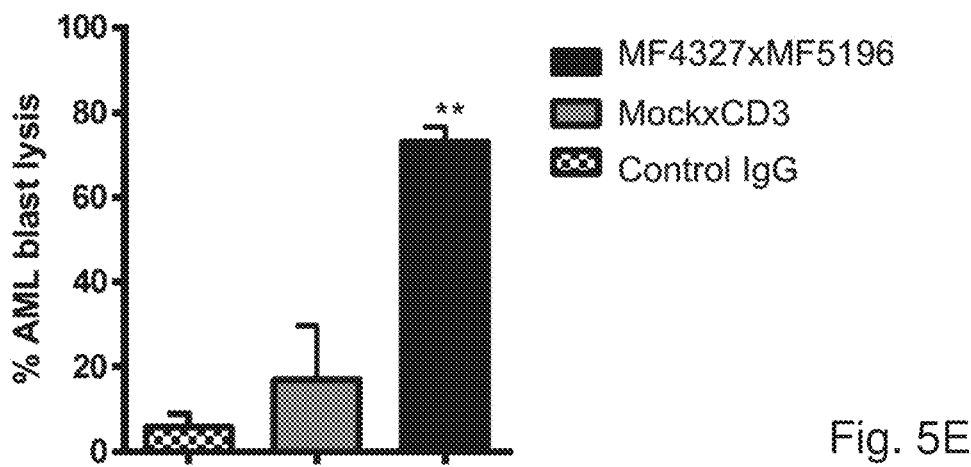

The capacity of antibody MF4327xMF5196 to induce CLEC12A-specific lysis of primary AML blasts by resting autologous T cells collected from the same AML patient at a later time point was determined (FIG. 5A, patients listed in Table III, patients 7-9). The primary AML blast samples taken at diagnosis contained a high fraction (>80%) of blasts expressing CLEC12A (FIG. 5B). The AML blasts were co-cultured with autologous resting T cells taken during clinical remission at an E:T ratio of 5:1 for 48 hours. Antibody MF4327xMF5196 induced potent CLEC12A-specific activation of CD4 and CD8 T cells as well as >70% AML blast lysis (FIG. 5C-E). These data reveal that antibody MF4327xMF5196 can efficiently induce lysis of CLEC12A$^{POS}$ primary AML blasts by autologous T cells.

Antibody MF4327xMF5196 Redirects Lysis of Primary AML Blasts in Diagnostic Samples with Low E:T Ratios We then determined the ability of antibody MF4327xMF5196 to induce lysis of AML blasts by autologous T cells in primary AML samples collected at diagnosis. In the primary AML samples tested (listed in Table III, patients 10-19), the numbers of T cells were relatively scarce compared with the numbers of AML blasts, resulting in low effective E:T ratios (1:3-1:97, Table II). FACS analysis revealed patient heterogeneity in terms of CLEC12A expression (Table II). The primary AML samples were cultured for 10 days in the presence of a cytokine cocktail to support AML blast and T cell survival during the assay. After 10 days of culture, the median AML blast recovery in the absence of antibody MF4327xMF5196 was 41-1591%. Antibody MF4327xMF5196 and MockxCD3 control IgG were added once at the onset of culture. T cell expansion and AML blast lysis was quantified by flow cytometry at day 7 and day 10. Not only did antibody MF4327xMF5196 efficiently induce CLEC12A-mediated T cell expansion (range of fold expansion 6-157), it also induced AML blast lysis at day 7 and day 10 (FIG. 6). At day 10, antibody MF4327xMF5196 had efficiently induced AML blast lysis (23-98%) in 10/11 patient samples. Although the MockxCD3 control antibody also reduced the numbers of tumor cells in some samples, in those samples the levels of T cell activation were much lower than those observed for antibody MF4327xMF5196 (median of 48 vs 2-fold T cell expansion by antibody MF4327xMF5196 vs MockxCD3). Notably, antibody MF4327xMF5196 was active even in AML samples with very low effector-to-target ratios (FIG. 6 and Table II). For the one AML sample in which no blast lysis was observed (patient 16), also the level of T cell expansion was only 15-fold compared to the median 48-fold T cell expansion as observed for the 10 antibody MF4327xMF5196 responsive samples.

In conclusion, antibody MF4327xMF5196 efficiently induced CLEC12A-mediated lysis of AML blasts by T cells present in AML patient bone marrow samples, even at very low E:T ratios, and also provoked robust T cell proliferation.

Antibody MF4327xMF5196 Dosing Regimen in Human AML Patients Leads to Mitigated Cytokine Levels Patient cytokine levels were measured upon treatment with antibody MF437xMF5196.

FIG. 14 shows the data obtained from patients that received a priming dose of 1 mg on day 1, followed by step-up doses of 3 mg on day 4 and 15 mg on day 8, and a full dose of 25 mg on day 15.

FIG. 15 shows the data obtained from patients that received a priming dose of 3 mg on day 1, followed by step-up doses of 10 mg on day 4 and 25 mg on day 8, and a full dose of 40 mg on day 15.

FIG. 16 shows the data obtained from patients that received a priming dose of 5 mg on day 1, followed by step-up doses of 15 mg on day 4 and 25 mg on day 8, and a full dose of 60 mg on day 15.

Overall, the data shows that, in select patients, the administration of a priming dose and step-dose doses mitigates cytokine release when the full dose is administered. For certain patients in various cohorts, limited cytokine release was observed throughout the priming, step-up and full dose (data not shown).

Discussion

Antibody MF4327xMF5196 as referred to in the examples is a full-length antibody. The Fc effector silenced version of the CLEC12AxCD3 bispecific human IgG1 antibody is shown to be able to treat all subtypes of AML by targeting CLEC12A on AML blasts and leukemic stem cells (LSCs). Antibody MF4327xMF5196 is a potent bispecific antibody that efficiently activates and redirects T cells to lyse CLEC12A-expressing cells such as AML cells. In 10/11 primary AML patient samples, this CLEC12AxCD3 T cell engager efficiently induced CLEC12A-mediated lysis of AML blasts by redirecting resident autologous T cells. In this ex vivo cytokine-supported system, AML samples were cultured for 7-10 days in the presence of antibody MF4327xMF5196. This assay establishes antibody MF4327xMF5196 efficacy in two ways: it revealed that antibody MF4327xMF5196 had the capacity to induce expansion of AML patient T cells in these samples, and it showed that those antibody MF4327xMF5196-redirected T cells were able to redirect cytolytic activity towards AML blasts through cytolysis (presented in Table II). Antibody MF4327xMF5196 was able to induce significant T cell expansion and blast lysis even in those AML samples that had low initial E:T ratios (1:45-1:97) or relatively low levels of CLEC12A expression. Comparison of the antibody MF4327xMF5196 versus MockxCD3 conditions in the ex vivo assay revealed that the antibody MF4327xMF5196-induced activity is CLEC12A antigen-mediated; robust T cell proliferation and AML blast cell lysis for antibody MF4327xMF5196 was observed compared to minimal activity for MockxCD3 in 9/10 primary AML samples. The one non-responding sample that lacked both AML blast lysis and robust antibody MF4327xMF5196-induced T cell expansion (patient 16), likely had severe T cell dysfunction.

Although healthy donor T cells were used in many initial experiments, cytotoxicity assays were also performed using AML patient-derived T cells to test the capability of antibody MF4327xMF5196 to redirect T cells in a disease setting. Specific defects have been reported for AML T cells, including impaired immunological synapse formation and reduced T cell costimulatory capacity (Wendelbo, Nesthus et al. 2004, Le Dieu, Taussig et al. 2009). Here, it is shown that antibody MF4327xMF5196 can redirect AML patient-derived T cells obtained at morphologic clinical remission (n=6) as efficiently as it redirects healthy donor-derived T cells to induce CLEC12A-specific lysis of CLEC12A$^{POS}$ tumor cells. Moreover, in 10/11 AML samples it was found that antibody MF4327xMF5196 could effectively redirect the autologous T cells in primary de novo AML samples to lyse AML blasts. Here, it is demonstrated that AML patient-derived T cells can be functionally activated by a full-length IgG CD3-engaging bispecific IgG, resulting in T cell activation and proliferation, in a HSC-sparing manner and at low E:T ratios. Such functional activation of autologous T cells via antibody MF4327xMF5196 effectively enlarges the effector T cell compartment, thus facilitating more favorable E:T ratios for efficient eradication of AML blasts and LSCs in patients.

In normal bone marrow, antibody MF4327xMF5196 binding is restricted to the myeloid compartment, as antibody MF4327xMF5196 is capable of a CLEC12A-specific targeting, sparing other regions of the bone marrow. Here, it is shown that antibody MF4327xMF5196 binds in the bone marrow uniformly to GMP cells, while it only binds a minor fraction of the CMP and MEP subsets. More importantly, antibody MF4327xMF5196 does not bind to the CD34$^{POS}$CD38$^{NEG}$ compartment which includes pluripotent HSCs. In line with the minor CLEC12A expression on the CMP and MEP fractions it is shown that antibody MF4327xMF5196 does not affect the development of erythroid nor megakaryocytic lineage in our in vitro CFU assays. Furthermore, although antibody MF4327xMF5196 reduced the number of CLEC12A$^{POS}$ GMP cells in the ex vivo cytotoxicity assay, it is observed in the follow-up CFU assays that upon antibody MF4327xMF5196 treatment the remaining CD34$^{POS}$ bone marrow cells were able to give rise to both the monocytic and myelocytic lineages, permitting mono-myelocytic outgrowth arising from CD34$^{POS}$CLEC12A$^{NEG}$ progenitor cells, including HSCs and MPPs, which are not observably impacted by the treatment of antibody MF4327xMF5196 (van Rhenen, van Dongen et al. 2007, Notta, Zandi et al. 2016, Bill, van Kooten Niekerk et al. 2018).

It is anticipated that hematological toxicity following administration of antibody MF4327xMF5196 to patients might be limited to neutropenia and reduction of monocyte counts. The present results demonstrate that upon antibody MF4327xMF5196 re-directed lysis neutrophils and monocytes can re-populate the host from the remaining CD34$^{POS}$ cells. The potential for repopulation of hemopoietic cells after treatment with antibody MF4327xMF5196 contrasts with the likely situation for treatments that target CD33 or CD123 (Aigner, Feulner et al. 2013, Al-Hussaini, Rettig et al. 2016). Compared with CLEC12A, CD33 and CD123 are more widely expressed on normal CD34$^{POS}$ progenitors, including CMPs, GMPs and pluripotent HSCs (Taussig, Pearce et al. 2005).

The present invention shows that CLEC12A targeting spares the normal CD123$^{POS}$ CMPs which are a target for CD123 directing therapies. In vivo studies in humanized mice have shown that CD33 and CD123 targeting chimeric antigen receptor (CAR)-transduced T cells induce lysis in the CD34$^{POS}$CD38$^{NEG}$ stem cell fraction (Pizzitola, Anjos-Afonso et al. 2014, Kenderian, Ruella et al. 2015). As a consequence, haematological toxicity concerns have been raised for therapies targeting CD33 and CD123: there is the possibility that these therapies could induce thrombocytopaenia, neutropaenia and anaemia, in addition to the risk of HSC eradication which would prohibit efficient re-establishment of the normal hemopoietic compartment.

The Fc region of antibody MF4327xMF5196 has been modified to prevent binding to FcγR and C1q, without affecting binding to the FcRn receptor. The results of the monocyte assays indeed showed that antibody MF4327xMF5196-induced T cell activation and associated cytokine release is restricted to CLEC12A expressing cells. The Fc silencing dampens typical antibody dependent cellular cytotoxicity (ADCC) and C1q-mediated complement-dependent cytotoxicity (CDC) of CD3$^{POS}$ and/or CLEC12A$^{POS}$ cells. The present data shows that antibody MF4327xMF5196-activated T cells lyse CLEC12A$^{POS}$ cells selectively (e.g. B cells and NK cells were unaffected in PBMC cultures).

The study in mice confirmed that antibody MF4327xMF5196, a full-length IgG1, has a normal FcRn-mediated in vivo half-life of 9-10 days. This means that—unlike other T cell engager concepts—effective systemic levels of antibody MF4327xMF5196 in patients can be achieved by weekly intravenous administration.

Antibody MF4327xMF5196 selectively targets myeloid blasts while sparing normal HSCs. Based on its potential to eradicate residual LSCs, antibody MF4327xMF5196 is considered for the management of minimal residual disease (MRD) in AML.

Example 2

Studies of CLEC12A negative and CLEC12A positive CD34+ stem and progenitor cells from patients with Myeloproliferative Neoplasm blast phase (MPN-BP).

Cells were collected from the bone marrow of MPN-BP patients. CD34+ cells were sorted at the basis of forward scatter (FSC), side scatter (SSC), CD45, CD34, CD38 and CLEC12A expression. Cells with low SSC and that were CD45$^{dim}$, CD34$^+$, CD38$^-$ were sorted into two fractions on the basis of CLEC12A expression. The cells were plated in MethoCult™ H4435 Enriched (STEMCELL technologies) supplemented with SCF, IL-3, IL-6, EPO, G-CSF, and GM-CSF and incubated for 12-14 days. Colonies were picked and re-plated in MethoCult™ H4435 Enriched (STEMCELL technologies) supplemented with SCF, IL-3, IL-6, EPO, G-CSF, and GM-CSF and re-incubated for 12-14 days. The results of the first plating were that the CLEC12A negative fraction had 20 big colonies of (40 cells or more) and 10 small colonies (<40 cells per colony) per 1500 plated cells. The CLEC12A positive fraction had no big and 32 small colonies per 1500 plated cells. The colonies in the plates of the CLEC12A negative fraction were not able to generate secondary colonies in the re-plating experiment, zero big or small colonies per 1500 seeded cells. On the other hand re-plating the cells from the CLEC12A first plating resulted in 44 small colonies per 1500 cells, of these approximately 80% was positive for the JAK2 driver mutation, see FIG. 13.

SUMMARY

CD34posCD38-CLEC12A- cells from MPN-BP patient are only able to generate hemopoietic colonies (CFU-GM) in primary culture, which are predominately CFU-GM. By contrast, CD34-CD38- stem cells in MPN-PB patients expressing CLEC12A are capable of generating blast colonies that can be serially re-plated and therefore contain leukemic initiating capacity.

Differential CLEC12A expression can be used to identify, eradicate and/or isolate leukemic initiating cells (LIC) from patients with MPN-BP. A CD3-CLEC12A bispecific antibody as disclosed herein can be used to eradicate these LIC in MPN-PB, to reduce the number of MPN blast phase cells and thereby alleviate the disease in patients with MPN-BP.

CITED ART

Aigner, M., J. Feulner, S. Schaffer, R. Kischel, P. Kufer, K. Schneider, A. Henn, B. Rattel, M. Friedrich, P. A. Baeuerle, A. Mackensen and S. W. Krause (2013). "T lymphocytes can be effectively recruited for ex vivo and in vivo lysis of AML blasts by a novel CD33/CD3-bispecific BiTE antibody construct." Leukemia 27(5): 1107-1115.

Al-Hussaini, M., M. P. Rettig, J. K. Ritchey, D. Karpova, G. L. Uy, L. G. Eissenberg, F. Gao, W. C. Eades, E. Bonvini, G. R. Chichili, P. A. Moore, S. Johnson, L. Collins and J. F. DiPersio (2016). "Targeting CD123 in acute myeloid leukemia using a T-cell-directed dual-affinity retargeting platform." Blood 127(1): 122-131.

Arrighi, J. F., C. Soulas, C. Hauser, S. Saeland, B. Chapuis, R. H. Zubler and V. Kindler (2003). "TNF-alpha induces the generation of Langerin/(CD207)+ immature Langerhans-type dendritic cells from both CD14-CD1a and CD14+CD1a- precursors derived from CD34+ cord blood cells." Eur J Immunol 33(7): 2053-2063.

Baeuerle, P. A. and C. Reinhardt (2009). "Bispecific T-cell engaging antibodies for cancer therapy." Cancer Res 69(12): 4941-4944.

Bakker, A. B., S. van den Oudenrijn, A. Q. Bakker, N. Feller, M. van Meijer, J. A. Bia, M. A. Jongeneelen, T. J. Visser, N. Bijl, C. A. Geuijen, W. E. Marissen, K. Radosevic, M. Throsby, G. J. Schuurhuis, G. J. Ossenkoppele, J. de Kruif, J. Goudsmit and A. M. Kruisbeek (2004). "C-type lectin-like molecule-1: a novel myeloid cell surface marker associated with acute myeloid leukemia." Cancer Res 64(22): 8443-8450.

Bill, M., B van Kooten Niekerk, P., S Woll, P., Laine Herborg, L., Stidsholt Roug, A., Hokland, P., & Nederby, L. (2018). Mapping the CLEC12A expression on myeloid progenitors in normal bone marrow; implications for understanding CLEC12A-related cancer stem cell biology. Journal of cellular and molecular medicine, 22(4), 2311-2318.

Johnson, A. (2018, October 9). Affimed sinks after placing clinical hold on bispecific T cell engager. *Biocentury Clinical News*. Retrieved from URL.

Brinkmann, U. and R. E. Kontermann (2017). "The making of bispecific antibodies." MAbs 9(2): 182-212.

Burnett, A., M. Wetzler and B. Lowenberg (2011). "Therapeutic advances in acute myeloid leukemia." J Clin Oncol 29(5): 487-494.

Chen, C. H., Floyd, H., Olson, N. E., Magaletti, D., Li, C., Draves, K., & Clark, E. A. (2006). Dendritic-cell-associated C-type lectin 2 (DCAL-2) alters dendritic-cell maturation and cytokine production. Blood, 107(4), 1459-1467.

de Kruif, J., A. Kramer, T. Visser, C. Clements, R. Nijhuis, F. Cox, V. van der Zande, R. Smit, D. Pinto, M. Throsby and T. Logtenberg (2009). "Human immunoglobulin repertoires against tetanus toxoid contain a large and diverse fraction of high-affinity promiscuous V(H) genes." J Mol Biol 387(3): 548-558.

de Kruif, J., Kramer, A., Nijhuis, R., van der Zande, V., den Blanken, R., Clements, C., . . . Logtenberg, T. (2010). Generation of stable cell clones expressing mixtures of human antibodies. Biotechnology and bioengineering, 106(5), 741-750.

De Nardis, C., L. J. A. Hendriks, E. Poirier, T. Arvinte, P. Gros, A. B. H. Bakker and J. de Kruif (2017). "A new approach for generating bispecific antibodies based on a common light chain format and the stable architecture of human immunoglobulin G1." J Biol Chem 292(35): 14706-14717.

Gunasekaran, K., M. Pentony, M. Shen, L. Garrett, C. Forte, A. Woodward, S. B. Ng, T. Born, M. Retter, K. Manchulenko, H. Sweet, I. N. Foltz, M. Wittekind and W. Yan (2010). "Enhancing antibody Fc heterodimer formation through electrostatic steering effects: applications to bispecific molecules and monovalent IgG." J Biol Chem 285(25): 19637-19646.

Han, Y., Zhang, M., Li, N., Chen, T., Zhang, Y., Wan, T., & Cao, X. (2004). KLRL1, a novel killer cell lectinlike receptor, inhibits natural killer cell cytotoxicity. Blood, 104(9), 2858-2866.

Juliusson, G., V. Lazarevic, A. S. Horstedt, O. Hagberg, M. Hoglund and G. Swedish Acute Leukemia Registry (2012). "Acute myeloid leukemia in the real world: why population-based registries are needed." Blood 119(17): 3890-3899.

Kenderian, S. S., M. Ruella, O. Shestova, M. Klichinsky, V. Aikawa, J. J. Morrissette, J. Scholler, D. Song, D. L. Porter, M. Carroll, C. H. June and S. Gill (2015). "CD33-specific chimeric antigen receptor T cells exhibit potent preclinical activity against human acute myeloid leukemia." Leukemia 29(8): 1637-1647.

Kikushige, Y. and T. Miyamoto (2013). "TIM-3 as a novel therapeutic target for eradicating acute myelogenous leukemia stem cells." Int J Hematol 98(6): 627-633.

Kontermann R E, Brinkmann U. Corrigendum to "Bispecific antibodies" [Drug Discov. Today 20 (July (7)) (2015) 838-847]. Drug Discov Today. 2019; 24(7):1422.

Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley Lahoud M H, Proietto A I, Ahmet F, et al. The C-type lectin Clec12A present on mouse and human dendritic cells can serve as a target for antigen delivery and enhancement of antibody responses. J Immunol. 2009; 182(12):7587-7594.

Larsen H Ø, Roug A S, Just T, Brown G D, Hokland P. Expression of the hMICL in acute myeloid leukemia-a highly reliable disease marker at diagnosis and during follow-up. Cytometry B Clin Cytom. 2012; 82(1):3-8.

Le Dieu R, Taussig D C, Ramsay A G, et al. Peripheral blood T cells in acute myeloid leukemia (AML) patients at diagnosis have abnormal phenotype and genotype and form defective immune synapses with AML blasts. Blood. 2009; 114(18):3909-3916.

Löwenberg B, Ossenkoppele G J, van Putten W, et al. High-dose daunorubicin in older patients with acute myeloid leukemia [published correction appears in N Engl J Med. 2010 Mar. 25; 362(12):1155. N Engl J Med. 2009; 361(13):1235-1248.

Marshall, A. S., Willment, J. A., Lin, H. H., Williams, D. L., Gordon, S., & Brown, G. D. (2004). Identification and characterization of a novel human myeloid inhibitory C-type lectin-like receptor (MICL) that is predominantly expressed on granulocytes and monocytes. The Journal of biological chemistry, 279(15), 14792-14802.

Morris G E. Overview. Choosing a method for epitope mapping. Methods Mol Biol. 1996; 66:1-9.

Moshaver B, van Rhenen A, Kelder A, et al. Identification of a small subpopulation of candidate leukemia-initiating cells in the side population of patients with acute myeloid leukemia. Stem Cells. 2008; 26(12):3059-3067.

Needleman S B, Wunsch C D. A general method applicable to the search for similarities in the amino acid sequence of two proteins. J Mol Biol. 1970; 48(3):443-453.

Notta, F., S. Zandi, N. Takayama, S. Dobson, O. I. Gan, G. Wilson, K. B. Kaufmann, J. McLeod, E. Laurenti, C. F. Dunant, J. D. McPherson, L. D. Stein, Y. Dror and J. E. Dick (2016). "Distinct routes of lineage development reshape the human blood hierarchy across ontogeny." Science 351(6269): aab2116.

Oganesyan V, Gao C, Shirinian L, Wu H, Dall'Acqua W F. Structural characterization of a human Fc fragment engineered for lack of effector functions. Acta Crystallogr D Biol Crystallogr. 2008; 64(Pt 6):700-704.

Oran, B. and D. J. Weisdorf (2012). "Survival for older patients with acute myeloid leukemia: a population-based study." Haematologica 97(12): 1916-1924.

Toft-Petersen M, Nederby L, Kjeldsen E, et al. Unravelling the relevance of CLEC12A as a cancer stem cell marker in myelodysplastic syndrome. Br J Haematol. 2016; 175 (3):393-401.

Pizzitola, I., F. Anjos-Afonso, K. Rouault-Pierre, F. Lassailly, S. Tettamanti, O. Spinelli, A. Biondi, E. Biagi and D. Bonnet (2014). "Chimeric antigen receptors against CD33/CD123 antigens efficiently target primary acute myeloid leukemia cells in vivo." Leukemia 28(8): 1596-1605.

Rice P, Longden I, Bleasby A. EMBOSS: the European Molecular Biology Open Software Suite. Trends Genet. 2000; 16(6):276-277.

Schaefer G, Haber L, Crocker L M, et al. A two-in-one antibody against HER3 and EGFR has superior inhibitory activity compared with monospecific antibodies. Cancer Cell. 2011; 20(4):472-486.

Sheridan C. Despite slow progress, bispecifics generate buzz. Nat Biotechnol. 2016; 34(12):1215-1217.

Spiess C, Zhai Q, Carter P J. Alternative molecular formats and therapeutic applications for bispecific antibodies. Mol Immunol. 2015; 67(2 Pt A):95-106.

Taussig D C, Pearce D J, Simpson C, et al. Hematopoietic stem cells express multiple myeloid markers: implications for the origin and targeted therapy of acute myeloid leukemia. Blood. 2005; 106(13):4086-4092.

Le Tourneau C, Michiels S, Gan H K, Siu L L. Reporting of time-to-event end points and tracking of failures in randomized trials of radiotherapy with or without any concomitant anticancer agent for locally advanced head and neck cancer. J Clin Oncol. 2009; 27(35):5965-5971.

van Rhenen A, van Dongen G A, Kelder A, et al. The novel AML stem cell associated antigen CLL-1 aids in discrimination between normal and leukemic stem cells. Blood. 2007; 110(7):2659-2666.

Wendelbo Ø, Nesthus I, Sjo M, Paulsen K, Ernst P, Bruserud Ø. Functional characterization of T lymphocytes derived from patients with acute myelogenous leukemia and chemotherapy-induced leukopenia. Cancer Immunol Immunother. 2004; 53(8):740-747.

Zhang, X., Y. Yang, D. Fan and D. Xiong (2017). "The development of bispecific antibodies and their applications in tumor immune escape." Exp Hematol Oncol 6: 12.

Zhao, X., S. Singh, C. Pardoux, J. Zhao, E. D. Hsi, A. Abo and W. Korver (2010). "Targeting C-type lectin-like molecule-1 for antibody-mediated immunotherapy in acute myeloid leukemia." Haematologica 95(1): 71-78.

SEQUENCE LISTING SUMMARY

| | | |
|---|---|---|
| 1 | Human CLEC12A | MWIDFFTYSSMSEEVTYADLQFQNSSEMEKIPEIGKFGEKAPPAPSHVWRPAALF LTLLCLLLLIGLGVLASMFHVTLKIEMKKMNKLQNISEELQRNISLQLMSNMNIS NKIRNLSTTLQTIATKLCRELYSKEQEHKCKPCPRRWIWHKDSCYFLSDDVQTWQ ESKMACAAQNASLLKINNKNALEFIKSQSRSYDYWLGLSPEEDSTRGMRVDNIIN SSAWVIRNAPDLNNMYCGYINRLYVQYYHCTYKKRMICEKMANPVQLGSTYFREA |
| 2 | Human CD3γ | MEQGKGLAVL ILAIILLQGT LAQSIKGNHL VKVYDYQEDG SVLLTCDAEA KNITWFKDGK MIGFLTEDKK KWNLGSNAKD PRGMYQCKGS QNKSKPLQVY YRMCQNCIEL NAATISGFLF AEIVSIFVLA VGVYFIAGQD GVRQSRASDK QTLLPNDQLY QPLKDREDDQ YSHLQGNQLR RN |
| 3 | Human CD3δ | MEHSTFLSGL VLATLLSQVS PFKIPIEELE DRVFVNCNTS ITWVEGTVGT LLSDITRLDL GKRILDPRGI YRCNGTDIYK DKESTVQVHY RMCQSCVELD PATVAGIIVT DVIATLLLAL GVFCFAGHET GRLSGAADTQ ALLRNDQVYQ PLRDRDDAQY SHLGGNWARN K |
| 4 | Human CD3ε | MQSGTHWRVL GLCLLSVGVW GQDGNEEMGG ITQTPYKVSI SGTTVILTCP QYPGSEILWQ HNDKNIGGDE DDKNIGSDED HLSLKEFSEL EQSGYYVCYP RGSKPEDANF YLYLRARVCE NCMEMDVMSV ATIVIVDICI TGGLLLLVYY WSKNRKAKAK PVTRGAGAGG RQRGQNKERP PPVPNPDYEP IRKGQRDLYS GLNQRRI |
| 5 | Human CD3ζ | MKWKALFTAA ILQAQLPITE AQSFGLLDPK LCYLLDGILF IYGVILTALF LRVKFSRSAD APAYQQGQNQ LYNELNLGRR EEYDVLDKRR GRDPEMGGKP QRRKNPQEGL YNELQKDKMA EAYSEIGMKG ERRRGKGHDG LYQGLSTATK DTYDALHMQA LPPR |
| 6 | Human IL-15 Signal peptide underlined | MRISKPHLRSISIQCYLCLLLNSHFLTEAGIHVFILGCFSAGLPKTEANWVNVIS DLKKIEDLIQSMHIDATLYTESDVHPSCKVTAMKCFLLELQVISLESGDASIHDT VENLIILANNSLSSNGNVTESGCKECEELEEKNIKEFLQSFVHIVQMFINTS |
| 7 | Human IL-15Ra Signal peptide underlined | MAPRRARGCR TLGLPALLLL LLLRPPATRG ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQG HSDTTVAIST STVLLCGLSA VSLLACYLKS RQTPPLASVE MEAMEALPVT WGTSSRDEDL ENCSHHL |
| 8 | Soluble human IL-15Ra Signal peptide underlined | MAPRRARGCR TLGLPALLLL LLLRPPATRG ITCPPPMSVE HADIWVKSYS LYSRERYICN SGFKRKAGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEISSHES SHGTPSQTTA KNWELTASAS HQPPGVYPQG |
| 9 | CLEC12A 4327 HCDR1 | SGYTFTGY |
| 10 | CLEC12A 4327 HCDR2 | IINPSGGS |
| 11 | CLEC12A 4327 HCDR3 | GTTGDWFDY |
| 12 | 4327 VH | QVQLVQSGAEVKKPGASVKVSCKASGYTFTSYYMHWVRQAPGQGLEWMGIINPSG GSTSYAQKFQGRVTMTRDTSTSTVYMELSSLRSEDTAVYYCAKGTTGDWFDYWGQ GTLVTVSS |
| 13 | CLEC12A 4331 HCDR1 | SGYTFTSY |
| 14 | CLEC12A 4331 HCDR2 | IINPSGGS |
| 15 | CLEC12A 4331 HCDR3 | GNYGDEFDY |

| | | |
|---|---|---|
| 16 | 4331 VH | EVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGNYGDEFDYWGQGTLVTVSS |
| 17 | CLEC12A HCDR1 | SGYTFTGY |
| 18 | CLEC12A HCDR2 | WINPNSGG |
| 19 | CLEC12A HCDR3 | DGYFADAFDY |
| 20 | CLEC12A VH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARDGYFADAFDYWGQGTLVTVSS |
| 21 | 3056 HCDR1 | GFTFSSYG |
| 22 | 3056 HCDR2 | IWYNGRKQ |
| 23 | 3056 HCDR3 | GTGYNWFDP |
| 24 | MF3056 VH | QVQLVQSGGGVVQPGRSLRLSCVASGFTFSSYGMHWVRQAPGKGLEWVAAIWYNGRKQDYADSVKGRFTISRDNSKNTLYLQMNSLRAEDTAVYYCTRGTGYNWFDPWGQGTLVTVSS |
| 25 | MF3874 | QVQLVESGGGVVQPGRSLRLSCVASGFTFSSYGMHWVRQAPGKGLEWVAAIWYNGRKQDYADSVKGRFTISRDNSKNTLYLQMNSLRAEDTAVYYCTRGTGYNWFDPWGQGTLVTVSS |
| 26 | MF3878 | QVQLVQSGGGVVQPGRSLRLSCAASGFTFSSYGMHWVRQAPGKGLEWVAAIWYNGRKQDYADSVKGRFTISRDNSKNTLYLQMNSLRAEDTAVYYCTRGTGYNWFDPWGQGTLVTVSS |
| 27 | MF3883 | QVQLVQSGGGVVQPGRSLRLSCVASGFTFSSYGMHWVRQAPGKGLEWVAVIWYNGRKQDYADSVKGRFTISRDNSKNTLYLQMNSLRAEDTAVYYCTRGTGYNWFDPWGQGTLVTVSS |
| 28 | MF3886 | QVQLVQSGGGVVQPGRSLRLSCVASGFTFSSYGMHWVRQAPGKGLEWVAAIWYNGRKQDYADSVKGRFTISRDNSKNTLYLQMNSLRAEDTAVYYCARGTGYNWFDPWGQGTLVTVSS |
| 29 | MF3891 | QVQLVESGGGVVQPGRSLRLSCAASGFTFSSYGMHWVRQAPGKGLEWVAAIWYNGRKQDYADSVKGRFTISRDNSKNTLYLQMNSLRAEDTAVYYCARGTGYNWFDPWGQGTLVTVSS |
| 30 | 3896 HCDR2 | IWYSGSKKN |
| 31 | 3896 VH | QVQLVESGGGVVQPGRSLRLSCAASGFTFRSYGMHWVRQAPGKGLEWVAAIWYSGSKKNYADSVKGRFTISRDNSKNTLYLQMNSLRAEDTAVYYCARGTGYNWFDPWGQGTLVTVSS |
| 32 | MF5192 HCDR2 | IWYHGRKQ |
| 33 | MF5192 | QVQLVQSGGGVVQPGRSLRLSCVASGFTFSSYGMHWVRQAPGKGLEWVAAIWYHGRKQDYADSVKGRFTISRDNSKNTLYLQMNSLRAEDTAVYYCTRGTGYNWFDPWGQGTLVTVSS |
| 34 | MF5193 HCDR2 | IWYHARKQ |
| 35 | MF5193 | QVQLVQSGGGVVQPGRSLRLSCVASGFTFSSYGMHWVRQAPGKGLEWVAAIWYHARKQDYADSVKGRFTISRDNSKNTLYLQMNSLRAEDTAVYYCTRGTGYNWFDPWGQGTLVTVSS |
| 36 | MF5196 HCDR2 | IWYNARKQ |
| 37 | MF5196 | QVQLVQSGGGVVQPGRSLRLSCVASGFTFSSYGMHWVRQAPGKGLEWVAAIWYNARKQDYADSVKGRFTISRDNSKNTLYLQMNSLRAEDTAVYYCTRGTGYNWFDPWGQGTLVTVSS |
| 38 | MF5603 | QVQLVQSGGGVVQPGRSLRLSCVASGFTFSSYGMHWVRQAPGKGLEWVAAIWYNARKQEYIDSVKGRFTISRDNSKNTLYLQMNSLRAEDTAVYYCTRGTGYNWFDPWGQGTLVTVSS |
| 39 | MF5616 | QVQLVQSGGGVVQPGRSLRLSCVASGFTFSSYGMHWVRQAPGKGLEWVAAIWYNARKQEYNDSVKGRFTISRDNSKNTLYLQMNSLRAEDTAVYYCTRGTGYNWFDPWGQGTLVTVSS |

| | | |
|---|---|---|
| 40 | MF5626 | QVQLVQSGGGVVQPGRSLRLSCVASGFTFSSYGMHWVRQAPGKGLEWVAAIWYNA RKQEYRDSVKGRFTISRDNSKNTLYLQMNSLRAEDTAVYYCTRGTGYNWFDPWGQ GTLVTVSS |
| 41 | MF5630 | QVQLVQSGGGVVQPGRSLRLSCVASGFTFSSYGMHWVRQAPGKGLEWVAAIWYNA RKQDYADSVKGRFTISRDNSKNTLYLQMNSLRAEDTAVYYCTRGTGYNWYDPWGQ GTLVTVSS |
| 42 | MF5648 | QVQLVQSGGGVVQPGRSLRLSCVASGFTFSSYGMHWVRQAPGKGLEWVAAIWYNA RKQEYLDSVKGRFTISRDNSKNTLYLQMNSLRAEDTAVYYCTRGTGYNWFDPWGQ GTLVTVSS |
| 43 | MF5661 | QVQLVQSGGGVVQPGRSLRLSCVASGFTFSSYGMHWVRQAPGKGLEWVAQIWYNA RKQEYSDSVKGRFTISRDNSKNTLYLQMNSLRAEDTAVYYCTRGTGYNWFDPWGQ GTLVTVSS |
| 44 | MF5694 | QVQLVQSGGGVVQPGRSLRLSCVASGFTFSSYGMHWVRQAPGKGLEWVAAIWYNA RKQEYSDSVKGRFTISRDNSKNTLYLQMNSLRAEDTAVYYCTRGTGYNWFDPWGQ GTLVTVSS |
| 45 | MF5197 HCDR2 | IWYNTRKQ |
| 46 | MF5197 | QVQLVQSGGGVVQPGRSLRLSCVASGFTFSSYGMHWVRQAPGKGLEWVAAIWYNT RKQDYADSVKGRFTISRDNSKNTLYLQMNSLRAEDTAVYYCTRGTGYNWFDPWGQ GTLVTVSS |
| 47 | MF5351 HCDR2 | IWYDGKNT |
| 48 | MF5351 | QVQLVQSGGGVVQPGRSLRLSCAASGFTFSSYGMHWVRQAPGKGLEWVAMIWYDG KNTYYADSVKGRFTISRDNSKNTLYLQMNSLRAEDTAVYYCTRGTGYNWFDPWGQ GTLVTVSS |
| 49 | MF5354 HCDR2 | IYYDGSRT |
| 50 | MF5354 | QVQLVQSGGGVVQPGRSLRLSCAASGFTFSGYGMHWVRQAPGKGLEWVAQIYYDG SRTYYADSVKGRFTISRDNSKNTLYLQMNSLRAEDTAVYYCTRGTGYNWFDPWGQ GTLVTVSS |
| 51 | MF5356 HCDR2 | IWHDGRKT |
| 52 | MF5356 | QVQLVESGGGVVQPGRSLRLSCAASGFTFSKYGMHWVRQAPGKGLEWVAQIWHDG RKTYYADSVKGRFTISRDNSKNTLYLQMNSLRAEDTAVYYCTRGTGYNWFDPWGQ GTLVTVSS |
| 53 | VL CDR1 | QSISSY |
| 54 | VL CDR2 | AASSLQS |
| 55 | VL CDR3 | QQSYSTP |
| 56 | IgVk1-39*01 | DIQMTQSPSSLSASVGDRVTITCRASQSISSYLNWYQQKPGKAPKLLIYAASSLQ SGVPSRFSGSGSGTDFTLTISSLQPEDFATYYCQQSYSTP |
| 57 | Common Light Chain IgKV1*39/jk1 | DIQMTQSPSSLSASVGDRVTITCRASQSISSYLNWYQQKPGKAPKLLIYAASSLQ SGVPSRFSGSGSGTDFTLTISSLQPEDFATYYCQQ SYSTPPTFGQGTKVEIK |
| 58 | Common Light Chain IgKV1*39/jk5 | DIQMTQSPSSLSASVGDRVTITCRASQSISSYLNWYQQKPGKAPK LLIYAASSLQSGVPSRFSGSGSGTDFTLTISSLQPEDFATYYCQQ SYSTPPITFGQGTRLEIK |
| 59 | MF1337 TT VH | EVQLVETGAEVKKPGASVKVSCKASDYIFTKYDINWVRQAPGQGLEWMGWMSANT GNTGYAQKFQGRVTMTRDTSINTAYMELSSLTSGDTAVYFCARSSLFKTETAPYY HFALDVWGQGTTVTVSS |
| 60 | 3056 HCDR1 | SYGMH |

TABLE I

Mean EC$_{50}$ values of antibody MF4327 × MF5196-induced T cell activation and target cell lysis

| Functional read-out | Mean antibody MF4327xMF5196 EC$_{50}$ (ng/mL) | Range Mean antibody MF4327xMF5196 EC$_{50}$ (ng/mL) |
| --- | --- | --- |
| CD69 on CD4 T cells | 156.3 | 107.9-277.0 |
| CD25 on CD4 T cells | 351.1 | 199.0-589.9 |
| CD69 on CD8 T cells | 44.4 | 24.9-63.7 |
| CD25 on CD8 T cells | 95.7 | 69.7-131.1 |
| HL60 cell lysis | 68.2 | 29.5-115.2 |

Antibody MF4327xMF5196 EC$_{50}$ values were determined in an HL60 cytotoxicity assay. Data are from 6 healthy donors.

TABLE II antibody MF4327 × MF5196 induces AML blast lysis and T cell expansion in primary AML samples

| Patient no. | FAB classification | Risk classification | % CLEC12A positive* | E:T ratio | Recovery in control condition | % Blast killing with antibody MF4327x MF5196 | Fold T cell expansion with antibody MF4327x MF5196 | % blast killing with TTxCD3 control | Fold T cell expansion with TTxCD3 control |
| --- | --- | --- | --- | --- | --- | --- | --- | --- | --- |
| 10 | M1 | Good | 39% | 1:45 | 81% | 91% | 25 | 0% | 1 |
| 11 | M1 | Intermediate | 83% | 1:13 | 1591% | 23% | 6 | 5% | 1 |
| 12 | M2 | Good | 91% | 1:3 | 127% | 98% | 37 | 23% | 2 |
| 13 | M2 | Poor | 96% | 1:17 | 890% | 87% | 139 | 15% | 2 |
| 14 | M4 | Very poor | 88% | 1:13 | 225% | 92% | 64 | 69%# | 3 |
| 15 | M4/M5 | Intermediate | 58% | 1:49 | 41% | 39% | 25 | 24%# | 7 |
| 16 | M4/M5 | Intermediate | 74% | 1:31 | 644% | 0% | 15 | 0% | 1 |
| 17 | M4/M5 | Intermediate | 94% | 1:15 | 112% | 65% | 98 | 15% | 4 |
| 18 | M4/M5 | Poor | 99% | 1:46 | 1208% | 36% | 20 | 0% | 1 |
| 19 | M4/M5 | Poor | 100% | 1:97 | 366% | 33% | 60 | 0% | 1 |
| 20 | M4/M5 | Very poor | 79% | 1:32 | 373% | 31% | 157 | 0%# | 2 |

Primary AML patient samples taken at diagnosis were cultured for 10 days in a cytokine cocktail to support AML blast survival and proliferation. For quantification of AML blast lysis, AML blasts were gated based on SSC, CD45, CD33 and/or CD34 expression, antibody MF4327 × MF5196-induced T cell proliferation and AML blast lysis after 10 days was quantified relative to the PBS condition.
*Percentage CLEC12A-positive AML blasts in sample. Threshold for CLEC12A expression was set based on CLEC12A-negative lymphocyte fraction.
Samples 14, 15 and 20 were tested at 1,000 ng/mL IgG, while all other patient samples were tested at 200 ng/mL IgG. Specific blast lysis was calculated relative to the number of blasts in PBS condition at day 10.

TABLE III

Patient characteristics

| Patient no. | Gender | Age (Y) | Sample type | Fab classification | AML phenotype at diagnosis | Risk classification* | Primary/ Secondary AML | Disease state | % Blasts* | % T cells* |
| --- | --- | --- | --- | --- | --- | --- | --- | --- | --- | --- |
| 1 | F | 29 | PB | M4 | NA | Intermediate | — | CR | ND | ND |
| 2 | F | 50 | PB | M5 | NA | Poor risk | — | CR | ND | ND |
| 3 | F | 57 | PB | M1/M2 | NA | Poor risk | — | CR | ND | ND |
| 4 | M | 41 | PB | M1 | NA | Good risk | — | CR | ND | ND |
| 5 | F | 50 | PB | M1 | NA | Intermediate | — | CR | ND | ND |
| 6 | M | 40 | PB | M4 | NA | Intermediate | — | CR | ND | ND |
| 7a | M | 53 | BM | M1 | CD34−CD117+CD33+CD14−CD15− | Poor risk | Primary AML | Newly Diagnosed | 83 | 9 |
| 7b | M | 53 | PB | M1 | NA | Poor risk | — | CR after alloSCT | ND | ND |
| 8a | F | 60 | BM | M1/M2 | CD34+CD117+CD33+CD14−CD15− | Poor risk | Primary AML | Newly Diagnosed | 93 | 3 |
| 8b | F | 60 | PB | M1/M2 | NA | Poor risk | — | CR | ND | ND |
| 9a | M | 40 | BM | M5 | CD34−CD117+(partial)CD33+CD15+(partial)CD14+(partial) | Poor risk | Primary AML | Newly Diagnosed | 97 | 1 |

TABLE III-continued

Patient characteristics

| Patient no. | Gender | Age (Y) | Sample type | Fab classification | AML phenotype at diagnosis | Risk classification* | Primary/ Secondary AML | Disease state | % Blasts* | % T cells* |
|---|---|---|---|---|---|---|---|---|---|---|
| 9b | M | 41 | PB | M5 | NA | Poor risk | — | CR | ND | ND |
| 10 | F | 51 | BM | M1 | CD34+CD117+ CD33+CD14− CD15− | Good | Primary AML | Newly Diagnosed | 89 | 2 |
| 11 | M | 34 | BM | M1 | CD34+(partial) CD117+CD33+ CD15−CD14− | Intermediate | Primary AML | Newly Diagnosed | 91 | 7 |
| 12 | M | 49 | BM | M2 | CD34+CD117+ (partial) CD33+CD15− CD14− | Good | Primary AML | Newly Diagnosed | 67 | 20 |
| 13 | F | 45 | PB | M2 | CD34+CD117+ (partial), CD33+CD15+ CD14− | Poor | Primary AML | Newly Diagnosed | 84 | 5 |
| 14 | F | 60 | PB | M4 | CD34+(partial) CD117+(partial) CD33+CD15+ (partial)CD14+ (partial) | Very poor | Secondary AML (therapy related) | Newly Diagnosed | 93 | 7 |
| 15 | M | 42 | BM | M4/M5 | CD34+(partial) CD117+CD33+ CD15+CD14− | Intermediate | Primary AML | Newly Diagnosed | 97 | 2 |
| 16 | F | 44 | BM | M4/M5 | CD34− CD117+CD33+ CD14−CD15− | Intermediate | Primary AML | Newly Diagnosed | 92 | 3 |
| 17 | M | 66 | BM | M4/M5 | CD34−CD117− CD33+CD15+ CD14− | Intermediate | Primary AML | Newly Diagnosed | 92 | 6 |
| 18 | M | 59 | BM | M4/M5 | CD34− CD117+(partial) CD33+CD15+ CD14+(partial) | Poor | Primary AML | Newly Diagnosed | 91 | 2 |
| 19 | M | 54 | PB | M4/M5 | CD34−CD117− CD33+CD15+ CD14+(partial) | Poor | Primary AML | Newly Diagnosed | 97 | 1 |
| 20 | M | 14 | PB | M4/M5 | CD34+CD117+ CD33+CD14− CD15+ | Very poor | Primary AML | Newly Diagnosed | 96 | 3 |

Table. III. Characteristics of AML Patients. Abbreviations used are: Y: years; M: male; F: female; PB: peripheral blood; BM: bone marrow; CR: complete remission; alloSCT: allogeneic stem cell transplantation; ND: not determined; NA: not applicable.
*Percentage of AML blasts and T cells in sample after thawing and before functional assay.
Risk group classification was determined using criteria defined by the Dutch-Belgian Cooperative Trial Group for Hematology-Oncology (HOVON).

TABLE IV

Reagents for flow cytometry

| Compound | Company | Catalog# |
|---|---|---|
| 7AAD | Sigma-Aldrich | A9400 |
| CD1c-PE | Miltenyi | 130-090-508 |
| CD3-FITC | Biolegend | 300406 |
| CD3-PECy5 | Beckman coulter | A07749 |
| CD3-PECy7 | Biolegend | 300420 |
| CD3-APC | Beckman coulter | IM2467 |
| CD4-PE | Beckman coulter | 1707751 |
| CD4-ECD | Beckman coulter | 6604727 |
| CD4-PECy5.5 | Beckman coulter | B16491 |
| CD4-PECy7 | Biolegend | 317414 |
| CD4-BV421 | Biolegend | 300531 |
| CD4-Pacific blue | Beckman coulter | 49197 |
| CD5-BV421 | Biolegend | 300626 |
| CD8-AF647 | Invitrogen | MHCD0821 |
| CD8-AF700 | Invitrogen | MHCD0829 |
| CD10-APC | Biolegend | 312210 |
| CD10-APC-AF750 | Beckman coulter | A89310 |
| CD14-FITC | Biolegend | 325604 |
| CD14-ECD | Beckman coulter | IM2707U |
| CD16-PE | Beckman coulter | A07766 |
| CD16-PECy7 | Biolegend | 302016 |
| CD19-ECD | Beckman coulter | A07770 |
| CD19-AF700 | Invitrogen | MHCD1929 |
| CD25-PE | Beckman coulter | A07774 |
| CD33-PECy5 | Beckman coulter | IM2647 |
| CD33-PECy7 | Beckman coulter | A54824 |
| CD33-APC-AF750 | Beckman coulter | A70200 |
| CD34-ECD | Beckman coulter | IM2709U |
| CD34-PECy7 | Biolegend | 343516 |
| CD34-BV421 | Biolegend | 343609 |
| CD38-ECD | Beckman coulter | A99022 |
| CD38-PECy7 | Biolegend | 303516 |
| CD45 krome orange | Beckman coulter | A96416 |
| CD45RA-AF700 | BD bioscience | 560673 |
| CD45RA-Pacific blue | Biolegend | 304118 |
| CD45RO-ECD | Beckman coulter | IM2712U |
| CD56-PECy7 | Beckman coulter | 302016 |
| CD56-PECy7 | Biolegend | 318318 |
| CD69-APC | Beckman coulter | A80711 |
| CD90-BV510 | Biolegend | 328126 |
| CD90-FITC | BD bioscience | 555595 |
| CD117-APC | Beckman coulter | IM3638 |

TABLE IV-continued

Reagents for flow cytometry

| Compound | Company | Catalog# |
|---|---|---|
| CD123-BV421 | Biolegend | 306018 |
| CD135a-BV421 | BD bioscience | 564708 |
| CD197-AF488 | Biolegend | 335601 |
| CD303-PE | Miltenyi | 130-090-511 |
| CD304-PE | Miltenyi | 130-090-533 |
| CLEC12A-PE | R&D Systems | FAB2946p |
| CLEC12A-PE | Biolegend | 2368020 |
| IgG2a-PE | Biolegend | 400214 |
| IgG2b-PE | Beckman Coulter | 731601 |
| Lineage-BV510 | Biolegend | 348807 |
| Lineage-FITC | BD bioscience | 340546 |
| Anti-human IgG-PE | Invitrogen | |

Beckman is "Beckman coulter"; Sigma is "Sigma-Aldrich.

The invention claimed is:

1. A method of treating a subject for a CLEC12A positive cancer, the method comprising treating the subject in need thereof with two or more administrations of a bispecific antibody that binds CD3 and CLEC12A, wherein in a first administration a first amount of the bispecific antibody is administered and wherein in subsequent administrations the amount of bispecific antibody is higher than the amount of bispecific antibody in the first administration, wherein the first administration is a subtherapeutic amount of bispecific antibody.

2. The method of claim 1, wherein the amount of administered bispecific antibody in the second of said two or more administrations is higher than the amount of bispecific antibody in the first administration and lower than the amount of bispecific antibody in a third of said two or more administrations.

3. The method of claim 2, wherein the amount of administered bispecific antibody in the third of said two or more administrations is higher than the amount of bispecific antibody in the second of said two or more administrations and lower than the amount in a fourth of said two or more administrations.

4. The method of claim 1, wherein after the administrations of incremental amounts of said bispecific antibody, the bispecific antibody is administered at a constant dose in each of the subsequent administrations.

5. The method of claim 4, wherein the constant dose in each of the subsequent administrations is at least 15 mg of said bispecific antibody.

6. The method of claim 5, wherein the constant dose in each of the subsequent administrations is at least 60 mg of said bispecific antibody.

7. The method of claim 1, wherein the first amount of the bispecific antibody is 9 mg or less.

8. A method of purging CLEC12A positive hemopoietic cells from a subject and repopulating the hemopoietic system of said subject with normal CLEC12A positive cells, the method comprising administering to the subject in need thereof with two or more administrations of a bispecific antibody that binds CD3 and CLEC12A thereby killing CLEC12A positive malignant cells, and stimulating hemopoietic stem cells and/or hemopoietic progenitor cells of said subject to repopulate said hemopoietic system with newly formed hemopoietic stem cell derived CLEC12A positive cells, wherein the first administration is a subtherapeutic amount of bispecific antibody.

9. The method of claim 1, wherein the subject is a subject that is diagnosed to have acute myeloid leukaemia (AML), myelodysplastic syndrome (MDS), myelofibrosis (MF) or myeloproliferative neoplasm blast phase (MPN-BP).

10. A method of providing a subject with a hemopoietic stem cell sparing cancer treatment, the method comprising administering two or more administrations of a bispecific antibody that binds CD3 and CLEC12A to the subject in need thereof, wherein the first administration is a subtherapeutic amount of bispecific antibody.

11. The method of claim 10, wherein the subject has a CLEC12A positive cancer.

12. The method of claim 8, wherein the subject is a subject that is diagnosed to have acute myeloid leukaemia (AML), myelodysplastic syndrome (MDS), myelofibrosis (MF) or myeloproliferative neoplasm blast phase (MPN-BP).

13. The method of claim 10, wherein the subject is a subject that is diagnosed to have acute myeloid leukaemia (AML), myelodysplastic syndrome (MDS), myelofibrosis (MF) or myeloproliferative neoplasm blast phase (MPN-BP).

* * * * *

SEQUENCE LISTING

<160> NUMBER OF SEQ ID NOS: 60

<210> SEQ ID NO 1
<211> LENGTH: 275
<212> TYPE: PRT
<213> ORGANISM: Homo sapiens

<400> SEQUENCE: 1

```
Met Trp Ile Asp Phe Phe Thr Tyr Ser Ser Met Ser Glu Glu Val Thr
1               5                   10                  15

Tyr Ala Asp Leu Gln Phe Gln Asn Ser Ser Glu Met Glu Lys Ile Pro
            20                  25                  30

Glu Ile Gly Lys Phe Gly Glu Lys Ala Pro Pro Ala Pro Ser His Val
        35                  40                  45

Trp Arg Pro Ala Ala Leu Phe Leu Thr Leu Leu Cys Leu Leu Leu Leu
    50                  55                  60

Ile Gly Leu Gly Val Leu Ala Ser Met Phe His Val Thr Leu Lys Ile
65                  70                  75                  80

Glu Met Lys Lys Met Asn Lys Leu Gln Asn Ile Ser Glu Glu Leu Gln
                85                  90                  95

Arg Asn Ile Ser Leu Gln Leu Met Ser Asn Met Asn Ile Ser Asn Lys
            100                 105                 110

Ile Arg Asn Leu Ser Thr Thr Leu Gln Thr Ile Ala Thr Lys Leu Cys
        115                 120                 125

Arg Glu Leu Tyr Ser Lys Glu Gln Glu His Lys Cys Lys Pro Cys Pro
    130                 135                 140

Arg Arg Trp Ile Trp His Lys Asp Ser Cys Tyr Phe Leu Ser Asp Asp
145                 150                 155                 160

Val Gln Thr Trp Gln Glu Ser Lys Met Ala Cys Ala Ala Gln Asn Ala
                165                 170                 175

Ser Leu Leu Lys Ile Asn Asn Lys Asn Ala Leu Glu Phe Ile Lys Ser
            180                 185                 190

Gln Ser Arg Ser Tyr Asp Tyr Trp Leu Gly Leu Ser Pro Glu Glu Asp
        195                 200                 205

Ser Thr Arg Gly Met Arg Val Asp Asn Ile Ile Asn Ser Ser Ala Trp
    210                 215                 220

Val Ile Arg Asn Ala Pro Asp Leu Asn Asn Met Tyr Cys Gly Tyr Ile
225                 230                 235                 240

Asn Arg Leu Tyr Val Gln Tyr Tyr His Cys Thr Tyr Lys Lys Arg Met
                245                 250                 255

Ile Cys Glu Lys Met Ala Asn Pro Val Gln Leu Gly Ser Thr Tyr Phe
            260                 265                 270

Arg Glu Ala
        275
```

<210> SEQ ID NO 2
<211> LENGTH: 182
<212> TYPE: PRT
<213> ORGANISM: Homo sapiens

<400> SEQUENCE: 2

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 3
<211> LENGTH: 171
<212> TYPE: PRT
<213> ORGANISM: Homo sapiens

<400> SEQUENCE: 3

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

```
Asn Asp Gln Val Tyr Gln Pro Leu Arg Asp Arg Asp Ala Gln Tyr
145                 150                 155                 160

Ser His Leu Gly Gly Asn Trp Ala Arg Asn Lys
                165                 170
```

<210> SEQ ID NO 4
<211> LENGTH: 207
<212> TYPE: PRT
<213> ORGANISM: Homo sapiens

<400> SEQUENCE: 4

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

<210> SEQ ID NO 5
<211> LENGTH: 164
<212> TYPE: PRT
<213> ORGANISM: Homo sapiens

<400> SEQUENCE: 5

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95
```

```
Gly Gly Lys Pro Gln Arg Arg Lys Asn Pro Gln Gly Leu Tyr Asn
                100                 105                 110

Glu Leu Gln Lys Asp Lys Met Ala Glu Ala Tyr Ser Glu Ile Gly Met
            115                 120                 125

Lys Gly Glu Arg Arg Gly Lys Gly His Asp Gly Leu Tyr Gln Gly
        130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 6
<211> LENGTH: 162
<212> TYPE: PRT
<213> ORGANISM: Homo sapiens

<400> SEQUENCE: 6

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 7
<211> LENGTH: 267
<212> TYPE: PRT
<213> ORGANISM: Homo sapiens

<400> SEQUENCE: 7

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
                20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
```

```
                85                  90                  95
Pro Ala Leu Val His Gln Arg Pro Ala Pro Ser Thr Val Thr Thr
                100                 105                 110
Ala Gly Val Thr Pro Gln Pro Glu Ser Leu Ser Pro Ser Gly Lys Glu
            115                 120                 125
Pro Ala Ala Ser Ser Pro Ser Ser Asn Asn Thr Ala Ala Thr Thr Ala
        130                 135                 140
Ala Ile Val Pro Gly Ser Gln Leu Met Pro Ser Lys Ser Pro Ser Thr
145                 150                 155                 160
Gly Thr Thr Glu Ile Ser Ser His Glu Ser Ser His Gly Thr Pro Ser
                165                 170                 175
Gln Thr Thr Ala Lys Asn Trp Glu Leu Thr Ala Ser Ala Ser His Gln
            180                 185                 190
Pro Pro Gly Val Tyr Pro Gln Gly His Ser Asp Thr Thr Val Ala Ile
        195                 200                 205
Ser Thr Ser Thr Val Leu Leu Cys Gly Leu Ser Ala Val Ser Leu Leu
210                 215                 220
Ala Cys Tyr Leu Lys Ser Arg Gln Thr Pro Pro Leu Ala Ser Val Glu
225                 230                 235                 240
Met Glu Ala Met Glu Ala Leu Pro Val Thr Trp Gly Thr Ser Ser Arg
                245                 250                 255
Asp Glu Asp Leu Glu Asn Cys Ser His His Leu
                260                 265

<210> SEQ ID NO 8
<211> LENGTH: 200
<212> TYPE: PRT
<213> ORGANISM: Homo sapiens

<400> SEQUENCE: 8

Met Ala Pro Arg Arg Ala Arg Gly Cys Arg Thr Leu Gly Leu Pro Ala
1               5                   10                  15
Leu Leu Leu Leu Leu Leu Leu Arg Pro Pro Ala Thr Arg Gly Ile Thr
                20                  25                  30
Cys Pro Pro Pro Met Ser Val Glu His Ala Asp Ile Trp Val Lys Ser
            35                  40                  45
Tyr Ser Leu Tyr Ser Arg Glu Arg Tyr Ile Cys Asn Ser Gly Phe Lys
        50                  55                  60
Arg Lys Ala Gly Thr Ser Ser Leu Thr Glu Cys Val Leu Asn Lys Ala
65                  70                  75                  80
Thr Asn Val Ala His Trp Thr Thr Pro Ser Leu Lys Cys Ile Arg Asp
                85                  90                  95
Pro Ala Leu Val His Gln Arg Pro Ala Pro Ser Thr Val Thr Thr
                100                 105                 110
Ala Gly Val Thr Pro Gln Pro Glu Ser Leu Ser Pro Ser Gly Lys Glu
            115                 120                 125
Pro Ala Ala Ser Ser Pro Ser Ser Asn Asn Thr Ala Ala Thr Thr Ala
        130                 135                 140
Ala Ile Val Pro Gly Ser Gln Leu Met Pro Ser Lys Ser Pro Ser Thr
145                 150                 155                 160
Gly Thr Thr Glu Ile Ser Ser His Glu Ser Ser His Gly Thr Pro Ser
                165                 170                 175
Gln Thr Thr Ala Lys Asn Trp Glu Leu Thr Ala Ser Ala Ser His Gln
            180                 185                 190
```

```
Pro Pro Gly Val Tyr Pro Gln Gly
        195                 200

<210> SEQ ID NO 9
<211> LENGTH: 8
<212> TYPE: PRT
<213> ORGANISM: Artificial Sequence
<220> FEATURE:
<223> OTHER INFORMATION: CLEC12A 4327 HCDR1

<400> SEQUENCE: 9

Ser Gly Tyr Thr Phe Thr Gly Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: CLEC12A 4327 HCDR2

<400> SEQUENCE: 10

Ile Ile Asn Pro Ser Gly Gly Ser
1               5

<210> SEQ ID NO 11
<211> LENGTH: 9
<212> TYPE: PRT
<213> ORGANISM: Artificial Sequence
<220> FEATURE:
<223> OTHER INFORMATION: CLEC12A 4327 HCDR3

<400> SEQUENCE: 11

Gly Thr Thr Gly Asp Trp Phe Asp Tyr
1               5

<210> SEQ ID NO 12
<211> LENGTH: 118
<212> TYPE: PRT
<213> ORGANISM: Artificial Sequence
<220> FEATURE:
<223> OTHER INFORMATION: 4327 VH

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Thr Thr Gly Asp Trp Phe Asp Tyr Trp Gly Gln Gly Thr
            100                 105                 110

Leu Val Thr Val Ser Ser
        115

<210> SEQ ID NO 13
<211> LENGTH: 8
```

```
<212> TYPE: PRT
<213> ORGANISM: Artificial Sequence
<220> FEATURE:
<223> OTHER INFORMATION: CLEC12A 4331 HCDR1

<400> SEQUENCE: 13

Ser Gly Tyr Thr Phe Thr Ser Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: CLEC12A 4331 HCDR2

<400> SEQUENCE: 14

Ile Ile Asn Pro Ser Gly Gly Ser
1               5

<210> SEQ ID NO 15
<211> LENGTH: 9
<212> TYPE: PRT
<213> ORGANISM: Artificial Sequence
<220> FEATURE:
<223> OTHER INFORMATION: CLEC12A 4331 HCDR3

<400> SEQUENCE: 15

Gly Asn Tyr Gly Asp Glu Phe Asp Tyr
1               5

<210> SEQ ID NO 16
<211> LENGTH: 118
<212> TYPE: PRT
<213> ORGANISM: Artificial Sequence
<220> FEATURE:
<223> OTHER INFORMATION: 4331 VH

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Tyr Gly Asp Glu Phe Asp Tyr Trp Gly Gln Gly Thr
            100                 105                 110

Leu Val Thr Val Ser Ser
        115

<210> SEQ ID NO 17
<211> LENGTH: 8
<212> TYPE: PRT
<213> ORGANISM: Artificial Sequence
<220> FEATURE:
<223> OTHER INFORMATION: CLEC12A HCDR1

<400> SEQUENCE: 17
```

```
Ser Gly Tyr Thr Phe Thr Gly Tyr
1               5

<210> SEQ ID NO 18
<211> LENGTH: 8
<212> TYPE: PRT
<213> ORGANISM: Artificial Sequence
<220> FEATURE:
<223> OTHER INFORMATION: CLEC12A HCDR2

<400> SEQUENCE: 18

Trp Ile Asn Pro Asn Ser Gly Gly
1               5

<210> SEQ ID NO 19
<211> LENGTH: 10
<212> TYPE: PRT
<213> ORGANISM: Artificial Sequence
<220> FEATURE:
<223> OTHER INFORMATION: CLEC12A HCDR3

<400> SEQUENCE: 19

Asp Gly Tyr Phe Ala Asp Ala Phe Asp Tyr
1               5                   10

<210> SEQ ID NO 20
<211> LENGTH: 119
<212> TYPE: PRT
<213> ORGANISM: Artificial Sequence
<220> FEATURE:
<223> OTHER INFORMATION: CLEC12A VH

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Tyr Phe Ala Asp Ala Phe Asp Tyr Trp Gly Gln Gly
            100                 105                 110

Thr Leu Val Thr Val Ser Ser
        115

<210> SEQ ID NO 21
<211> LENGTH: 8
<212> TYPE: PRT
<213> ORGANISM: Artificial Sequence
<220> FEATURE:
<223> OTHER INFORMATION: 3056 HCDR1

<400> SEQUENCE: 21

Gly Phe Thr Phe Ser Ser Tyr Gly
1               5

<210> SEQ ID NO 22
```

```
<211> LENGTH: 8
<212> TYPE: PRT
<213> ORGANISM: Artificial Sequence
<220> FEATURE:
<223> OTHER INFORMATION: 3056 HCDR2

<400> SEQUENCE: 22

Ile Trp Tyr Asn Gly Arg Lys Gln
1               5

<210> SEQ ID NO 23
<211> LENGTH: 9
<212> TYPE: PRT
<213> ORGANISM: Artificial Sequence
<220> FEATURE:
<223> OTHER INFORMATION: 3056 HCDR3

<400> SEQUENCE: 23

Gly Thr Gly Tyr Asn Trp Phe Asp Pro
1               5

<210> SEQ ID NO 24
<211> LENGTH: 118
<212> TYPE: PRT
<213> ORGANISM: Artificial Sequence
<220> FEATURE:
<223> OTHER INFORMATION: MF3056 VH

<400> SEQUENCE: 24

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 25
<211> LENGTH: 118
<212> TYPE: PRT
<213> ORGANISM: Artificial Sequence
<220> FEATURE:
<223> OTHER INFORMATION: MF3874

<400> SEQUENCE: 25

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 26
<211> LENGTH: 118
<212> TYPE: PRT
<213> ORGANISM: Artificial Sequence
<220> FEATURE:
<223> OTHER INFORMATION: MF3878

<400> SEQUENCE: 26

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Ala Ile Trp Tyr Asn Gly Arg Lys Gln Asp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 27
<211> LENGTH: 118
<212> TYPE: PRT
<213> ORGANISM: Artificial Sequence
<220> FEATURE:
<223> OTHER INFORMATION: MF3883

<400> SEQUENCE: 27

Gln Val Gln Leu Val Gln Ser Gly Gly Gly Val Val Gln Pro Gly Arg
 1               5                  10                  15

Ser Leu Arg Leu Ser Cys Val Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asn Gly Arg Lys Gln Asp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Thr Gly Tyr Asn Trp Phe Asp Pro Trp Gly Gln Gly Thr
            100                 105                 110

Leu Val Thr Val Ser Ser
```

<210> SEQ ID NO 28
<211> LENGTH: 118
<212> TYPE: PRT
<213> ORGANISM: Artificial Sequence
<220> FEATURE:
<223> OTHER INFORMATION: MF3886

<400> SEQUENCE: 28

```
Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Tyr Asn Trp Phe Asp Pro Trp Gly Gln Gly Thr
            100                 105                 110

Leu Val Thr Val Ser Ser
        115
```

<210> SEQ ID NO 29
<211> LENGTH: 118
<212> TYPE: PRT
<213> ORGANISM: Artificial Sequence
<220> FEATURE:
<223> OTHER INFORMATION: MF3891

<400> SEQUENCE: 29

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Tyr Asn Trp Phe Asp Pro Trp Gly Gln Gly Thr
            100                 105                 110

Leu Val Thr Val Ser Ser
        115
```

<210> SEQ ID NO 30
<211> LENGTH: 9
<212> TYPE: PRT
<213> ORGANISM: Artificial Sequence
<220> FEATURE:
<223> OTHER INFORMATION: 3896 HCDR2

<400> SEQUENCE: 30

Ile Trp Tyr Ser Gly Ser Lys Lys Asn
1               5

<210> SEQ ID NO 31
<211> LENGTH: 118
<212> TYPE: PRT
<213> ORGANISM: Artificial Sequence
<220> FEATURE:
<223> OTHER INFORMATION: 3896 VH

<400> SEQUENCE: 31

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
                20                  25                  30

Gly Met His Trp Val Arg Gln Ala Pro Gly Lys Gly Leu Glu Trp Val
            35                  40                  45

Ala Ile Ile Trp Tyr Ser Gly Ser Lys Lys Asn Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Tyr Asn Trp Phe Asp Pro Trp Gly Gln Gly Thr
            100                 105                 110

Leu Val Thr Val Ser Ser
            115

<210> SEQ ID NO 32
<211> LENGTH: 8
<212> TYPE: PRT
<213> ORGANISM: Artificial Sequence
<220> FEATURE:
<223> OTHER INFORMATION: MF5192 HCDR2

<400> SEQUENCE: 32

Ile Trp Tyr His Gly Arg Lys Gln
1               5

<210> SEQ ID NO 33
<211> LENGTH: 118
<212> TYPE: PRT
<213> ORGANISM: Artificial Sequence
<220> FEATURE:
<223> OTHER INFORMATION: MF5192

<400> SEQUENCE: 33

Gln Val Gln Leu Val Gln Ser Gly Gly Val Val Gln Pro Gly Arg
1               5                   10                  15

Ser Leu Arg Leu Ser Cys Val Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ala Ile Trp Tyr His Gly Arg Lys Gln Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

-continued

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 34
<211> LENGTH: 8
<212> TYPE: PRT
<213> ORGANISM: Artificial Sequence
<220> FEATURE:
<223> OTHER INFORMATION: MF5193 HCDR2

<400> SEQUENCE: 34

Ile Trp Tyr His Ala Arg Lys Gln
1               5

<210> SEQ ID NO 35
<211> LENGTH: 118
<212> TYPE: PRT
<213> ORGANISM: Artificial Sequence
<220> FEATURE:
<223> OTHER INFORMATION: MF5193

<400> SEQUENCE: 35

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr His Ala Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 36
<211> LENGTH: 8
<212> TYPE: PRT
<213> ORGANISM: Artificial Sequence
<220> FEATURE:
<223> OTHER INFORMATION: MF5196 HCDR2

<400> SEQUENCE: 36

Ile Trp Tyr Asn Ala Arg Lys Gln
1               5

<210> SEQ ID NO 37
<211> LENGTH: 118
<212> TYPE: PRT
<213> ORGANISM: Artificial Sequence
<220> FEATURE:
<223> OTHER INFORMATION: MF5196

<400> SEQUENCE: 37

Gln Val Gln Leu Val Gln Ser Gly Gly Gly Val Val Gln Pro Gly Arg
1               5                   10                  15

-continued

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
            115

<210> SEQ ID NO 38
<211> LENGTH: 118
<212> TYPE: PRT
<213> ORGANISM: Artificial Sequence
<220> FEATURE:
<223> OTHER INFORMATION: MF5603

<400> SEQUENCE: 38

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Glu Tyr Ile Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
            115

<210> SEQ ID NO 39
<211> LENGTH: 118
<212> TYPE: PRT
<213> ORGANISM: Artificial Sequence
<220> FEATURE:
<223> OTHER INFORMATION: MF5616

<400> SEQUENCE: 39

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Glu Tyr Asn Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: MF5626

<400> SEQUENCE: 40

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Glu Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 41
<211> LENGTH: 118
<212> TYPE: PRT
<213> ORGANISM: Artificial Sequence
<220> FEATURE:
<223> OTHER INFORMATION: MF5630

<400> SEQUENCE: 41

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Tyr Asp Pro Trp Gly Gln Gly Thr
            100                 105                 110

Leu Val Thr Val Ser Ser
        115
```

<210> SEQ ID NO 42
<211> LENGTH: 118
<212> TYPE: PRT
<213> ORGANISM: Artificial Sequence
<220> FEATURE:
<223> OTHER INFORMATION: MF5648

<400> SEQUENCE: 42

```
Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Glu Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115
```

<210> SEQ ID NO 43
<211> LENGTH: 118
<212> TYPE: PRT
<213> ORGANISM: Artificial Sequence
<220> FEATURE:
<223> OTHER INFORMATION: MF5661

<400> SEQUENCE: 43

```
Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Gln Ile Trp Tyr Asn Ala Arg Lys Gln Glu Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115
```

<210> SEQ ID NO 44
<211> LENGTH: 118
<212> TYPE: PRT
<213> ORGANISM: Artificial Sequence
<220> FEATURE:
<223> OTHER INFORMATION: MF5694

<400> SEQUENCE: 44

```
Gln Val Gln Leu Val Gln Ser Gly Gly Gly Val Val Gln Pro Gly Arg
1               5                   10                  15
```

```
Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Glu Tyr Ser Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
            115
```

<210> SEQ ID NO 45
<211> LENGTH: 8
<212> TYPE: PRT
<213> ORGANISM: Artificial Sequence
<220> FEATURE:
<223> OTHER INFORMATION: MF5197 HCDR2

<400> SEQUENCE: 45

```
Ile Trp Tyr Asn Thr Arg Lys Gln
1               5
```

<210> SEQ ID NO 46
<211> LENGTH: 118
<212> TYPE: PRT
<213> ORGANISM: Artificial Sequence
<220> FEATURE:
<223> OTHER INFORMATION: MF5197

<400> SEQUENCE: 46

```
Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Thr Arg Lys Gln Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
            115
```

<210> SEQ ID NO 47
<211> LENGTH: 8
<212> TYPE: PRT
<213> ORGANISM: Artificial Sequence
<220> FEATURE:
<223> OTHER INFORMATION: MF5351 HCDR2

<400> SEQUENCE: 47

```
Ile Trp Tyr Asp Gly Lys Asn Thr
1               5
```

```
<210> SEQ ID NO 48
<211> LENGTH: 118
<212> TYPE: PRT
<213> ORGANISM: Artificial Sequence
<220> FEATURE:
<223> OTHER INFORMATION: MF5351

<400> SEQUENCE: 48

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Met Ile Trp Tyr Asp Gly Lys Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115
```

```
<210> SEQ ID NO 49
<211> LENGTH: 8
<212> TYPE: PRT
<213> ORGANISM: Artificial Sequence
<220> FEATURE:
<223> OTHER INFORMATION: MF5354 HCDR2

<400> SEQUENCE: 49

Ile Tyr Tyr Asp Gly Ser Arg Thr
1               5
```

```
<210> SEQ ID NO 50
<211> LENGTH: 118
<212> TYPE: PRT
<213> ORGANISM: Artificial Sequence
<220> FEATURE:
<223> OTHER INFORMATION: MF5354

<400> SEQUENCE: 50

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Gln Ile Tyr Tyr Asp Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
```

Leu Val Thr Val Ser Ser
        115

<210> SEQ ID NO 51
<211> LENGTH: 8
<212> TYPE: PRT
<213> ORGANISM: Artificial Sequence
<220> FEATURE:
<223> OTHER INFORMATION: MF5356 HCDR2

<400> SEQUENCE: 51

Ile Trp His Asp Gly Arg Lys Thr
1               5

<210> SEQ ID NO 52
<211> LENGTH: 118
<212> TYPE: PRT
<213> ORGANISM: Artificial Sequence
<220> FEATURE:
<223> OTHER INFORMATION: MF5356

<400> SEQUENCE: 52

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Lys Tyr
            20                  25                  30

Gly Met His Trp Val Arg Gln Ala Pro Gly Lys Gly Leu Glu Trp Val
        35                  40                  45

Ala Gln Ile Trp His Asp Gly Arg Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 53
<211> LENGTH: 6
<212> TYPE: PRT
<213> ORGANISM: Artificial Sequence
<220> FEATURE:
<223> OTHER INFORMATION: VL CDR1

<400> SEQUENCE: 53

Gln Ser Ile Ser Ser Tyr
1               5

<210> SEQ ID NO 54
<211> LENGTH: 7
<212> TYPE: PRT
<213> ORGANISM: Artificial Sequence
<220> FEATURE:
<223> OTHER INFORMATION: VL CDR2

<400> SEQUENCE: 54

Ala Ala Ser Ser Leu Gln Ser
1               5

```
<210> SEQ ID NO 55
<211> LENGTH: 7
<212> TYPE: PRT
<213> ORGANISM: Artificial Sequence
<220> FEATURE:
<223> OTHER INFORMATION: VL CDR3

<400> SEQUENCE: 55

Gln Gln Ser Tyr Ser Thr Pro
1               5

<210> SEQ ID NO 56
<211> LENGTH: 95
<212> TYPE: PRT
<213> ORGANISM: Artificial Sequence
<220> FEATURE:
<223> OTHER INFORMATION: IgVk1-39*01

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 57
<211> LENGTH: 107
<212> TYPE: PRT
<213> ORGANISM: Artificial Sequence
<220> FEATURE:
<223> OTHER INFORMATION: Common Light Chain IgKV1*39/jk1

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 58
<211> LENGTH: 108
<212> TYPE: PRT
<213> ORGANISM: Artificial Sequence
<220> FEATURE:
<223> OTHER INFORMATION: Common Light Chain IgKV1*39/jk5
```

```
<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 59
<211> LENGTH: 127
<212> TYPE: PRT
<213> ORGANISM: Artificial Sequence
<220> FEATURE:
<223> OTHER INFORMATION: MF1337 TT VH

<400> SEQUENCE: 59

Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
            20                  25                  30

Asp Ile Asn Trp Val Arg Gln Ala Pro Gly Gln Gly Leu Glu Trp Met
        35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110

Ala Leu Asp Val Trp Gly Gln Gly Thr Thr Val Thr Val Ser Ser
        115                 120                 125

<210> SEQ ID NO 60
<211> LENGTH: 5
<212> TYPE: PRT
<213> ORGANISM: Artificial Sequence
<220> FEATURE:
<223> OTHER INFORMATION: 3056 HCDR1

<400> SEQUENCE: 60

Ser Tyr Gly Met His
1               5
```